(12) United States Patent
Amos et al.

(10) Patent No.: US 9,622,537 B2
(45) Date of Patent: *Apr. 18, 2017

(54) FOOTWEAR HAVING SENSOR SYSTEM

(71) Applicant: Nike, Inc., Beaverton, OR (US)

(72) Inventors: Michael S. Amos, Beaverton, OR (US); Andrew A. Owings, Portland, OR (US); Allan M. Schrock, Portland, OR (US); Anthony C. Dean, Newberg, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/809,954

(22) Filed: Jul. 27, 2015

(65) Prior Publication Data

US 2016/0081418 A1  Mar. 24, 2016

Related U.S. Application Data

(63) Continuation of application No. 13/399,778, filed on Feb. 17, 2012, now Pat. No. 9,089,182, which is a
(Continued)

(51) Int. Cl.
*A43B 3/00* (2006.01)
*A61B 5/103* (2006.01)
(Continued)

(52) U.S. Cl.
CPC ............ *A43B 3/0005* (2013.01); *A43B 3/00* (2013.01); *A43B 17/006* (2013.01);
(Continued)

(58) Field of Classification Search
CPC .......... A43B 3/00; A43B 3/005; A43B 13/38; A43B 17/00
(Continued)

(56) References Cited

U.S. PATENT DOCUMENTS 3,270,564 A   9/1966 Evans
4,372,558 A   2/1983 Shimamoto et al.
(Continued)

FOREIGN PATENT DOCUMENTS

CA   2668946 A1   5/2008
CN   1101757A A   4/1995
(Continued)

OTHER PUBLICATIONS

Aug. 7, 2013—(WO) ISR and WO—App. No. PCT/US2013/027397.
(Continued)

*Primary Examiner* — Marie Bays
(74) *Attorney, Agent, or Firm* — Banner & Witcoff, Ltd.

(57) ABSTRACT

An article of footwear includes an upper member and a sole structure, with a sensor system connected to the sole structure. The sensor system includes a plurality of sensors that are configured for detecting forces exerted by a user's foot on the sensor. Each sensor includes two electrodes that are in communication with a force sensitive resistive material. The electrodes and the force sensitive resistive material may have multi-lobed shapes. Additionally, the sensor system may be provided on an insert that may form a sole member of the article of footwear. The insert may have slits therethrough, and may have a defined peripheral shape.

25 Claims, 23 Drawing Sheets

Related U.S. Application Data continuation-in-part of application No. 12/483,824, filed on Jun. 12, 2009, now Pat. No. 8,676,541, and a continuation-in-part of application No. 12/483,828, filed on Jun. 12, 2009, now Pat. No. 9,462,844.

(60) Provisional application No. 61/061,427, filed on Jun. 13, 2008, provisional application No. 61/138,048, filed on Dec. 16, 2008, provisional application No. 61/443,911, filed on Feb. 17, 2011.

(51) Int. Cl.
| | |
|---|---|
| A61B 5/00 | (2006.01) |
| G06F 3/033 | (2013.01) |
| G01C 22/00 | (2006.01) |
| G01L 1/26 | (2006.01) |
| A43B 17/00 | (2006.01) |

(52) U.S. Cl.
CPC .......... *A61B 5/1038* (2013.01); *A61B 5/6807* (2013.01); *G01C 22/006* (2013.01); *G01L 1/26* (2013.01); *G06F 3/0334* (2013.01); *A61B 2562/0252* (2013.01); *A63F 2300/1012* (2013.01); *A63F 2300/1031* (2013.01); *F04C 2270/041* (2013.01)

(58) Field of Classification Search
USPC .............................. 36/1, 114, 136, 137, 138
See application file for complete search history.

(56) References Cited

U.S. PATENT DOCUMENTS

| | | |
|---|---|---|
| 4,373,651 A | 2/1983 | Fanslow |
| 4,518,267 A | 5/1985 | Hepp |
| 4,578,969 A | 4/1986 | Larson |
| 4,647,918 A | 3/1987 | Goforth |
| 4,703,445 A | 10/1987 | Dassler |
| 4,745,930 A | 5/1988 | Confer |
| 4,814,661 A | 3/1989 | Ratzlaff et al. |
| 4,866,412 A | 9/1989 | Rzepczynski |
| 5,010,774 A | 4/1991 | Kikuo et al. |
| 5,033,291 A | 7/1991 | Podoloff et al. |
| 5,047,952 A | 9/1991 | Kramer et al. |
| 5,050,962 A | 9/1991 | Monnier et al. |
| 5,150,536 A | 9/1992 | Strong |
| 5,154,960 A | 10/1992 | Mucci et al. |
| 5,249,967 A | 10/1993 | O'Leary et al. |
| 5,303,131 A | 4/1994 | Wu |
| 5,323,650 A | 6/1994 | Fullen et al. |
| 5,373,651 A | 12/1994 | Wood |
| 5,374,821 A | 12/1994 | Muhs et al. |
| 5,393,651 A | 2/1995 | Hoshi |
| 5,408,873 A | 4/1995 | Schmidt et al. |
| 5,419,562 A | 5/1995 | Cromarty |
| 5,422,521 A | 6/1995 | Neer et al. |
| 5,444,462 A | 8/1995 | Wambach |
| 5,471,405 A | 11/1995 | Marsh |
| 5,500,635 A | 3/1996 | Mott |
| 5,636,146 A | 6/1997 | Flentov et al. |
| 5,636,378 A | 6/1997 | Griffith |
| 5,638,300 A | 6/1997 | Johnson |
| 5,644,858 A | 7/1997 | Bemis |
| 5,655,316 A | 8/1997 | Huang |
| 5,697,791 A | 12/1997 | Nashner et al. |
| 5,702,323 A | 12/1997 | Poulton |
| 5,714,706 A | 2/1998 | Nakada et al. |
| 5,720,200 A | 2/1998 | Anderson et al. |
| 5,724,265 A | 3/1998 | Hutchings |
| 5,764,786 A | 6/1998 | Kuwashima et al. |
| 5,785,666 A | 7/1998 | Costello et al. |
| 5,812,142 A | 9/1998 | Small et al. |
| 5,813,142 A | 9/1998 | Demon |
| 5,813,406 A | 9/1998 | Kramer et al. |
| 5,844,861 A | 12/1998 | Maurer |
| 5,889,464 A | 3/1999 | Huang |
| 5,903,454 A | 5/1999 | Hoffberg et al. |
| 5,907,819 A | 5/1999 | Johnson |
| 5,913,727 A | 6/1999 | Ahdoot |
| 5,929,332 A | 7/1999 | Brown |
| 5,960,380 A | 9/1999 | Flentov et al. |
| 5,963,891 A | 10/1999 | Walker et al. |
| 6,017,128 A | 1/2000 | Goldston et al. |
| 6,018,705 A | 1/2000 | Gaudet et al. |
| 6,050,962 A | 4/2000 | Kramer et al. |
| 6,066,075 A | 5/2000 | Poulton |
| 6,081,750 A | 6/2000 | Hoffberg et al. |
| 6,122,340 A | 9/2000 | Darley et al. |
| 6,122,846 A | 9/2000 | Gray et al. |
| 6,148,280 A | 11/2000 | Kramer |
| 6,174,294 B1 | 1/2001 | Crabb et al. |
| 6,195,921 B1 | 3/2001 | Truong |
| 6,198,394 B1 | 3/2001 | Jacobsen et al. |
| 6,226,577 B1 | 5/2001 | Yeo |
| 6,266,623 B1 | 7/2001 | Vock et al. |
| 6,287,200 B1 | 9/2001 | Sharma |
| 6,298,314 B1 | 10/2001 | Blackadar et al. |
| 6,330,757 B1 | 12/2001 | Russell |
| 6,336,365 B1 | 1/2002 | Blackadar et al. |
| 6,356,856 B1 | 3/2002 | Damen et al. |
| 6,357,147 B1 | 3/2002 | Darley et al. |
| 6,360,597 B1 | 3/2002 | Hubbard, Jr. |
| 6,426,490 B1 | 7/2002 | Storz |
| 6,428,490 B1 | 8/2002 | Kramer et al. |
| 6,430,843 B1 | 8/2002 | Potter et al. |
| 6,496,787 B1 | 12/2002 | Flentov et al. |
| 6,496,952 B1 | 12/2002 | Osada et al. |
| 6,498,994 B2 | 12/2002 | Vock et al. |
| 6,515,284 B1 | 2/2003 | Walle et al. |
| 6,516,284 B2 | 2/2003 | Flentov et al. |
| 6,536,139 B2 | 3/2003 | Darley et al. |
| 6,539,336 B1 | 3/2003 | Vock et al. |
| 6,544,858 B2 | 4/2003 | Beekman et al. |
| 6,560,903 B1 | 5/2003 | Darley |
| 6,578,291 B2 | 6/2003 | Hirsch et al. |
| 6,611,789 B1 | 8/2003 | Darley |
| 6,640,144 B1 | 10/2003 | Huang et al. |
| 6,656,042 B2 | 12/2003 | Reiss et al. |
| 6,718,200 B2 | 4/2004 | Marmaropoulos et al. |
| 6,748,462 B2 | 6/2004 | Dubil et al. |
| 6,778,973 B2 | 8/2004 | Harlan |
| 6,785,579 B2 | 8/2004 | Huang et al. |
| 6,785,805 B1 | 8/2004 | House et al. |
| 6,808,462 B2 | 10/2004 | Snyder et al. |
| 6,829,512 B2 | 12/2004 | Huang et al. |
| 6,836,744 B1 | 12/2004 | Asphahani et al. |
| 6,876,947 B1 | 4/2005 | Darley et al. |
| 6,882,897 B1 | 4/2005 | Fernandez |
| 6,885,971 B2 | 4/2005 | Vock et al. |
| 6,889,282 B2 | 5/2005 | Schollenberger |
| 6,892,216 B2 | 5/2005 | Coburn, II et al. |
| 6,909,420 B1 | 6/2005 | Nicolas et al. |
| 6,922,664 B1 | 7/2005 | Fernandez et al. |
| 6,932,698 B2 | 8/2005 | Sprogis |
| 6,959,259 B2 | 10/2005 | Vock et al. |
| 6,963,818 B2 | 11/2005 | Flentov et al. |
| 6,978,320 B2 | 12/2005 | Nonaka |
| 7,030,861 B1 | 4/2006 | Westerman et al. |
| 7,045,151 B2 | 5/2006 | Trant |
| 7,046,151 B2 | 5/2006 | Dundon |
| 7,054,784 B2 | 5/2006 | Flentov et al. |
| 7,057,551 B1 | 6/2006 | Vogt |
| 7,070,571 B2 | 7/2006 | Kramer et al. |
| 7,072,789 B2 | 7/2006 | Vock et al. |
| 7,092,846 B2 | 8/2006 | Vock et al. |
| 7,152,343 B2 | 12/2006 | Whatley |
| 7,162,392 B2 | 1/2007 | Vock et al. |
| 7,171,331 B2 | 1/2007 | Vock et al. |
| 7,200,517 B2 | 4/2007 | Darley et al. |
| 7,245,898 B2 | 7/2007 | Van Bosch et al. |
| 7,277,021 B2 | 10/2007 | Beebe et al. |
| 7,283,647 B2 | 10/2007 | McNitt |
| 7,304,580 B2 | 12/2007 | Sullivan et al. |

(56) References Cited

U.S. PATENT DOCUMENTS

| | | |
|---|---|---|
| 7,310,895 B2 | 12/2007 | Whittlesey et al. |
| 7,383,728 B2 | 6/2008 | Noble et al. |
| RE40,474 E | 9/2008 | Quellais et al. |
| 7,426,873 B1 | 9/2008 | Kholwadwala et al. |
| 7,428,471 B2 | 9/2008 | Darley et al. |
| 7,433,805 B2 | 10/2008 | Vock et al. |
| 7,457,724 B2 | 11/2008 | Vock et al. |
| 7,497,037 B2 | 3/2009 | Vick et al. |
| 7,498,856 B2 | 3/2009 | Lin et al. |
| 7,498,956 B2 | 3/2009 | Baier et al. |
| 7,522,970 B2 | 4/2009 | Fernandez |
| 7,552,549 B2 | 6/2009 | Whittlesey et al. |
| 7,579,946 B2 | 8/2009 | Case, Jr. |
| 7,596,891 B2 | 10/2009 | Carnes et al. |
| 7,602,301 B1 | 10/2009 | Stirling et al. |
| 7,607,243 B2 | 10/2009 | Berner, Jr. et al. |
| 7,617,068 B2 | 11/2009 | Tadin et al. |
| 7,623,987 B2 | 11/2009 | Vock et al. |
| 7,625,314 B2 | 12/2009 | Ungari et al. |
| 7,651,442 B2 | 1/2010 | Carlson |
| 7,658,694 B2 | 2/2010 | Ungari |
| 7,670,263 B2 | 3/2010 | Ellis et al. |
| 7,726,206 B2 | 6/2010 | Terrafranca, Jr. et al. |
| 7,739,076 B1 | 6/2010 | Vock et al. |
| 7,758,523 B2 | 7/2010 | Collings et al. |
| 7,771,320 B2 | 8/2010 | Riley et al. |
| 7,805,150 B2 | 9/2010 | Graham et al. |
| 7,816,632 B2 | 10/2010 | Bourke, III et al. |
| 7,840,378 B2 | 11/2010 | Vock et al. |
| 7,901,325 B2 | 3/2011 | Henderson |
| 7,905,815 B2 | 3/2011 | Ellis et al. |
| 7,909,737 B2 | 3/2011 | Ellis et al. |
| 7,921,716 B2 | 4/2011 | Morris Bamberg et al. |
| 7,934,983 B1 | 5/2011 | Eisner |
| 7,997,007 B2 | 8/2011 | Sanabria-Hernandez |
| 8,056,268 B2 | 11/2011 | DiBenedetto et al. |
| 8,061,061 B1 | 11/2011 | Rivas |
| 8,099,258 B2 | 1/2012 | Alten et al. |
| 8,131,498 B1 | 3/2012 | McCauley |
| 8,142,267 B2 | 3/2012 | Adams |
| 8,172,722 B2 | 5/2012 | Molyneux et al. |
| 8,212,158 B2 | 7/2012 | Wiest |
| 8,251,930 B2 | 8/2012 | Ido |
| 8,253,586 B1 | 8/2012 | Matak |
| 8,291,618 B2 | 10/2012 | Ellis |
| 8,333,643 B2 | 12/2012 | Eisner |
| 8,467,979 B2 | 6/2013 | Sobolewski |
| 8,474,153 B2 | 7/2013 | Brie et al. |
| 8,484,654 B2 | 7/2013 | Graham et al. |
| 8,676,541 B2 * | 3/2014 | Schrock .............. A43B 3/00 702/188 |
| 8,739,639 B2 | 6/2014 | Owings et al. |
| 9,089,182 B2 * | 7/2015 | Schrock .............. A43B 3/00 |
| 2001/0003665 A1 | 6/2001 | Kim |
| 2001/0054043 A1 | 12/2001 | Harlan |
| 2002/0035184 A1 | 3/2002 | Plaver et al. |
| 2002/0134153 A1 | 9/2002 | Grenlund |
| 2003/0009308 A1 | 1/2003 | Kirtley |
| 2003/0054327 A1 | 3/2003 | Evensen |
| 2003/0097878 A1 | 5/2003 | Farringdon et al. |
| 2003/0163287 A1 | 8/2003 | Vock et al. |
| 2003/0207718 A1 | 11/2003 | Perlmutter |
| 2004/0154190 A1 | 8/2004 | Munster |
| 2004/0162702 A1 | 8/2004 | Pandipati et al. |
| 2004/0215413 A1 | 10/2004 | Weldum et al. |
| 2004/0218317 A1 | 11/2004 | Kawazu et al. |
| 2004/0225467 A1 | 11/2004 | Vock et al. |
| 2004/0226192 A1 | 11/2004 | Geer et al. |
| 2005/0011085 A1 | 1/2005 | Swigart et al. |
| 2005/0032582 A1 | 2/2005 | Mahajan et al. |
| 2005/0046576 A1 | 3/2005 | Julian et al. |
| 2005/0106977 A1 | 5/2005 | Coulston |
| 2005/0183292 A1 | 8/2005 | DiBenedetto et al. |
| 2005/0188566 A1 | 9/2005 | Whittlesey et al. |
| 2005/0221403 A1 | 10/2005 | Gazenko |
| 2005/0261609 A1 | 11/2005 | Collings et al. |
| 2005/0282633 A1 | 12/2005 | Nicolas et al. |
| 2006/0010174 A1 | 1/2006 | Nguyen et al. |
| 2006/0017692 A1 | 1/2006 | Wehrenberg et al. |
| 2006/0025229 A1 | 2/2006 | Mahajan et al. |
| 2006/0026120 A1 | 2/2006 | Carolan et al. |
| 2006/0091715 A1 | 5/2006 | Schmitz et al. |
| 2006/0143645 A1 | 6/2006 | Vock et al. |
| 2006/0144152 A1 | 7/2006 | Cabuz et al. |
| 2006/0217231 A1 | 9/2006 | Parks et al. |
| 2006/0226843 A1 | 10/2006 | Al-Anbuky et al. |
| 2006/0248749 A1 | 11/2006 | Ellis |
| 2006/0262120 A1 | 11/2006 | Rosenberg |
| 2007/0006489 A1 | 1/2007 | Case et al. |
| 2007/0016091 A1 | 1/2007 | Butt et al. |
| 2007/0026421 A1 | 2/2007 | Sundberg et al. |
| 2007/0032748 A1 | 2/2007 | McNeil et al. |
| 2007/0033838 A1 | 2/2007 | Luce et al. |
| 2007/0060408 A1 | 3/2007 | Schultz et al. |
| 2007/0063849 A1 | 3/2007 | Rosella et al. |
| 2007/0063850 A1 | 3/2007 | Devaul et al. |
| 2007/0067885 A1 | 3/2007 | Fernandez |
| 2007/0068244 A1 | 3/2007 | Billing et al. |
| 2007/0073178 A1 | 3/2007 | Browning et al. |
| 2007/0078324 A1 | 4/2007 | Wijisiriwardana |
| 2007/0082389 A1 | 4/2007 | Clark et al. |
| 2007/0094890 A1 | 5/2007 | Cho et al. |
| 2007/0118328 A1 | 5/2007 | Vock et al. |
| 2007/0143452 A1 | 6/2007 | Suenbuel et al. |
| 2007/0152812 A1 | 7/2007 | Wong et al. |
| 2007/0173705 A1 | 7/2007 | Teller et al. |
| 2007/0208544 A1 | 9/2007 | Kulach et al. |
| 2007/0232455 A1 | 10/2007 | Hanoun |
| 2007/0250286 A1 | 10/2007 | Duncan et al. |
| 2007/0260421 A1 | 11/2007 | Berner et al. |
| 2007/0283599 A1 | 12/2007 | Talbott |
| 2008/0027679 A1 | 1/2008 | Shklarski |
| 2008/0028783 A1 | 2/2008 | Immel et al. |
| 2008/0039203 A1 | 2/2008 | Ackley et al. |
| 2008/0048616 A1 | 2/2008 | Paul et al. |
| 2008/0056508 A1 | 3/2008 | Pierce et al. |
| 2008/0060224 A1 | 3/2008 | Whittlesey et al. |
| 2008/0061023 A1 | 3/2008 | Moor |
| 2008/0066343 A1 | 3/2008 | Sanabria-Hernandez |
| 2008/0066560 A1 | 3/2008 | Yu et al. |
| 2008/0127527 A1 | 6/2008 | Chen |
| 2008/0134583 A1 | 6/2008 | Polus |
| 2008/0165140 A1 | 7/2008 | Christie et al. |
| 2008/0172498 A1 | 7/2008 | Boucard |
| 2008/0177507 A1 | 7/2008 | Mian et al. |
| 2008/0188353 A1 | 8/2008 | Vitolo et al. |
| 2008/0200312 A1 | 8/2008 | Tagliabue |
| 2008/0203144 A1 | 8/2008 | Kim |
| 2008/0218310 A1 | 9/2008 | Alten et al. |
| 2008/0221403 A1 | 9/2008 | Fernandez |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0259028 A1 | 10/2008 | Teepell et al. |
| 2008/0269644 A1 | 10/2008 | Ray |
| 2008/0287832 A1 | 11/2008 | Collins et al. |
| 2008/0293023 A1 | 11/2008 | Diehl et al. |
| 2008/0297832 A1 | 12/2008 | Otsuka |
| 2008/0306410 A1 | 12/2008 | Kalpaxis et al. |
| 2008/0307899 A1 | 12/2008 | Von Lilienfeld-Toal et al. |
| 2008/0318679 A1 | 12/2008 | Tran et al. |
| 2009/0018691 A1 | 1/2009 | Fernandez |
| 2009/0027917 A1 | 1/2009 | Chen et al. |
| 2009/0048538 A1 | 2/2009 | Levine et al. |
| 2009/0061837 A1 | 3/2009 | Chaudhri et al. |
| 2009/0075347 A1 | 3/2009 | Cervin et al. |
| 2009/0075781 A1 | 3/2009 | Schwarzberg et al. |
| 2009/0076341 A1 | 3/2009 | James et al. |
| 2009/0105047 A1 | 4/2009 | Guidi et al. |
| 2009/0107009 A1 | 4/2009 | Bishop et al. |
| 2009/0135001 A1 | 5/2009 | Yuk |
| 2009/0137933 A1 | 5/2009 | Lieberman et al. |
| 2009/0149299 A1 | 6/2009 | Tchao et al. |
| 2009/0150178 A1 | 6/2009 | Sutton et al. |

(56) References Cited

U.S. PATENT DOCUMENTS

| | | |
|---|---|---|
| 2009/0152456 A1 | 6/2009 | Waid et al. |
| 2009/0153369 A1 | 6/2009 | Baier et al. |
| 2009/0153477 A1 | 6/2009 | Saenz |
| 2009/0163287 A1 | 6/2009 | Vald'Via et al. |
| 2009/0167677 A1 | 7/2009 | Kruse et al. |
| 2009/0171614 A1 | 7/2009 | Damen |
| 2009/0259566 A1 | 10/2009 | White, III et al. |
| 2009/0262088 A1 | 10/2009 | Moll-Carrillo et al. |
| 2009/0293319 A1 | 12/2009 | Avni |
| 2009/0297832 A1 | 12/2009 | Hatta et al. |
| 2010/0000121 A1 | 1/2010 | Brodie et al. |
| 2010/0004566 A1 | 1/2010 | Son et al. |
| 2010/0009810 A1 | 1/2010 | Trzecieski |
| 2010/0023231 A1 | 1/2010 | Allgaier et al. |
| 2010/0023531 A1 | 1/2010 | Brisebois et al. |
| 2010/0035688 A1 | 2/2010 | Picunko |
| 2010/0053867 A1 | 3/2010 | Ellis et al. |
| 2010/0056340 A1 | 3/2010 | Ellis et al. |
| 2010/0057951 A1 | 3/2010 | Ellis et al. |
| 2010/0059561 A1 | 3/2010 | Ellis et al. |
| 2010/0062740 A1 | 3/2010 | Ellis et al. |
| 2010/0063778 A1 | 3/2010 | Schrock et al. |
| 2010/0063779 A1 | 3/2010 | Schrock et al. |
| 2010/0065836 A1 | 3/2010 | Lee |
| 2010/0072948 A1 | 3/2010 | Sun et al. |
| 2010/0082735 A1 | 4/2010 | Petersen et al. |
| 2010/0088023 A1 | 4/2010 | Werner |
| 2010/0094147 A1 | 4/2010 | Inan et al. |
| 2010/0111705 A1 | 5/2010 | Sato et al. |
| 2010/0113160 A1 | 5/2010 | Belz et al. |
| 2010/0129780 A1 | 5/2010 | Homsi et al. |
| 2010/0152619 A1 | 6/2010 | Kalpaxis et al. |
| 2010/0184563 A1 | 7/2010 | Molyneux et al. |
| 2010/0184564 A1 | 7/2010 | Molyneux et al. |
| 2010/0191490 A1 | 7/2010 | Martens et al. |
| 2010/0201500 A1 | 8/2010 | Stirling et al. |
| 2010/0201512 A1 | 8/2010 | Stirling et al. |
| 2010/0204616 A1 | 8/2010 | Shears et al. |
| 2010/0225763 A1 | 9/2010 | Vock et al. |
| 2010/0231580 A1 | 9/2010 | Miyasaka |
| 2010/0286601 A1 | 11/2010 | Yodfat et al. |
| 2010/0292599 A1 | 11/2010 | Oleson et al. |
| 2010/0298659 A1 | 11/2010 | McCombie et al. |
| 2010/0312083 A1 | 12/2010 | Southerland |
| 2010/0332188 A1 | 12/2010 | Vock et al. |
| 2011/0003665 A1 | 1/2011 | Burton et al. |
| 2011/0021280 A1 | 1/2011 | Boroda et al. |
| 2011/0087445 A1 | 4/2011 | Sobolewski |
| 2011/0107369 A1 | 5/2011 | O'Brien et al. |
| 2011/0119027 A1 | 5/2011 | Zhu et al. |
| 2011/0119058 A1 | 5/2011 | Berard et al. |
| 2011/0136627 A1 | 6/2011 | Williams |
| 2011/0152695 A1 | 6/2011 | Granqvist et al. |
| 2011/0203390 A1 | 8/2011 | Tao et al. |
| 2011/0208444 A1 | 8/2011 | Solinsky |
| 2012/0041767 A1 | 2/2012 | Hoffman et al. |
| 2012/0050351 A1 | 3/2012 | Dobler et al. |
| 2012/0050529 A1 | 3/2012 | Bentley |
| 2012/0234111 A1 | 9/2012 | Molyneux et al. |
| 2012/0291563 A1 | 11/2012 | Schrock et al. |
| 2012/0291564 A1 | 11/2012 | Amos et al. |
| 2013/0079907 A1 | 3/2013 | Homsi et al. |
| 2013/0190903 A1 | 7/2013 | Balakrishnan et al. |
| 2013/0213145 A1 | 8/2013 | Owings et al. |
| 2014/0033572 A1 | 2/2014 | Steier et al. |
| 2014/0174205 A1 | 6/2014 | Clarke et al. |
| 2014/0222173 A1 | 8/2014 | Giedwoyn et al. |
| 2014/0350435 A1 | 11/2014 | Lam |

FOREIGN PATENT DOCUMENTS

| | | |
|---|---|---|
| CN | 1839724 A | 10/2006 |
| CN | 200977748Y Y | 11/2007 |
| CN | 200994779 Y | 12/2007 |
| CN | 101240461 A | 8/2008 |
| CN | 101242880 A | 8/2008 |
| CN | 101367012 A | 2/2009 |
| CN | 101784230 A | 7/2010 |
| CN | 101890215 A | 11/2010 |
| CN | 101894206 A | 11/2010 |
| CN | 102143695 A | 8/2011 |
| CN | 201948063 U | 8/2011 |
| DE | 3704870 C1 | 4/1988 |
| EP | 0160880 A1 | 11/1985 |
| EP | 0662600 A1 | 7/1995 |
| EP | 1707065 A1 | 10/2006 |
| EP | 2189191 A2 | 5/2010 |
| FR | 2929827 A1 | 10/2009 |
| GB | 251054 A | 4/1926 |
| GB | 2421416 A | 6/2006 |
| JP | 56-64301 | 5/1981 |
| JP | 05-161724 | 6/1993 |
| JP | H06336967 A | 12/1994 |
| JP | 3036281 B2 | 4/2000 |
| JP | 2001351591 A | 12/2001 |
| JP | 2002163404 A | 6/2002 |
| JP | 2003236002 A | 8/2003 |
| JP | 2005156531 A | 6/2005 |
| JP | 2005270640 A | 10/2005 |
| JP | 2007-134473 A | 5/2007 |
| JP | 200715117 | 6/2007 |
| JP | 2008-3752 A | 10/2008 |
| JP | 2009148338 A | 7/2009 |
| JP | 2009-535157 A | 10/2009 |
| JP | 2010088886 A | 4/2010 |
| JP | 2010-517725 A | 5/2010 |
| JP | 2011112938 A | 6/2011 |
| JP | 2011-524207 A | 9/2011 |
| JP | 2011524207 A | 9/2011 |
| JP | 2011196931 A | 10/2011 |
| JP | 2012065942 A | 4/2012 |
| JP | 2012524638 A | 10/2012 |
| KR | 20050032119 | 4/2005 |
| KR | 20060021632 | 3/2006 |
| KR | 20060034353 | 4/2006 |
| KR | 10-2009-0102550 | 9/2009 |
| KR | 20100012845 U | 12/2010 |
| KR | 20100130860 A | 12/2010 |
| KR | 20110071728 A | 6/2011 |
| WO | 9807341 A2 | 2/1998 |
| WO | 0033031 A1 | 6/2000 |
| WO | 0235184 A2 | 5/2002 |
| WO | 2006065679 A2 | 6/2006 |
| WO | 2006091715 A1 | 8/2006 |
| WO | 2007064735 A2 | 6/2007 |
| WO | 2007082389 A1 | 7/2007 |
| WO | 2007128049 A1 | 11/2007 |
| WO | 2007130287 A2 | 11/2007 |
| WO | 2008061023 A2 | 5/2008 |
| WO | 2008101085 A2 | 8/2008 |
| WO | 2008134583 A1 | 11/2008 |
| WO | 2009027917 A1 | 3/2009 |
| WO | 2009126818 A2 | 10/2009 |
| WO | 2009152456 A2 | 12/2009 |
| WO | 2010065836 A2 | 6/2010 |
| WO | 2010065886 A1 | 6/2010 |
| WO | 2010111705 A2 | 9/2010 |
| WO | 2011157607 A1 | 12/2011 |
| WO | 2012061804 A1 | 5/2012 |
| WO | 2012109244 A1 | 8/2012 |
| WO | 2012112931 A2 | 8/2012 |
| WO | 2012143274 A2 | 10/2012 |

OTHER PUBLICATIONS

Aug. 29, 2013—(WO) International Preliminary Report on Patentability App No. PCT/US2012/025713.

Dec. 11, 2009—(WO) ISR and WO App No. PCT/US2009/047246.

Morris, Stacy J., A Shoe-Integrated Sensor System for Wireless Gait Analysis and Real-Time Therapeutic Feedback, dissertation, 2004, pp. 1-314, Massachusetts Institute of Technology, MA.

Aug. 21, 2012—(WO) ISR and WO—App. No. PCT/US2012/025717.

(56) References Cited

OTHER PUBLICATIONS

Jul. 11, 2012—(WO) ISR & WO App No. PCT/US2012/025709.
May 28, 2013—(WO) ISR & WO App No. PCT/US2013/027421.
Fleming et al, Athlete and Coach Perceptions of Technology Needs for Evaluating Running Performance, article, Aug. 14, 2010, 18 pages, 13:1-18, UK.
Salpavaara, et al. Wireless Insole Sensor System for Plantar Force Measurements during Sports Events, article, Sep. 6-11, 2009, XIX IMEKO World Congress, Fundamental and Applied Metrology, 6 pages, Lisbon, Portugal.
Mar. 7, 2012—(WO) ISR and WO—App. PCT/US2011/060187.
Jul. 15, 2013—(WO) Search Report and Written Opinion—App. No. PCT/US2013/022219.
Lovell, "A system for real-time gesture recognition and classification of coordinated motion," Massachusetts Institute of Technology, Dept. of Electrical Engineering and Computer Science, 2005, <http://dspace.mit.edu/handle/1721.1/33290> (2 pages).
Chee et al, "A low cost wearable wireless sensing system for upper limb home rehabilitation," Robotics Automation and Mechatronics (RAM) 2010 IEEE Conference on Jun. 28-30, 2010; Abstract printout (1 page).
Guraliuc et al., "Channel model for on the body communication along and around the human torso at 2.4Ghz and 5.8Ghz," Antenna Technology (IWAT), 2010 International Workshop on Mar. 1-3, 2010; Abstract printout (1 page).
Jun. 21, 2012—(WO) ISR—App No. PCT/US2012/025701.
Frazier, Karen, "How Many Calories to 1 Carb?" published Nov. 12, 2010, Livestrong.com, 3 pages.
Oct. 1, 2013—(WO) ISR and WO—App No. PCT/US2013/048157.
Llosa et al., "Design of a Motion Detector to Monitor Rowing Performance Based on Wireless Sensor Networks," Intelligent Networking and Collaborativge Systems, 2009, http://ieeexplore.ieee.org/xpl/freeabs_all.jsp?arnumber=5369324 (1 page).
Choquette et al., "Accelerometer-based wireless body area network to estimate intensity of therapy in post-acute rehabilitation," Journal of NeuroEngineering and Rehabilitation 2008, http://www.jneuroengrehab.com/content/5/1/20/abstract (1 page).
Morris, "A shoe-integrated sensor system for wireless gait analysis and real-time therapeutic feedback," Harvard-MIT Division of Health Sciences and Technology, 2004,http://dspace.mitedu/handle/1721.1/28601 (3 pages).
Lapinski, "A wearable, wireless sensor system for sports medicine," Massachusetts Institute of Technology, School of Architecture and Planning, Program in Media Arts and Sciences, 2008, http://dspace.mit.edulhandle/1721.1/46581(3 pages).
Aylward, "Sensemble : a wireless inertial sensor system for the interactive dance and collective motion analysis," Massachusetts Institute of Technology, School of Architecture and Planning, Program in Media Arts and Sciences, 2006, http://dspace.mitedu/handle/1721.1/37391 (3 pages).
Danko; How to Work a Nike Sensor; Dec. 26, 2010; eHow website; 4 pages.
Coyne; Stout's Shoes on Mass Ave Oldest Shoe Store in the USA; Jun. 18, 2013; FunCityFinder website; 5 pages.
Davis, The Re-emergence of the Minimal Running Shoe, Clinical Commentary, Journal of Orthopaedic & Sports Physical Therapy, vol. 44, No. 10, pp. 775-784, Oct. 2014.
Lim, Joo-Tack, STO Ltd., Final Report on IT development cooperative project, "Development of IT running shoes that an transmit athletic information of the shoes when running and development of receiver technology," Ministry of Knowledge Economy (Institute for Information Technology Advancement (ITA)) (Jun. 30, 2009).
Aug. 8, 2016—(EP) Extended Search Report—App. No. 16170589.2.
Sep. 1, 2016—(EP) Extended Search Report—App. No. 16167470.0.

\* cited by examiner

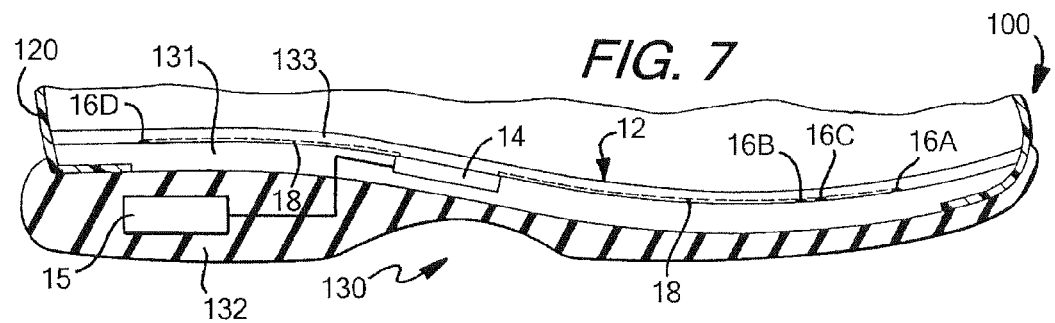
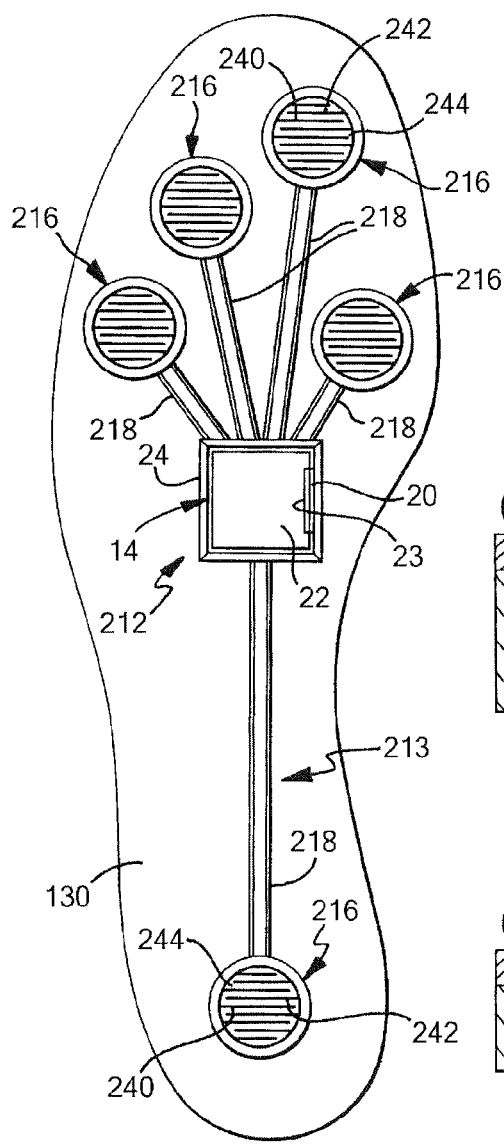
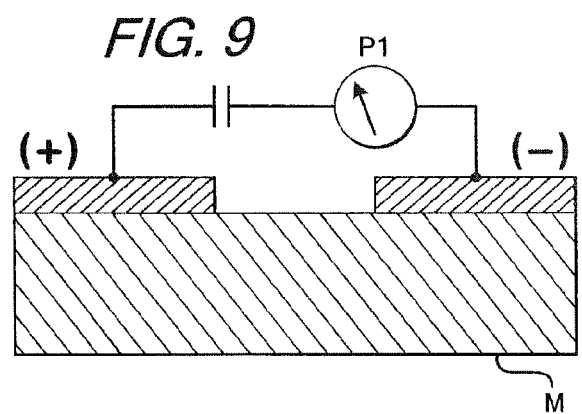
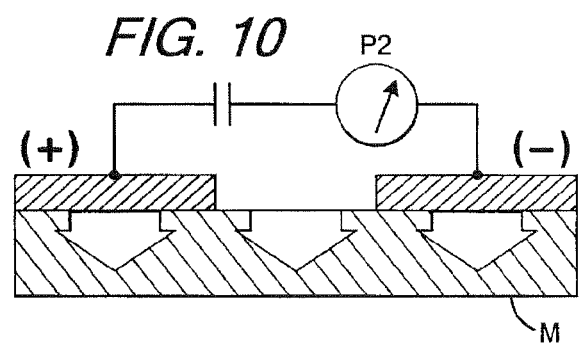

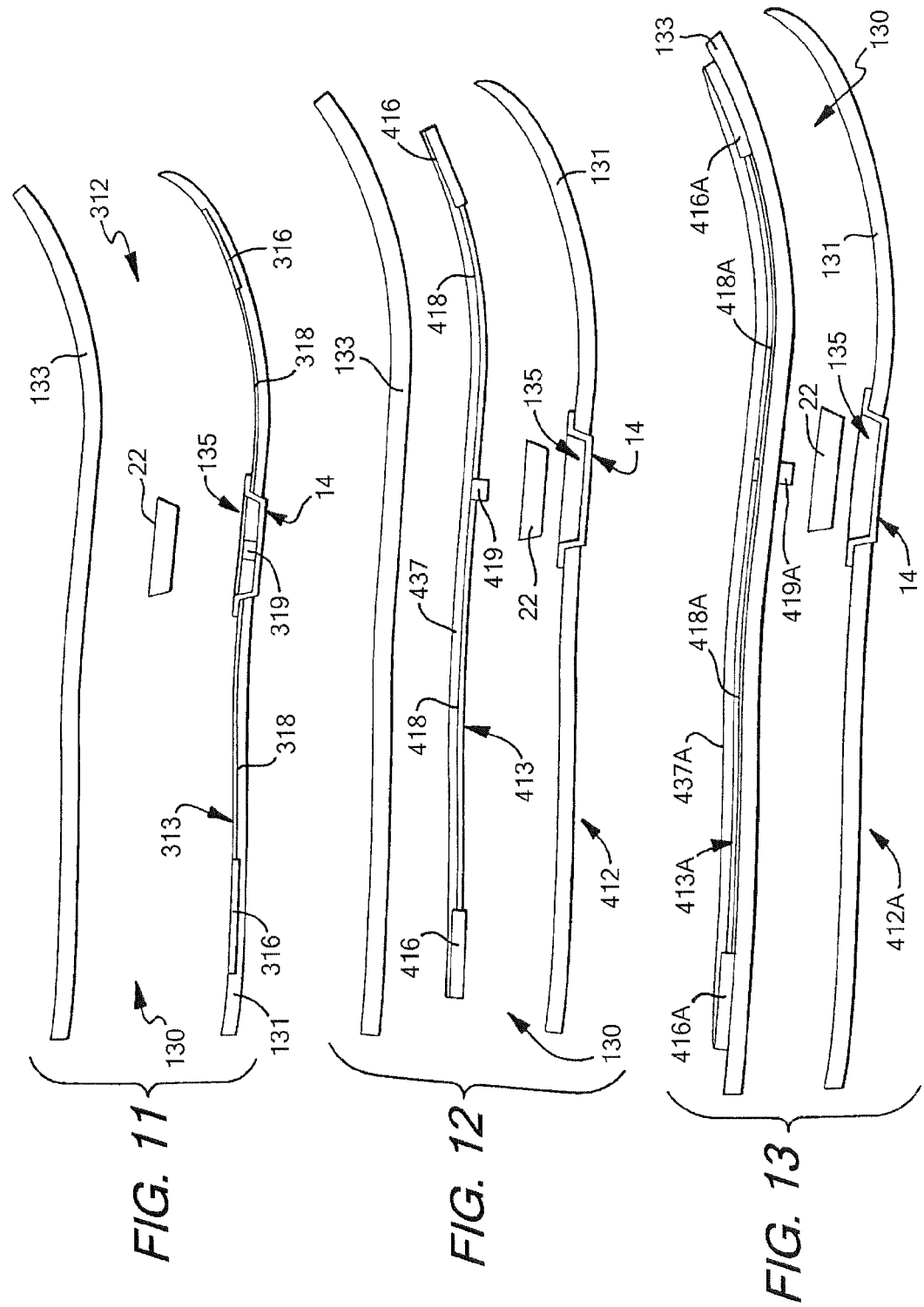

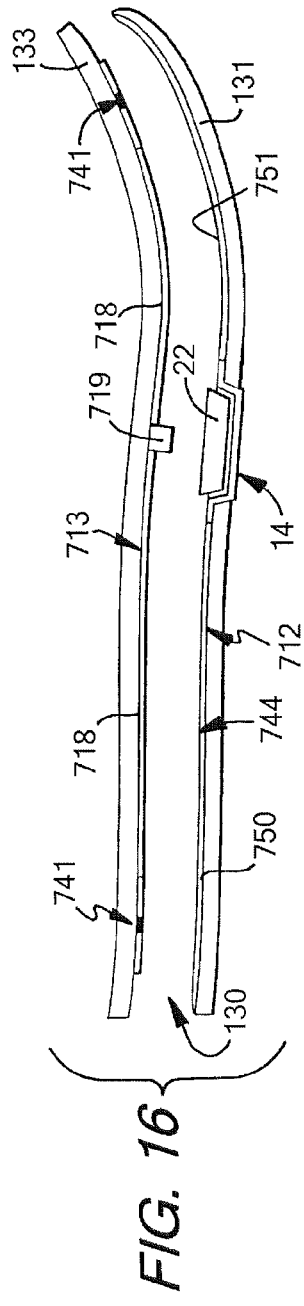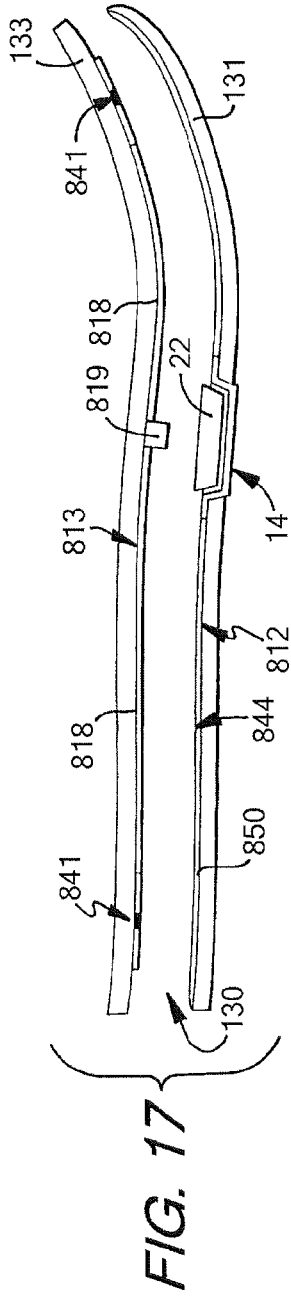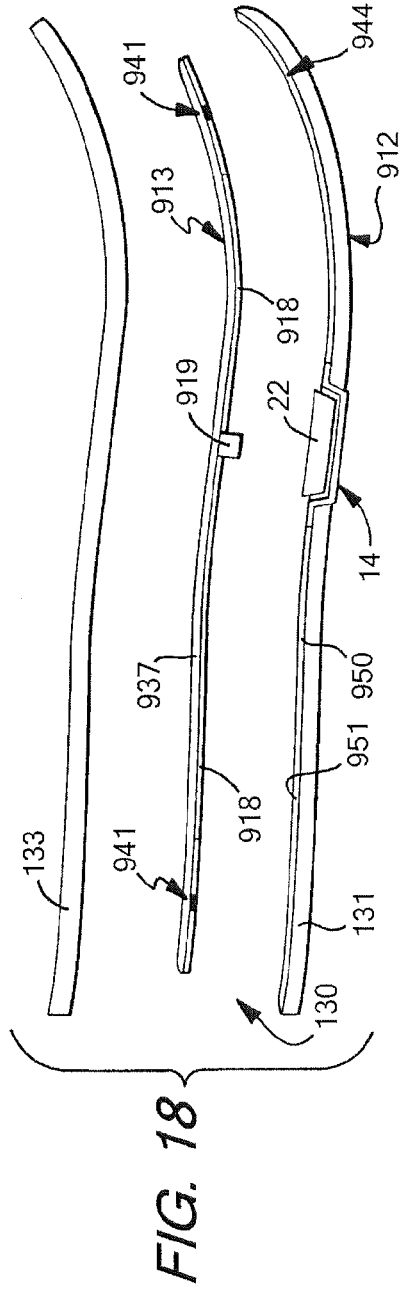

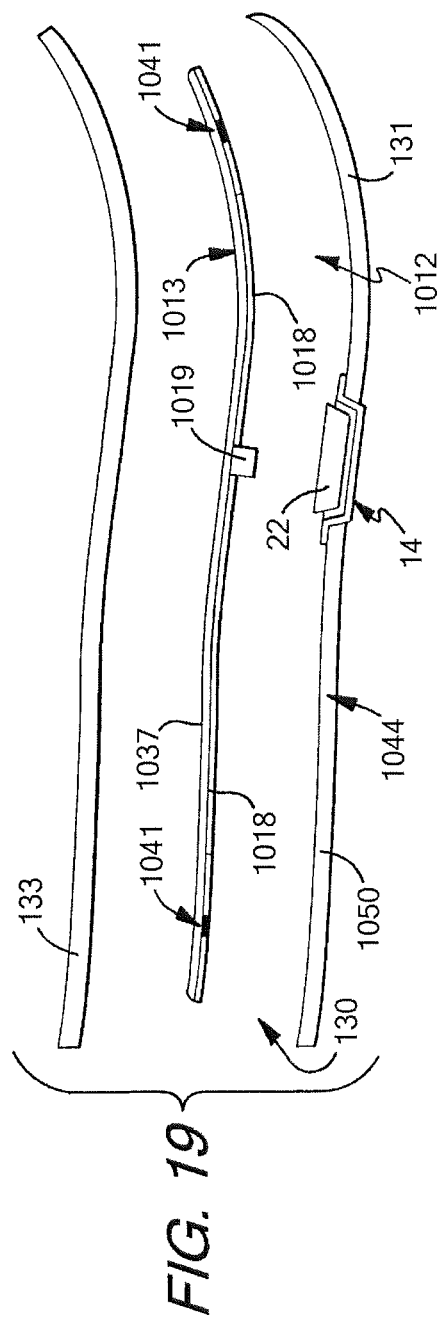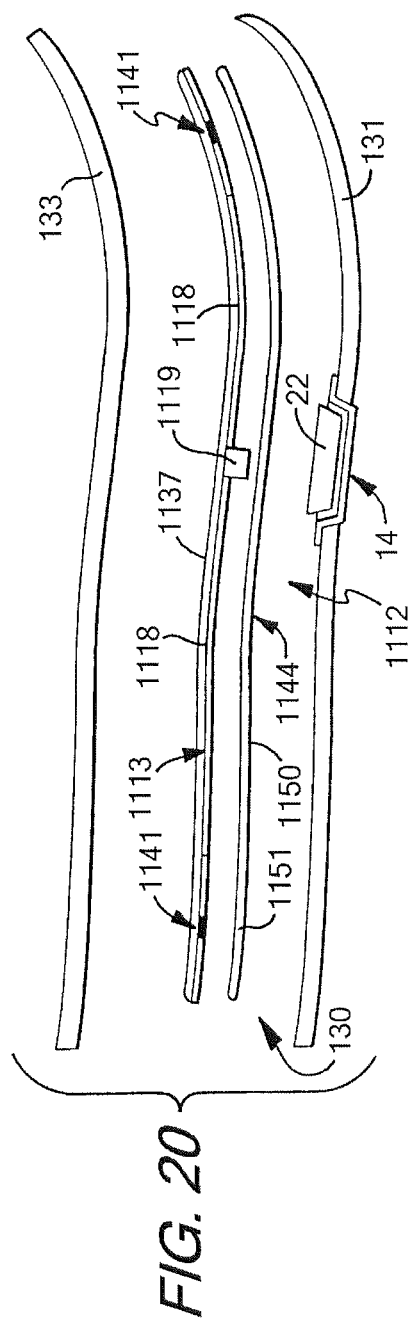

FOOTWEAR HAVING SENSOR SYSTEM

CROSS-REFERENCE TO RELATED APPLICATIONS

The present application is a continuation of U.S. patent application Ser. No. 13/399,778, filed Feb. 17, 2012, which is a continuation-in-part of U.S. patent application Ser. No. 12/483,824, filed Jun. 12, 2009, and U.S. patent application Ser. No. 12/483,828, filed Jun. 12, 2009, both of which claim priority to U.S. Provisional Patent Application No. 61/061,427, filed on Jun. 13, 2008, and U.S. Provisional Patent Application No. 61/138,048, filed on Dec. 16, 2008, and U.S. patent application Ser. No. 13/399,778 also claims priority to U.S. Provisional Application No. 61/443,911, filed Feb. 17, 2011, and the present application claims priority to all of such prior applications, which are all incorporated herein by reference in their entireties.

TECHNICAL FIELD

The present invention generally relates to footwear having a sensor system and, more particularly, to a shoe having a force sensor assembly operably connected to a communication port located in the shoe.

BACKGROUND

Shoes having sensor systems incorporated therein are known. Sensor systems collect performance data wherein the data can be accessed for later use such as for analysis purposes. In certain systems, the sensor systems are complex or data can only be accessed or used with certain operating systems. Thus, uses for the collected data can be unnecessarily limited. Accordingly, while certain shoes having sensor systems provide a number of advantageous features, they nevertheless have certain limitations. The present invention seeks to overcome certain of these limitations and other drawbacks of the prior art, and to provide new features not heretofore available.

BRIEF SUMMARY

The present invention relates generally to footwear having a sensor system. Aspects of the invention relate to an article of footwear that includes an upper member and a sole structure, with a sensor system connected to the sole structure. The sensor system includes a plurality of sensors that are configured for detecting forces exerted by a user's foot on the sensor.

According to one aspect, the footwear further contains a communication port operably connected with the sensors. In one embodiment, the communication port is configured for transmitting data regarding forces detected by each sensor in a universally readable format. The port may also be configured for connection to an electronic module to allow communication between the sensors and the module.

According to another aspect, the footwear contains an electronic module in communication with the sensors, which is configured for collecting data from the sensors. The module may be connected with the sensors through the communication port, and may be positioned within a cavity in the footwear. In one embodiment, the module is further configured for transmitting the data to an external device for further processing.

According to another aspect, the footwear may contain a well located in the sole structure that is configured for removably receiving an electronic module. The well may have a communication port connected with the sensors and configured for communication with the module.

According to another aspect, the sensor system further includes a plurality of sensor leads connecting the sensors to the port and/or the electronic module. The leads may also include one or more power leads for supplying power from the port and/or the module to the sensors.

According to a further aspect, the sensors may be one or more various types of sensors. In one embodiment, the sensors are force-sensitive resistor sensors. In another embodiment, the sensors include two electrodes with a force-sensitive resistive material disposed between the electrodes. The electrodes and the force-sensitive material may be disposed on separate members of the sole structure.

According to yet another aspect, the sensor system includes a first sensor located in the first phalange area of the sole structure, a second sensor located in the first metatarsal head area of the sole structure, a third sensor located in the fifth metatarsal head area of the sole structure, and a fourth sensor located in the heel area of the sole structure.

Other aspects of the invention relate to an insert member that may contain a sensor system as described above. The insert member is adapted to be placed in contact with the sole structure, such as by inserting the insert member into the article of footwear and/or forming the insert member as a part of the article of footwear, such as a portion of the sole structure of the article of footwear. For example, the insert may be an insole member, a portion of the midsole, or a separate member adapted to be inserted beneath or above the insole member, among other configurations.

According to one aspect, the insert is formed of the insert member that includes a central portion adapted to be engaged by a metatarsal portion of the foot, a first phalange portion extending from a front edge of the central portion and adapted to be engaged by a first phalange of the foot, and a heel portion extending from a rear edge of the central portion and adapted to be engaged by a heel of the foot. The central portion has a length measured from the front edge to the rear edge and a width measured perpendicular to the length, and wherein the first phalange portion extends from the front edge of the central portion in an elongated manner and has a width that is narrower than the width of the central portion and a length that is greater than the width of the first phalange portion. The heel portion extends from the rear edge of the central portion in an elongated manner and has a width that is narrower than the width of the central portion and a length that is greater than the width of the heel portion. The insert also includes a sensor system comprising a plurality of force sensors connected to the insert member and a port configured for communication with an electronic device. At least one of the force sensors is positioned on the central portion, at least one of the force sensors is positioned on the first phalange portion, and at least one of the force sensors is positioned on the heel portion, and the port is positioned on the central portion. The insert member may have a peripheral edge that includes a front medial edge having an outwardly-curved shape, a front lateral edge having an inwardly-curved shape, and a rear medial edge and a rear lateral edge each having at least one inwardly-curved edge.

According to another aspect, the insert may include a flexible polymer insert member adapted to be placed in contact with the sole structure of the article of footwear and a sensor system comprising a plurality of force sensors connected to the insert member and a port configured for communication with an electronic device. The insert member has a plurality of slits extending completely through the thickness of the insert member, with the slits positioned proximate at least one of the force sensors of the sensor system. At least one of the slits may extend from the peripheral edge inwardly into the insert member, and/or may be positioned completely within the insert member and so as to not contact the peripheral edge. In one embodiment, at least one of the sensors has an internal gap, and one of the slits extends into the internal gap. In another embodiment, the insert member comprises a first layer having the electrodes and leads located thereon and a second layer having the force sensitive resistive material thereon.

According to a further aspect, the insert may include a sensor system comprising a plurality of force sensors connected to the insert member and a port configured for communication with an electronic device. At least one of the force sensors includes a patch of force-sensitive resistive material, a first electrode having a first lead connected to the port; and a second electrode having a second lead connected to the port. The patch of force-sensitive resistive material has a multi-lobed structure includes at least a first lobe and a second lobe separated by a gap. The first electrode is in contact with the first lobe and the second lobe, and the second electrode is in contact with the first lobe and the second lobe. The patch of force-sensitive material may also include one or more additional lobes in contact with the electrodes, such as a third lobe separated from the first lobe by a second gap. The patch of force-sensitive resistive material may also include one or more narrow bridge members spanning the gap and connecting the first lobe and the second lobe. The electrodes may also each have an enlarged space that is superimposed over the elongated gap between the first and second lobes, such that no portion of the electrodes are positioned within the elongated gap.

According to yet another aspect, the insert may include an insert member, a graphic layer formed of a sheet of material connected to a surface of the insert member in a layered configuration, the sheet of material having a graphic design thereon, and a sensor system containing a plurality of force sensors connected to the insert member and a port configured for communication with an electronic device.

Additional aspects of the invention relate to a foot contacting member or other sole member of the sole structure that has a sensor system as described above, including a plurality of sensors, connected thereto. The foot contacting member or other sole member may be configured for insertion into an article of footwear. In one embodiment, the sole member may include a plurality of electrodes and sensor leads configured to be connected to a force-sensitive material disposed on another sole member.

Further aspects of the invention relate to a system that includes an article of footwear with a sensor system as described above, with an electronic module connected to the sensor system, and an external device configured for communication with the electronic module. The module is configured to receive data from the sensors and to transmit the data to the external device, and the external device is configured for further processing the data.

According to one aspect, the system also includes an accessory device connected to the external device, configured to enable communication between the electronic module and the external device. The accessory device may also be configured for connection to a second external device to enable communication between the electronic module and the second external device.

According to another aspect, the data communicated to the external device can be used in one or more different applications. Such applications can include using the data as control input for a program executed by the external device, such as a game program, or for athletic performance monitoring, among other applications. Athletic performance monitoring can include monitoring one or more performance metrics such as speed, distance, lateral movement, acceleration, jump height, weight transfer, foot strike pattern, balance, foot pronation or supination, loft time measurement during running, lateral cutting force, contact time, center of pressure, weight distribution, and/or impact force, among others.

Still further aspects of the invention relate to methods utilizing an article of footwear containing a sensor system as described above. Such methods can include receiving data from the sensors at the electronic module and transmitting the data from the module to a remote external device for further processing, which may include use in one or more applications. Such methods can also include removing or disconnecting a first electronic module from the sensor system and connecting a second module in its place, where the second module is configured for a different operation. Such methods can further include processing the data for use in one or more applications and/or using the data as control input for an external device. Aspects of the invention may also include computer-readable media containing instructions for use in performing one or more features of these methods and/or utilizing the footwear and systems described above.

Other aspects of the invention relate to a system that includes at least two articles of footwear, each having a sensor system as described above, with an electronic module connected thereto, where each electronic module is configured for communicating data received from the sensors to an external device. The system may use several communication modes. In one embodiment, each module communicates separately with the external device. In another embodiment, the modules are additionally or alternately configured to communicate with each other. In a further embodiment, one electronic module is configured to transmit the data to the other electronic module, and the other electronic module is configured to transmit the data from both electronic modules to the external device.

Still other features and advantages of the invention will be apparent from the following specification taken in conjunction with the following drawings.

BRIEF DESCRIPTION OF THE DRAWINGS

FIG. 7 is a side cross-sectional view of a sole of a shoe incorporating the sensor system of FIG. 3, including an external output port;

FIG. 8 is a top view of a sole of a shoe incorporating another embodiment of a sensor system utilizing force-sensitive resistor (FSR) sensors;

FIGS. 9 and 10 are schematic views illustrating force-sensitive resistive behavior of a force-sensitive resistive material;

FIGS. 11-14 are side cross-sectional exploded views of soles of a shoe incorporating embodiments of sensor systems utilizing force-sensitive resistor (FSR) sensors;

FIGS. 16-20 are side cross-sectional exploded views of soles of a shoe incorporating embodiments of sensor systems utilizing separate electrodes and a force-sensitive resistive element;

DETAILED DESCRIPTION

Figure 1:
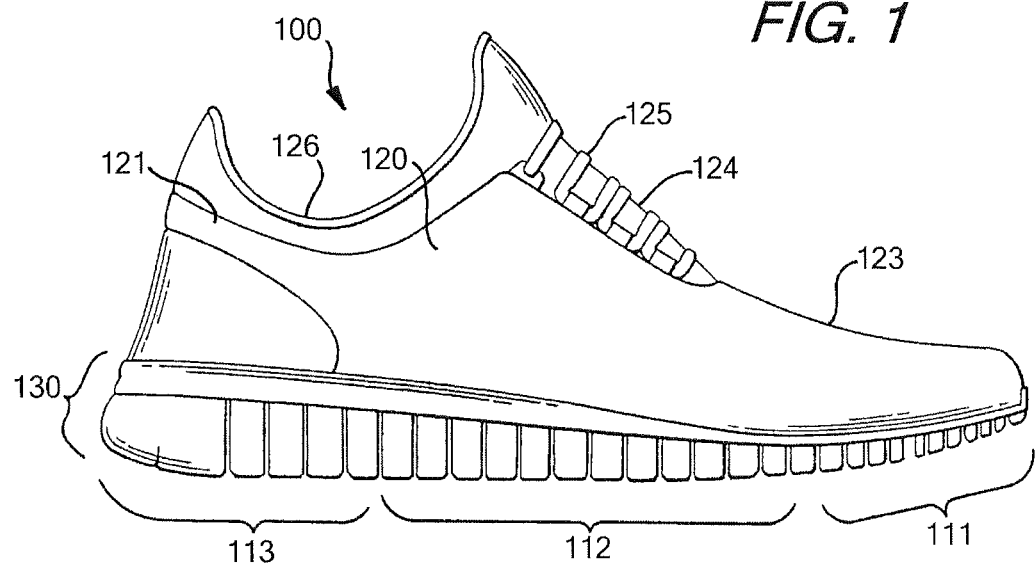
FIG. 1 is a side view of a shoe.

While this invention is susceptible of embodiment in many different forms, there are shown in the drawings, and will herein be described in detail, preferred embodiments of the invention with the understanding that the present disclosure is to be considered as an exemplification of the principles of the invention and is not intended to limit the broad aspects of the invention to the embodiments illustrated and described.

Figure 2:
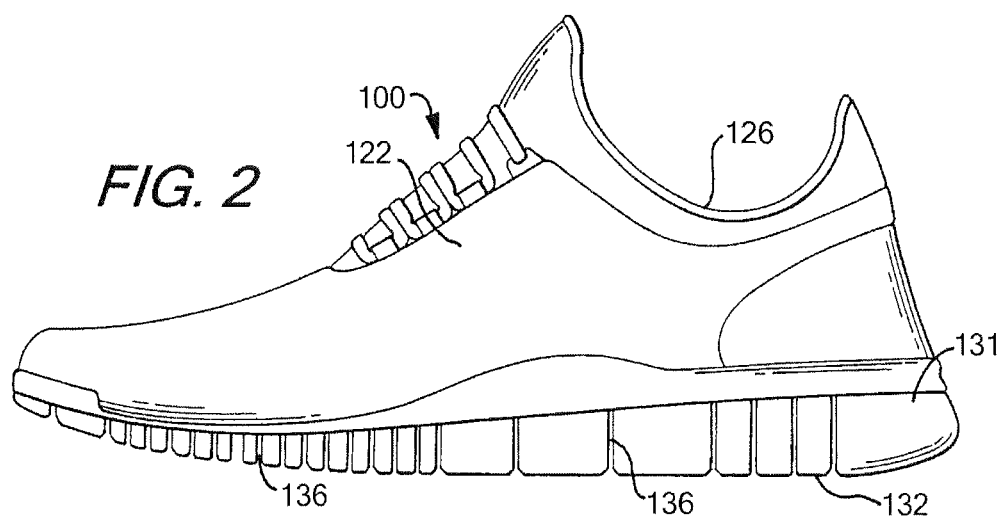
FIG. 2 is an opposed side view of the shoe of FIG. 1.

Footwear, such as a shoe, is shown as an example in FIGS. 1-2 and generally designated with the reference numeral 100. The footwear 100 can take many different forms, including, for example, various types of athletic footwear. In one exemplary embodiment, the shoe 100 generally includes a force sensor system 12 operably connected to a universal communication port 14. As described in greater detail below, the sensor system 12 collects performance data relating to a wearer of the shoe 100. Through connection to the universal communication port 14, multiple different users can access the performance data for a variety of different uses as described in greater detail below.

An article of footwear 100 is depicted in FIGS. 1-2 as including an upper 120 and a sole structure 130. For purposes of reference in the following description, footwear 100 may be divided into three general regions: a forefoot region 111, a midfoot region 112, and a heel region 113, as illustrated in FIG. 1. Regions 111-113 are not intended to demarcate precise areas of footwear 100. Rather, regions 111-113 are intended to represent general areas of footwear 100 that provide a frame of reference during the following discussion. Although regions 111-113 apply generally to footwear 100, references to regions 111-113 also may apply specifically to upper 120, sole structure 130, or individual components included within and/or formed as part of either upper 120 or sole structure 130.

As further shown in FIGS. 1 and 2, the upper 120 is secured to sole structure 130 and defines a void or chamber for receiving a foot. For purposes of reference, upper 120 includes a lateral side 121, an opposite medial side 122, and a vamp or instep area 123. Lateral side 121 is positioned to extend along a lateral side of the foot (i.e., the outside) and generally passes through each of regions 111-113. Similarly, medial side 122 is positioned to extend along an opposite medial side of the foot (i.e., the inside) and generally passes through each of regions 111-113. Vamp area 123 is positioned between lateral side 121 and medial side 122 to correspond with an upper surface or instep area of the foot. Vamp area 123, in this illustrated example, includes a throat 124 having a lace 125 or other desired closure mechanism that is utilized in a conventional manner to modify the dimensions of upper 120 relative the foot, thereby adjusting the fit of footwear 100. Upper 120 also includes an ankle opening 126 that provides the foot with access to the void within upper 120. A variety of materials may be used for constructing upper 120, including materials that are conventionally utilized in footwear uppers. Accordingly, upper 120 may be formed from one or more portions of leather, synthetic leather, natural or synthetic textiles, polymer sheets, polymer foams, mesh textiles, felts, non-woven polymers, or rubber materials, for example. The upper 120 may be formed from one or more of these materials wherein the materials or portions thereof are stitched or adhesively bonded together, e.g., in manners that are conventionally known and used in the art.

Upper 120 may also include a heel element (not shown) and a toe element (not shown). The heel element, when present, may extend upward and along the interior surface of upper 120 in the heel region 113 to enhance the comfort of footwear 100. The toe element, when present, may be located in forefoot region 111 and on an exterior surface of upper 120 to provide wear-resistance, protect the wearer's toes, and assist with positioning of the foot. In some embodiments, one or both of the heel element and the toe element may be absent, or the heel element may be positioned on an exterior surface of the upper 120, for example. Although the configuration of upper 120 discussed above is suitable for footwear 100, upper 120 may exhibit the configuration of any desired conventional or non-conventional upper structure without departing from this invention.

Sole structure 130 is secured to a lower surface of upper 120 and may have a generally conventional shape. The sole structure 130 may have a multipiece structure, e.g., one that includes a midsole 131, an outsole 132, and a foot contacting member 133, which may be a sockliner, a strobel, an insole member, a bootie element, a sock, etc. (See FIGS. 4-5). In the embodiment shown in FIGS. 4-5, the foot contacting member 133 is an insole member or sockliner. The term "foot contacting member," as used herein does not necessarily imply direct contact with the user's foot, as another element may interfere with direct contact. Rather, the foot contacting member forms a portion of the inner surface of the foot-receiving chamber of an article of footwear. For example, the user may be wearing a sock that interferes with direct contact. As another example, the sensor system 12 may be incorporated into an article of footwear that is designed to slip over a shoe or other article of footwear, such as an external bootie element or shoe cover. In such an article, the upper portion of the sole structure may be considered a foot contacting member, even though it does not directly contact the foot of the user.

Midsole member 131 may be an impact attenuating member. For example, the midsole member 131 may be formed of polymer foam material, such as polyurethane, ethylvinylacetate, or other materials (such as phylon, phylite, etc.) that compress to attenuate ground or other contact surface reaction forces during walking, running, jumping, or other activities. In some example structures according to this invention, the polymer foam material may encapsulate or include various elements, such as a fluid-filled bladder or moderator, that enhance the comfort, motion-control, stability, and/or ground or other contact surface reaction force attenuation properties of footwear 100. In still other example structures, the midsole 131 may include additional elements that compress to attenuate ground or other contact surface reaction forces. For instance, the midsole may include column type elements to aid in cushioning and absorption of forces.

Outsole 132 is secured to a lower surface of midsole 131 in this illustrated example footwear structure 100 and is formed of a wear-resistant material, such as rubber or a flexible synthetic material, such as polyurethane, that contacts the ground or other surface during ambulatory or other activities. The material forming outsole 132 may be manufactured of suitable materials and/or textured to impart enhanced traction and slip resistance. The structure and methods of manufacturing the outsole 132 will be discussed further below. A foot contacting member 133 (which may be an insole member, a sockliner, a bootie member, a strobel, a sock, etc.) is typically a thin, compressible member that may be located within the void in upper 120 and adjacent to a lower surface of the foot (or between the upper 120 and midsole 131) to enhance the comfort of footwear 100. In some arrangements, an insole or sockliner may be absent, and in other embodiments, the footwear 100 may have a foot contacting member positioned on top of an insole or sockliner.

The outsole 132 shown in FIGS. 1 and 2 includes a plurality of incisions or sipes 136 in either or both sides of the outsole 132. These sipes 136 may extend from the bottom of the outsole 132 to an upper portion thereof or to the midsole 131. In one arrangement, the sipes 136 may extend from a bottom surface of the outsole 132 to a point halfway between the bottom of the outsole 132 and the top of the outsole 132. In another arrangement, the sipes 136 may extend from the bottom of the outsole 132 to a point greater than halfway to the top of the outsole 132. In yet another arrangement, the sipes 136 may extend from the bottom of the outsole 132 to a point where the outsole 132 meets the midsole 131. The sipes 136 may provide additional flexibility to the outsole 132, and thereby allow the outsole to more freely flex in the natural directions in which the wearer's foot flexes. In addition, the sipes 136 may aid in providing traction for the wearer. It is understood that embodiments of the present invention may be used in connection with other types and configurations of shoes, as well as other types of footwear and sole structures.

Figure 3:
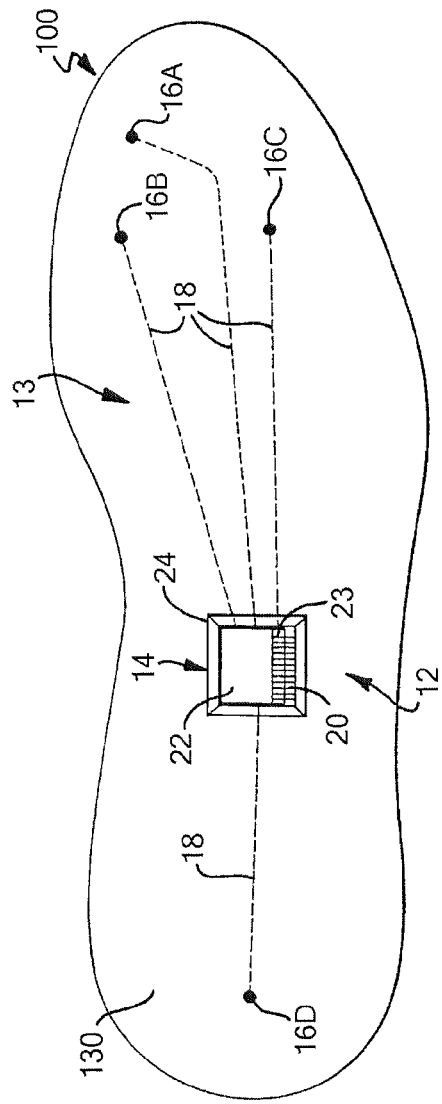
FIG. 3 is a top view of a sole of a shoe incorporating one embodiment of a sensor system.
Figure 4:
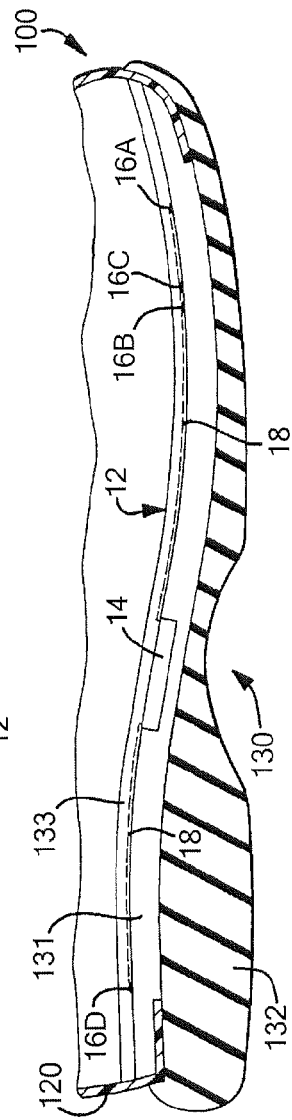
FIG. 4 is a side cross-sectional view of a shoe incorporating the sensor system of FIG. 3.
Figure 5:
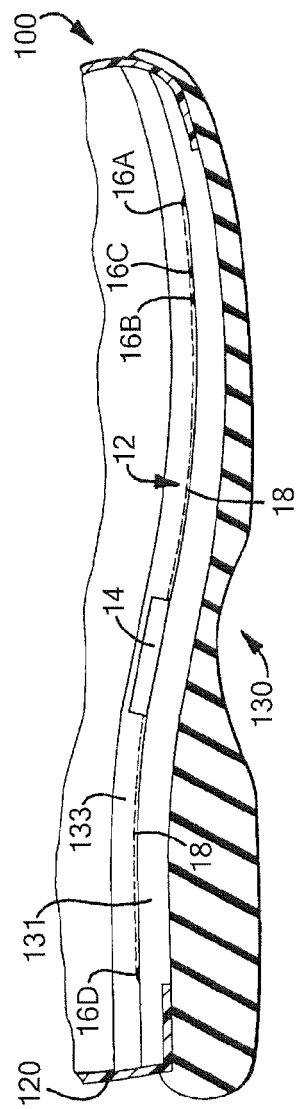
FIG. 5 is a side cross-sectional view of another shoe incorporating the sensor system of FIG. 3.

FIGS. 3-5 illustrate exemplary embodiments of the footwear 100 incorporating a sensor system 12 in accordance with the present invention. The sensor system 12 includes a force sensor assembly 13, having a plurality of sensors 16, and a communication or output port 14 in communication with the sensor assembly 13 (e.g., electrically connected via conductors). In the embodiment illustrated in FIG. 3, the system 12 has four sensors 16: a first sensor 16A at the big toe (first phalange) area of the shoe, two sensors 16B-C at the forefoot area of the shoe, including a second sensor 16B at the first metatarsal head region and a third sensor 16C at the fifth metatarsal head region, and a fourth sensor 16D at the heel. These areas of the foot typically experience the greatest degree of pressure during movement. The embodiment described below and shown in FIGS. 27-28 utilizes a similar configuration of sensors 16. Each sensor 16 is configured for detecting a force exerted by a user's foot on the sensor 16. The sensors communicate with the port 14 through sensor leads 18, which may be wire leads and/or another electrical conductor or suitable communication medium. For example, in one embodiment, the sensor leads 18 may be an electrically conductive medium printed on the foot contacting member 133, the midsole member 131, or another member of the sole structure 130, such as a layer between the foot contacting member 133 and the midsole member 131.

Other embodiments of the sensor system 12 may contain a different number or configuration of sensors 16, such as the embodiments described below and shown in FIGS. 8, 11-21, and 27-28 and generally include at least one sensor 16. For example, in one embodiment, the system 12 includes a much larger number of sensors, and in another embodiment, the system 12 includes two sensors, one in the heel and one in the forefoot of the shoe 100. In addition, the sensors 16 may communicate with the port 14 in a different manner, including any known type of wired or wireless communication, including Bluetooth and near-field communication. A pair of shoes may be provided with sensor systems 12 in each shoe of the pair, and it is understood that the paired sensor systems may operate synergistically or may operate independently of each other, and that the sensor systems in each shoe may or may not communicate with each other. The communication of the sensor systems 12 is described in greater detail below. It is understood that the sensor system 12 may be provided with computer programs/algorithms to control collection and storage of data (e.g., pressure data from interaction of a user's foot with the ground or other contact surface), and that these programs/algorithms may be stored in and/or executed by the sensors 16, the port 14, the module 22, and/or the external device 110. The sensors 16 may include necessary components (e.g. a processor, memory, software, TX/RX, etc.) in order to accomplish storage and/or execution of such computer programs/algorithms and/or direct (wired or wireless) transmission of data and/or other information to the port 14 and/or the external device 110.

The sensor system 12 can be positioned in several configurations in the sole 130 of the shoe 100. In the examples shown in FIGS. 4-5, the port 14, the sensors 16, and the leads 18 can be positioned between the midsole 131 and the foot contacting member 133, such as by connecting the port 14, the sensors 16, and/or the leads 18 to the top surface of the midsole 131 or the bottom surface of the foot contacting member 133. A cavity or well 135 can be located in the midsole 131 (FIG. 4) or in the foot contacting member 133 (FIG. 5) for receiving an electronic module, as described below, and the port 14 may be accessible from within the well 135. In the embodiment shown in FIG. 4, the well 135 is formed by an opening in the upper major surface of the midsole 131, and in the embodiment shown in FIG. 5, the well 135 is formed by an opening in the lower major surface of the foot contacting member 133. The well 135 may be located elsewhere in the sole structure 130 in other embodiments. For example, the well 135 may be located partially within both the foot contacting member 133 and the midsole member 131 in one embodiment, or the well 135 may be located in the lower major surface of the midsole 131 or the upper major surface of the foot contacting member 133. In a further embodiment, the well 135 may be located in the outsole 132 and may be accessible from outside the shoe 100, such as through an opening in the side, bottom, or heel of the sole 130. In the configurations illustrated in FIGS. 4-5, the port 14 is easily accessible for connection or disconnection of an electronic module, as described below. In other embodiments, the sensor system 12 can be positioned differently. For example, in one embodiment, the port 14, the sensors 16, and/or the leads 18 can be positioned within the outsole 132, midsole 131, or foot contacting member 133. In one exemplary embodiment, the port 14, the sensors 16, and/or the leads 18 may be positioned within a foot contacting member 133 positioned above the foot contacting member 133, such as a sock, sockliner, interior footwear bootie, or other similar article. In a further embodiment, the port 14, the sensors 16, and/or the leads 18 can be formed into an insert or a liner, designed to be quickly and easily insertable between the foot contacting member 133 and the midsole 131, such as shown in FIGS. 12 and 19-20. Still other configurations are possible, and some examples of other configurations are described below. As discussed, it is understood that the sensor system 12 may be included in each shoe in a pair.

In one embodiment, the sensors 16 are force sensors for measuring stress, compression, or other force and/or energy exerted on or otherwise associated with the sole 130, particularly during use of the footwear 100. For example, the sensors 16 may be or comprise force-sensitive resistor (FSR) sensors or other sensors utilizing a force-sensitive resistive material (such as a quantum tunneling composite, a custom conductive foam, or a force-transducing rubber, described in more detail below), magnetic resistance sensors, piezoelectric or piezoresistive sensors, strain gauges, spring based sensors, fiber optic based sensors, polarized light sensors, mechanical actuator based sensors, displacement based sensors, and/or any other types of known sensors or switches capable of measuring force and/or compression of the foot contacting member 133, midsole 131, outsole 132, etc. A sensor may be or comprise an analog device or other device that is capable of detecting or measuring force quantitatively, or it may simply be a binary-type ON/OFF switch (e.g., a silicone membrane type switch). It is understood that quantitative measurements of force by the sensors may include gathering and transmitting or otherwise making available data that can be converted into quantitative force measurements by an electronic device, such as the module 22 or the external device 110. Some sensors as described herein, such as piezo sensors, force-sensitive resistor sensors, quantum tunneling composite sensors, custom conductive foam sensors, etc., can detect or measure differences or changes in resistance, capacitance, or electric potential, such that the measured differential can be translated to a force component. A spring-based sensor, as mentioned above, can be configured to measure deformation or change of resistance caused by pressure and/or deformation. A fiber optic based sensor, as described above, contains compressible tubes with a light source and a light measurement device connected thereto. In such a sensor, when the tubes are compressed, the wavelength or other property of light within the tubes changes, and the measurement device can detect such changes and translate the changes into a force measurement. Nanocoatings could also be used, such as a midsole dipped into conductive material. Polarized light sensors could be used, wherein changes in light transmission properties are measured and correlated to the pressure or force exerted on the sole. One embodiment utilizes a multiple array (e.g. 100) of binary on/off sensors, and force components can be detected by "puddling" of sensor signals in specific areas. Still other types of sensors not mentioned herein may be used. It is understood that the sensors can be relatively inexpensive and capable of being placed in shoes in a mass-production process. More complex sensor systems that may be more expensive could be incorporated in a training type shoe. It is understood that a combination of different types of sensors may be used in one embodiment.

Additionally, the sensors 16 may be placed or positioned in engagement with the shoe structure in many different manners. In one example, the sensors 16 may be printed conductive ink sensors, electrodes, and/or leads deposited on a sole member, such as an airbag or other fluid-filled chamber, a foam material, or another material for use in the shoe 100, or a sock, bootie, insert, liner, insole, midsole, etc. The sensors 16 and/or leads 18 may be woven into garment or fabric structures (such as sockliners, booties, uppers, inserts, etc.), e.g., using conductive fabric or yarns when weaving or knitting the garment or fabric structures. Many embodiments of the sensor system 12 can be made inexpensively, for example, by using a force-sensitive resistor sensor or a force-sensitive resistive material, as described below and shown in FIGS. 8 and 11-21. It is understood that the sensors 16 and/or leads 18 also may be deposited on or engaged with a portion of the shoe structure in any desired manner, such as by conventional deposition techniques, by conductive nano-coating, by conventional mechanical connectors, and any other applicable known method. The sensor system can also be configured to provide mechanical feedback to the wearer. Additionally, the sensor system 12 may include a separate power lead to supply power or act as a ground to the sensors 16. In the embodiments described below and shown in FIGS. 5A-5E and FIGS. 27-35, the sensor system 12, 1312, 1412, 1512 includes a separate power lead 18A, 1318A, 1418A, 1518A that is used to connect the sensors 16, 1316, 1416, 1516 to the port 14, 14A-E to supply power from the module 22 to the sensors 16, 1316, 1416, 1516. As a further example, the sensor system 12 can be made by incorporating printed conductive ink sensors 16 or electrodes and conductive fabric or yarn leads 18, or forming such sensors on the foam or airbag of a shoe. Sensors 16 could be incorporated onto or into an airbag in a variety of manners. In one embodiment, the sensors 16 could be made by printing a conductive, force-sensitive material on the airbag on one or more surfaces of the airbag to achieve a strain gauge-like effect. When the bag surfaces expand and/or contract during activity, the sensors can detect such changes through changes in resistance of the force-sensitive material to detect the forces on the airbag. In a bag having internal fabrics to maintain a consistent shape, conductive materials can be located on the top and bottom of the airbag, and changes in the capacitance between the conductive materials as the bag expands and compresses can be used to determine force. Further, devices that can convert changes in air pressure into an electrical signal can be used to determine force as the airbag is compressed.

Figure 6:
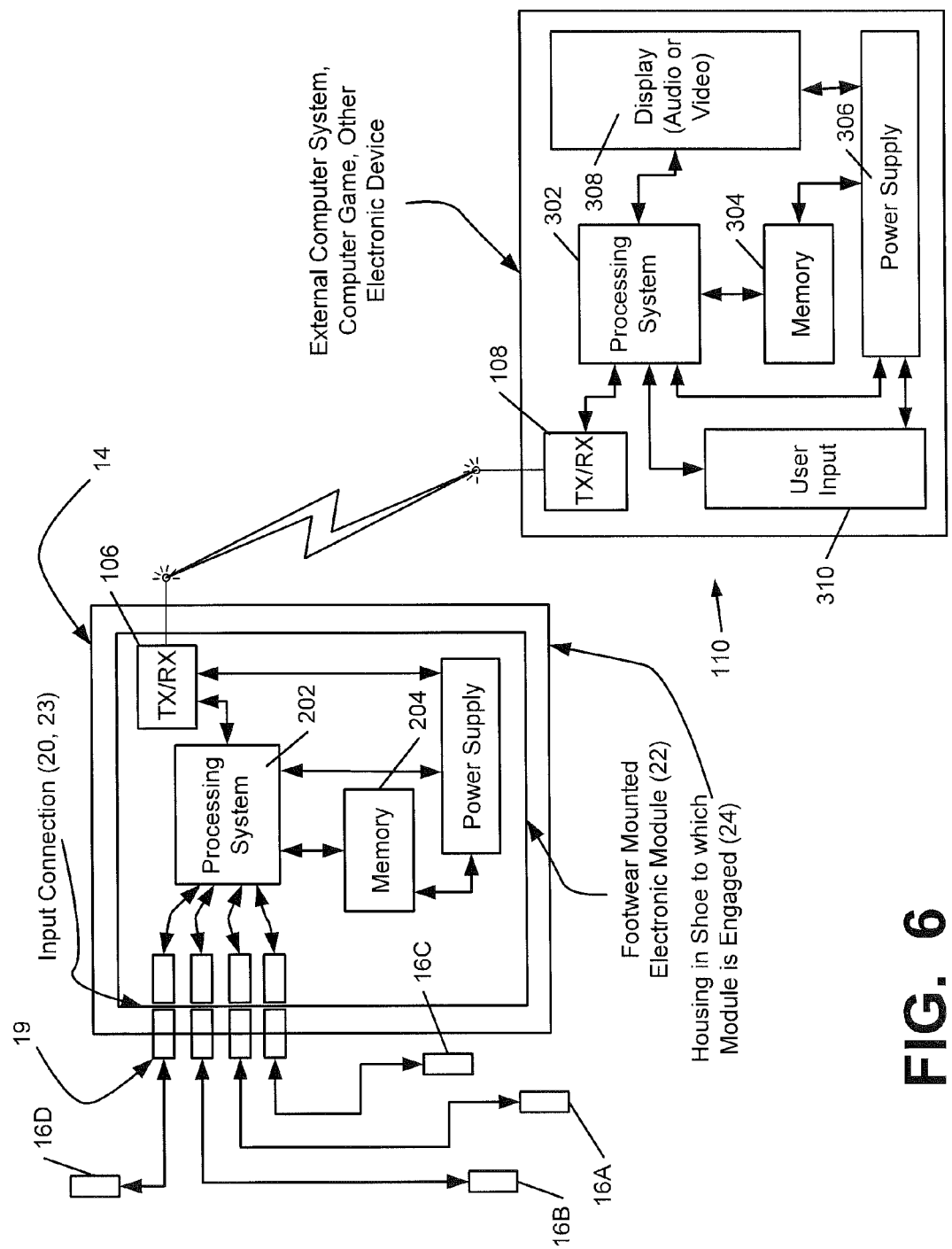
FIG. 6 is a schematic diagram of one embodiment of an electronic module capable of use with a sensor system, in communication with an external electronic device.

The port 14 is configured for communication of data collected by the sensors 16 to an outside source, in one or more known manners. In one embodiment, the port 14 is a universal communication port, configured for communication of data in a universally readable format. In the embodiments shown in FIGS. 3-5, the port 14 includes an interface 20 for connection to an electronic module 22, shown in connection with the port 14 in FIG. 3. In the embodiment shown in FIGS. 3-5, the interface 20 takes the form of electrical contacts. Additionally, in this embodiment, the port 14 is associated with a housing 24 for insertion of the electronic module 22, located in the well 135 in the middle arch or midfoot region of the article of footwear 100. The positioning of the port 14 in FIGS. 3-5 not only presents minimal contact, irritation, or other interference with the user's foot, but also provides easy accessibility by simply lifting the foot contacting member 133. Additionally, as illustrated in FIG. 6, the sensor leads 18 also form a consolidated interface or connection 19 at their terminal ends, in order to connect to the port 14 and the port interface 20. In one embodiment, the consolidated interface 19 may include individual connection of the sensor leads 18 to the port interface 20, such as through a plurality of electrical contacts. In another embodiment, the sensor leads 18 could be consolidated to form an external interface 19, such as a plug-type interface as described below, or in another manner, and in a further embodiment, the sensor leads 18 may form a non-consolidated interface, with each lead 18 having its own sub-interface. As illustrated in FIG. 6, the sensor leads 18 can converge to a single location to form the consolidated interface. As also described below, the module 22 may have an interface 23 for connection to the port interface 20 and/or the sensor leads 18.

The port 14 is adapted for connection to a variety of different electronic modules 22, which may be as simple as a memory component (e.g., a flash drive) or which may contain more complex features. It is understood that the module 22 could be as complex a component as a personal computer, mobile device, server, etc. The port 14 is configured for transmitting data gathered by the sensors 16 to the module 22 for storage and/or processing. In another embodiment, the port 14 may include necessary components (e.g. a processor, memory, software, TX/RX, etc.) in order to accomplish storage and/or execution of such computer programs/algorithms and/or direct (wired or wireless) transmission of data and/or other information to an external device 110. Examples of a housing and electronic modules in a footwear article are illustrated in U.S. patent application Ser. No. 11/416,458, published as U.S. Patent Application Publication No. 2007/0260421, which is incorporated by reference herein and made part hereof. Although the port 14 is illustrated with electronic contacts forming an interface 20 for connection to a module, in other embodiments, the port 14 may contain one or more additional or alternate communication interfaces for communication with the sensors 16, the module 22, the external device 110, and/or another component. For example, the port 14 may contain or comprise a USB port, a Firewire port, 16-pin port, or other type of physical contact-based connection, or may include a wireless or contactless communication interface, such as an interface for Wi-Fi, Bluetooth, near-field communication, RFID, Bluetooth Low Energy, Zigbee, or other wireless communication technique, or an interface for infrared or other optical communication technique (or combination of such techniques).

The sensor leads 18 may be connected to the port 14 in a variety of different configurations. FIGS. 5A-5E illustrate example embodiments of a port 14A-E positioned within a well 135 in an article of footwear 100, such as within a sole member of the sole structure 130 as described above. In the embodiments shown in FIGS. 5A-5E, the well 135 has a plurality of walls, including side walls 139 and a base wall 143.

Figure 5A:
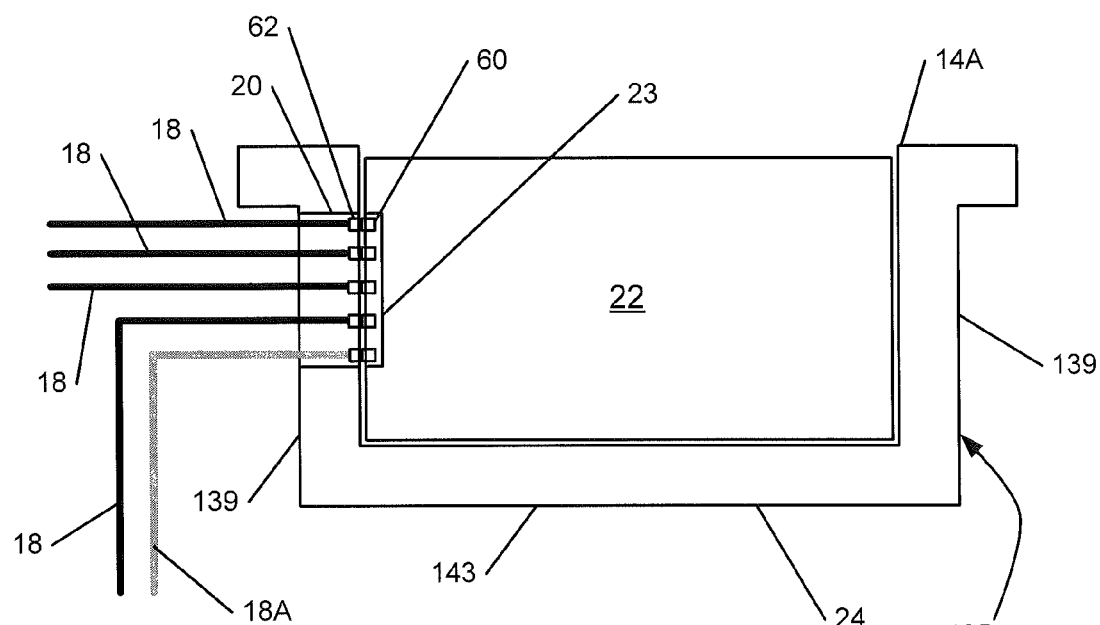
FIG. 5A is a side cross-sectional view of one embodiment of a port located in a well in a sole of an article of footwear.

FIG. 5A illustrates an embodiment of the port 14A where four sensor leads 18 and a power lead 18A are connected to the port 14A through a single side wall 139 of the well 135. In the embodiment illustrated, the sensor leads 18 form a consolidated interface in the form of a 5-pin connection, that is connected to an interface 20 of the port 14A. In this configuration, the leads 18, 18A are connected to the port interface 20 to form a consolidated interface, and each of the leads 18, 18A terminates in a connection pin 62 to form a multi-pin connection. This connection pin 62 can be considered an exposed end of the lead 18, 18A accessible within the well 135, in one embodiment. Likewise, the module 22 has a connection or interface 23 that includes five pin connections 60 for connection to the connection pins 62 of the leads 18, 18A in the port interface 20.

Figure 5B:
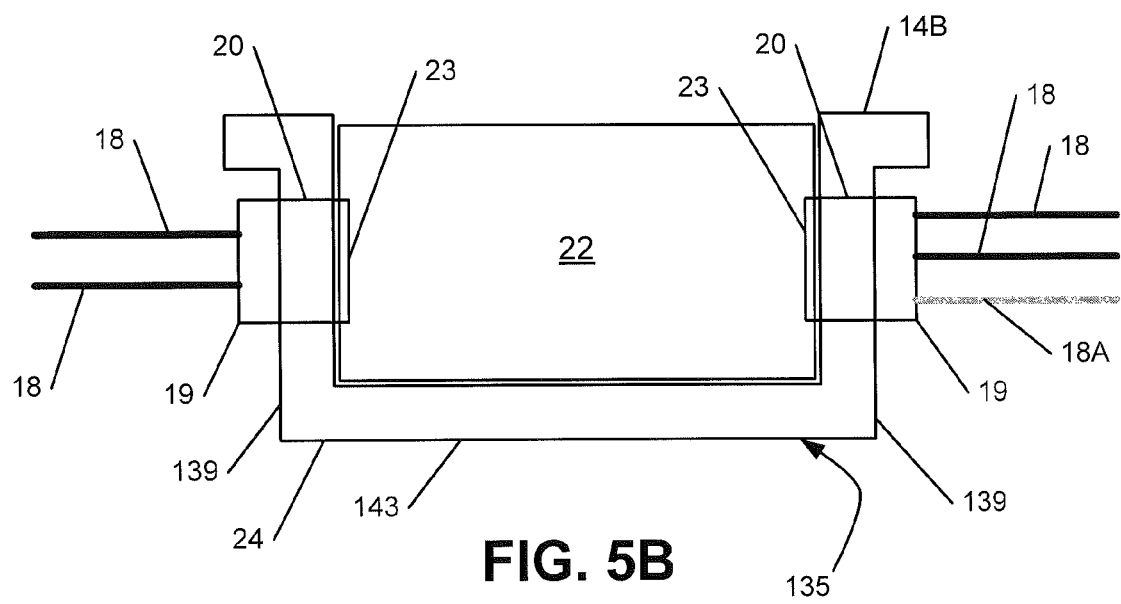
FIG. 5B is a side cross-sectional view of a second embodiment of a port located in a well in a sole of an article of footwear.

FIG. 5B illustrates an embodiment of the port 14B where two sensor leads 18 are connected to the port 14B through one of the side walls 139 of the well 135 and two other sensor leads 18 and a power lead 18A are connected to the port 14B through another one of the side walls 139. In this embodiment, the leads 18 form two separate consolidated lead interfaces 19, in the form of external interfaces 19, and the port 14B has two separate interfaces 20 for connection to the leads 18, 18A. The external interfaces 19 may be plug-type interfaces, pin-type interfaces, or other interfaces, and the port interfaces 20 are complementarily configured to connect to the external lead interfaces 19. Further, in this configuration, the module 22 has two interfaces 23 that are configured for connection to the port interfaces 20.

Figure 5C:
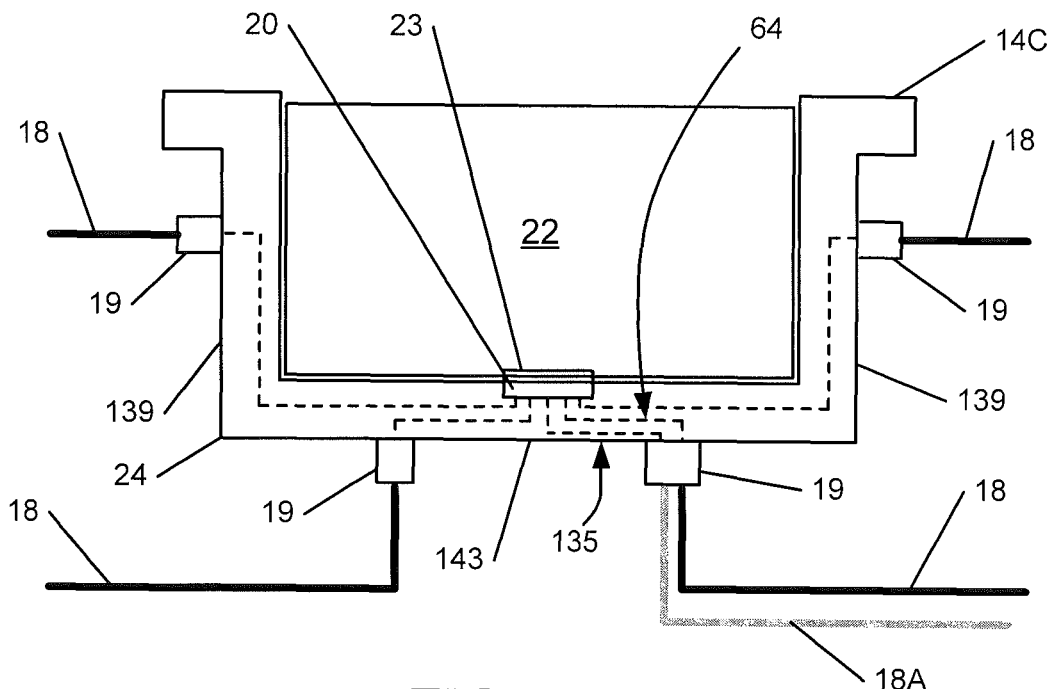
FIG. 5C is a side cross-sectional view of a third embodiment of a port located in a well in a sole of an article of footwear.

FIG. 5C illustrates an embodiment of the port 14C where the sensor leads 18 and the power lead 18A are connected to the port 14C through the side walls 139 and through the base wall 143 of the well 135. In this embodiment, the sensor leads 18 form several separate lead interfaces 19 for connection to the port 14C. The port 14C includes internal circuitry 64 that consolidates the connections of all the leads 18, 18A to the port interface 20, for connection to the module interface 23. The port 14C may further include complementary interfaces for connection to each of the lead interfaces 19. It is understood that the leads 18, 18A may be connected through one or more of the side walls 139 of the well 135 in this embodiment, and that the leads 18, 18A are shown connected through two of the side walls 139 for illustrative purposes. It is also understood that in this embodiment, more than one lead 18, 18A may be connected through a particular side wall 139 of the well 135, and that only one lead 18, 18A may be connected through the base wall 143.

Figure 5D:
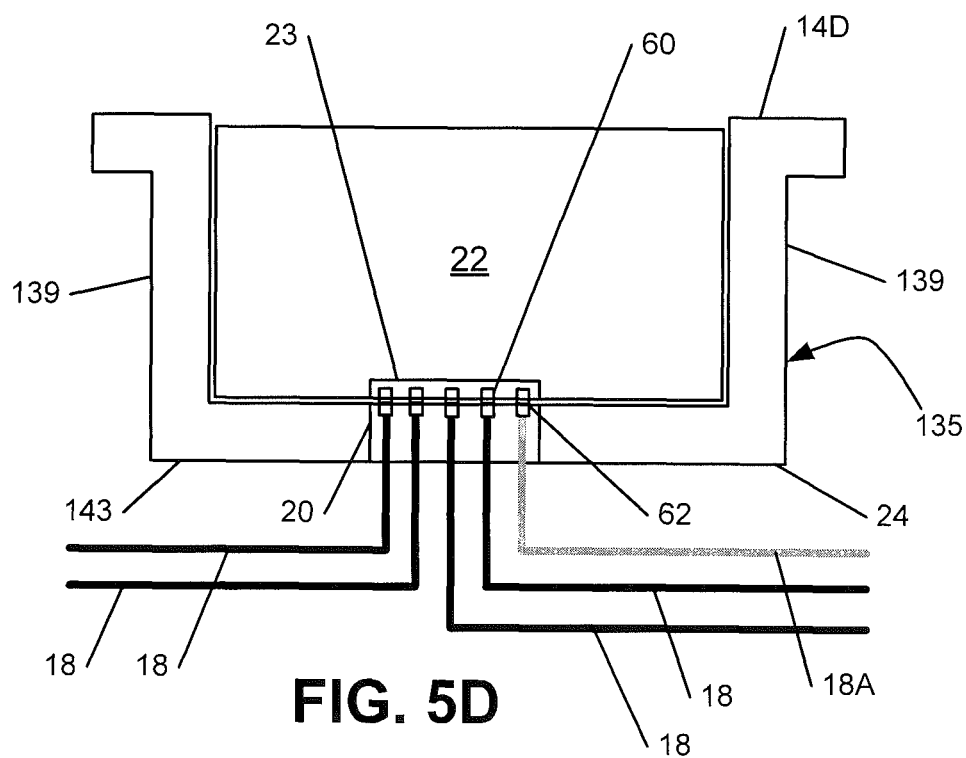
FIG. 5D is a side cross-sectional view of a fourth embodiment of a port located in a well in a sole of an article of footwear.

FIG. 5D illustrates an embodiment of the port 14D where four sensor leads 18 and a power lead 18A are connected to the port 14D through the base wall 143 of the well 135. In the embodiment illustrated, the leads 18, 18A form a consolidated interface that is connected to an interface 20 at the bottom of the port 14D, in a similar configuration to the connections described above and shown in FIG. 5A. Each of the leads 18, 18A terminates in a connection pin 62 at the port interface 20, and the module interface 23 includes a plurality of pin connections 60 configured for connection to the connection pins 62 of the leads 18, 18A.

Figure 5E:
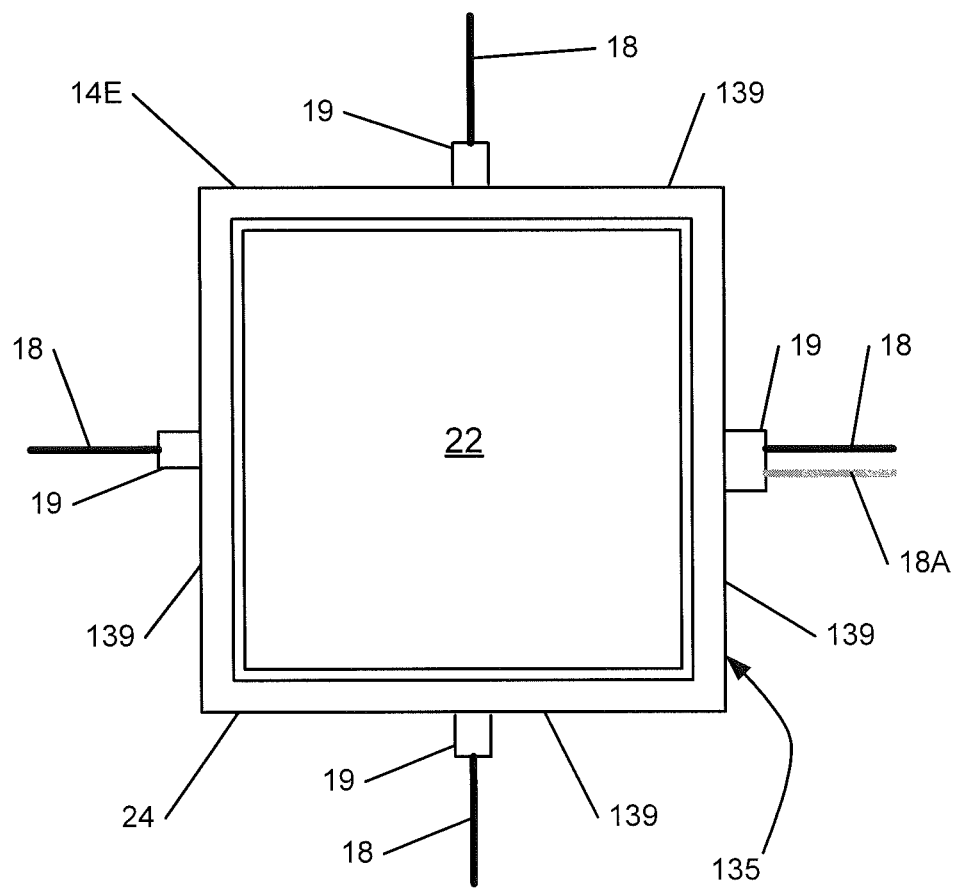
FIG. 5E is a top view of a fifth embodiment of a port located in a well in a sole of an article of footwear.

FIG. 5E illustrates an embodiment of the port 14E where four sensor leads 18 and a power lead 18A are connected to the port 14E through each of four side walls 139 of the well 135. In this embodiment, the leads 18, 18A form several separate interfaces 19 for connection to the port 14E, similar to the embodiment described above and shown in FIG. 5C. As described above, the port 14E may include complementary interfaces for connection to the lead interfaces 19, and may also include an interface for connection to the module 22. In other embodiments, the leads 18, 18A can be connected through any number of side walls 139 of the well 135.

In embodiments such as those illustrated in FIGS. 5B, 5C, and 5E, where the sensors 18 form more than one interface 19, the port 14B, 14C, 14E and/or the module 22 may have multiple interfaces 20, 23, or may have only a single interface 20, 23, and the port 14 may have internal circuitry 64 to connect all of the leads 18, 18A to the interfaces 20, 23. Additionally, the module 22 may have one or more interfaces 23 that are complementary to the interface(s) 20 of the port 14, for connection thereto. For example, if the port 14 has interface(s) 20 in the side walls 139 and/or base wall 143 thereof, the module 22 may have complementary interface(s) 23 in the side walls and/or base wall as well. It is understood that the module 22 and the port 14 may not have identically complementary interfaces 20, 23, and that only one pair of complementary interfaces 20, 23 may be able to achieve communication between the components. In other embodiments, the port 14 and the well 135 may have a different configuration for connection of the leads 18, 18A. Additionally, the port 14 may have a different shape, which may enable a greater variety of connection configurations. Further, any of the connection configurations described herein, or combinations thereof, can be utilized with the various embodiments of sensor systems described herein.

The module 22 may additionally have one or multiple communication interfaces for connecting to an external device 110 to transmit the data, e.g. for processing, as described below and shown in FIG. 6. Such interfaces can include any of the contacted or contactless interfaces described above. In one example, the module 22 includes at least a retractable USB connection for connection to a computer. In another example, the module 22 may be configured for contacted or contactless connection to a mobile device, such as a watch, cell phone, portable music player, etc. The module 22 may be configured to be removed from the footwear 100 to be directly connected to the external device 110 for data transfer, such as by the retractable USB connection described above or another connection interface. However, in another embodiment, the module 22 may be configured for wireless communication with the external device 110, which allows the device 22 to remain in the footwear 100 if desired. In a wireless embodiment, the module 22 may be connected to an antenna for wireless communication. The antenna may be shaped, sized, and positioned for use with the appropriate transmission frequency for the selected wireless communication method. Additionally, the antenna may be located internally within the module 22 or external to the module 22, such as at the port 14 or another location. In one example, the sensor system 12 itself (such as the leads 18 and conductive portions of the sensors 16) could be used to form an antenna in whole or in part. It is understood that the module 22 may contain an antenna in addition to an antenna connected elsewhere in the sensor system 12, such as at the port 14, at one or more of the sensors 16, etc. In one embodiment, the module 22 may be permanently mounted within the footwear 100, or alternately may be removable at the option of the user and capable of remaining in the footwear 100 if desired. Additionally, as further explained below, the module 22 may be removed and replaced with another module 22 programmed and/or configured for gathering and/or utilizing data from the sensors 16 in another manner. If the module 22 is permanently mounted within the footwear 100, the sensor system 12 may further contain an external port 15 to allow for data transfer and/or battery charging, such as a USB or Firewire port, as shown in FIG. 7. Such an external port 15 may additionally or alternately be used for communication of information. The module 22 may further be configured for contactless charging, such as inductive charging. It is understood that the module 22 may be configured for contacted and/or contactless communication.

While the port 14 may be located in a variety of positions without departing from the invention, in one embodiment, the port 14 is provided at a position and orientation and/or is otherwise structured so as to avoid or minimize contact with and/or irritation of the wearer's foot, e.g., as the wearer steps down in and/or otherwise uses the article of footwear 100, such as during an athletic activity. The positioning of the port 14 in FIGS. 3-5 illustrates one such example. In another embodiment, the port 14 is located proximate the heel or instep regions of the shoe 100. Other features of the footwear structure 100 may help reduce or avoid contact between the wearer's foot and the port 14 (or an element connected to the port 14) and improve the overall comfort of the footwear structure 100. For example, as illustrated in FIGS. 4-5, the foot contacting member 133, or other foot contacting member, may fit over and at least partially cover the port 14, thereby providing a layer of padding between the wearer's foot and the port 14.

Additional features for reducing contact between and modulating any undesired feel of the port 14 at the wearer's foot may be used. Of course, if desired, the opening to the port 14 may be provided through the top surface of the foot contacting member 133 without departing from the invention. Such a construction may be used, for example, when the housing 24, electronic module 22, and other features of the port 14 include structures and/or are made from materials so as to modulate the feel at the user's foot, when additional comfort and feel modulating elements are provided, etc. Any of the various features described above that help reduce or avoid contact between the wearer's foot and a housing (or an element received in the housing) and improve the overall comfort of the footwear structure may be provided without departing from this invention, including the various features described above in conjunction with FIGS. 4-5, as well as other known methods and techniques.

In one embodiment, where the port 14 is configured for contacted communication with a module 22 contained in a well 135 in the sole structure 130, the port 14 is positioned within or immediately adjacent the well 135, for connection to the module 22. It is understood that if the well 135 further contains a housing 24 for the module 22, the housing 24 may be configured for connection to the port 14, such as by providing physical space for the port 14 or by providing hardware for interconnection between the port 14 and the module 22. The positioning of the port 14 in FIG. 3 illustrates one such example, where the housing 24 provides physical space to receive the port 14 for connection to the module 22.

FIG. 6 shows a schematic diagram of an example electronic module 22 including data transmission/reception capabilities through a data transmission/reception system 106, which may be used in accordance with at least some examples of this invention. While the example structures of FIG. 6 illustrate the data transmission/reception system (TX-RX) 106 as integrated into the electronic module structure 22, those skilled in the art will appreciate that a separate component may be included as part of a footwear structure 100 or other structure for data transmission/reception purposes and/or that the data transmission/reception system 106 need not be entirely contained in a single housing or a single package in all examples of the invention. Rather, if desired, various components or elements of the data transmission/reception system 106 may be separate from one another, in different housings, on different boards, and/or separately engaged with the article of footwear 100 or other device in a variety of different manners without departing from this invention. Various examples of different potential mounting structures are described in more detail below.

In the example of FIG. 6, the electronic module 22 may include a data transmission/reception element 106 for transmitting data to and/or receiving data from one or more remote systems. In one embodiment, the transmission/reception element 106 is configured for communication through the port 14, such as by the contacted or contactless interfaces described above. In the embodiment shown in FIG. 6, the module 22 includes an interface 23 configured for connection to the port 14 and/or sensors 16. In the module 22 illustrated in FIG. 3, the interface 23 has contacts that are complementary with the contacts of the interface 20 of the port 14, to connect with the port 14. In other embodiments, as described above, the port 14 and the module 22 may contain different types of interfaces 20, 23, which may be wired or wireless. It is understood that in some embodiments, the module 22 may interface with the port 14 and/or sensors 16 through the TX-RX element 106. Accordingly, in one embodiment, the module 22 may be external to the footwear 100, and the port 14 may comprise a wireless transmitter interface for communication with the module 22. The electronic component 22 of this example further includes a processing system 202 (e.g., one or more microprocessors), a memory system 204, and a power supply 206 (e.g., a battery or other power source). The power supply 206 may supply power to the sensors 16 and/or other components of the sensor system 12. The shoe 100 may additionally or alternately include a separate power source to operate the sensors 16 if necessary, such as a battery, piezoelectric, solar power supplies, or others.

Connection to the one or more sensors can be accomplished through TX-RX element 106, and additional sensors (not shown) may be provided to sense or provide data or information relating to a wide variety of different types of parameters. Examples of such data or information include physical or physiological data associated with use of the article of footwear 100 or the user, including pedometer type speed and/or distance information, other speed and/or distance data sensor information, temperature, altitude, barometric pressure, humidity, GPS data, accelerometer output or data, heart rate, pulse rate, blood pressure, body temperature, EKG data, EEG data, data regarding angular orientation and changes in angular orientation (such as a gyroscope-based sensor), etc., and this data may be stored in memory 204 and/or made available, for example, for transmission by the transmission/reception system 106 to some remote location or system. The additional sensor(s), if present, may also include an accelerometer (e.g., for sensing direction changes during steps, such as for pedometer type speed and/or distance information, for sensing jump height, etc.).

As additional examples, electronic modules, systems, and methods of the various types described above may be used for providing automatic impact attenuation control for articles of footwear. Such systems and methods may operate, for example, like those described in U.S. Pat. No. 6,430,843, U.S. Patent Application Publication No. 2003/0009913, and U.S. Patent Application Publication No. 2004/0177531, which describe systems and methods for actively and/or dynamically controlling the impact attenuation characteristics of articles of footwear (U.S. Pat. No. 6,430,843, U.S. Patent Application Publication No. 2003/0009913, and U.S. patent application Publication No. 2004/0177531 each are entirely incorporated herein by reference and made part hereof). When used for providing speed and/or distance type information, sensing units, algorithms, and/or systems of the types described in U.S. Pat. Nos. 5,724,265, 5,955,667, 6,018,705, 6,052,654, 6,876,947 and 6,882,955 may be used. These patents each are entirely incorporated herein by reference. Additional embodiments of sensors and sensor systems, as well as articles of footwear and sole structures and members utilizing the same, are described in U.S. Patent Application Publications Nos. 2010/0063778 and 2010/0063779, which applications are incorporated by reference herein in their entireties and made part hereof.

In the embodiment of FIG. 6, an electronic module 22 can include an activation system (not shown). The activation system or portions thereof may be engaged with the module 22 or with the article of footwear 100 (or other device) together with or separate from other portions of the electronic module 22. The activation system may be used for selectively activating the electronic module 22 and/or at least some functions of the electronic module 22 (e.g., data transmission/reception functions, etc.). A wide variety of different activation systems may be used without departing from this invention. In one example, the sensor system 12 may be activated and/or deactivated by activating the sensors 16 in a specific pattern, such as consecutive or alternating toe/heel taps, or a threshold force exerted on one or more sensors 16.

In another example, the sensor system 12 may be activated by a button or switch, which may be located on the module 22, on the shoe 100, or on an external device in communication with the sensor system 12, as well as other locations. In any of these embodiments, the sensor system 12 may contain a "sleep" mode, which can deactivate the system 12 after a set period of inactivity. In one embodiment, the sensor system 12 may return to "sleep" mode if no further activity occurs in a short time after activation, in case of unintentional activation. In an alternate embodiment, the sensor system 12 may operate as a low-power device that does not activate or deactivate.

The module 22 may further be configured for communication with an external device 110, which may be an external computer or computer system, mobile device, gaming system, or other type of electronic device, as shown in FIG. 6. The exemplary external device 110 shown in FIG. 6 includes a processor 302, a memory 304, a power supply 306, a display 308, a user input 310, and a data transmission/reception system 108. The transmission/reception system 108 is configured for communication with the module 22 via the transmission/reception system 106 of the module 22, through any type of known electronic communication, including the contacted and contactless communication methods described above and elsewhere herein. It is understood that the module 22 can be configured for communication with a plurality of external devices, including a wide variety of different types and configurations of electronic devices, and that the device(s) with which the module 22 communicates can change over time. Additionally, the transmission/reception system 106 of the module 22 may be configured for a plurality of different types of electronic communication. It is further understood that the external device 110 as described herein may be embodied by two or more external devices in communication with the module 22, the port 14, and/or each other, including one or more intermediate devices that pass information to the external device 110, and that the processing, execution of programs/algorithms, and other functions of the external device 110 may be performed by a combination of external devices.

As described above, many different types of sensors can be incorporated into sensor systems according to the present invention. FIG. 8 illustrates one exemplary embodiment of a shoe 100 that contains a sensor system 212 that includes a sensor assembly 213 incorporating a plurality of force-sensitive resistor (FSR) sensors 216. The sensor system 212 is similar to the sensor system 12 described above, and also includes a port 14 in communication with an electronic module 22 and a plurality of leads 218 connecting the FSR sensors 216 to the port 14. The module 22 is contained within a well or cavity 135 in the sole structure 130 of the shoe 100, and the port 14 is connected to the well 135 to enable connection to the module 22 within the well 135. The port 14 and the module 22 include complementary interfaces 220, 223 for connection and communication.

The force-sensitive resistor shown in FIG. 8 contains first and second electrodes or electrical contacts 240, 242 and a force-sensitive resistive material 244 disposed between the electrodes 240, 242 to electrically connect the electrodes 240, 242 together. When pressure is applied to the force-sensitive material 244, the resistivity and/or conductivity of the force-sensitive material 244 changes, which changes the electrical potential between the electrodes 240, 242. The change in resistance can be detected by the sensor system 212 to detect the force applied on the sensor 216. The force-sensitive resistive material 244 may change its resistance under pressure in a variety of ways. For example, the force-sensitive material 244 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 244 may change the resistance by the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 244 and the electrode 240, 242 and/or the surface resistance between a conducting layer (e.g. carbon/graphite) and a force-sensitive layer (e.g. a semiconductor) of a multi-layer material 244. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 244, as defined herein, may be or include a doped or non-doped semiconducting material.

The electrodes 240, 242 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 218 can be connected to the electrodes 240, 242 by any suitable method, including welding, soldering, brazing, adhesively joining, fasteners, or any other integral or non-integral joining method. Alternately, the electrode 240, 242 and associated lead 218 may be formed of a single piece of the same material.

FIGS. 9-10 illustrate generally the use of a force-sensitive resistive material M in a sensor 16, such as the FSR sensors 216 shown in FIG. 8. The electrodes (+) and (−) have an electrical potential P1 between them, as shown in FIG. 9. When the force-sensitive resistive material M is compressed, the resistance of the material M changes, and thus, the potential P2 between the electrodes (+) and (−) changes, as shown in FIG. 10. The material M may utilize volume-based resistance, contact-based resistance, or other types of force-sensitive resistive behavior. For example, the force-sensitive resistive material 244 of the sensors 216 in FIG. 8 may behave in this manner. As another example, the quantum tunneling composite, custom conductive foam, force transducing rubber, and other force-sensitive resistive materials described below and shown in FIGS. 16-20 exhibit force-sensitive resistive behavior. It is understood that the electrodes (+) and (−) may be positioned in a different arrangement, such as in a sandwich arrangement with the material M positioned between the electrodes (+) and (−).

In the example embodiment shown in FIG. 8, the electrodes 240, 242 of the FSR sensor 216 have a plurality of interlocking or intermeshing fingers 246, with the force-sensitive resistive material 244 positioned between the fingers 246 to electrically connect the electrodes 240, 242 to each other. In the embodiment shown in FIG. 8, each of the leads 218 independently supplies power from the module 22 to the sensor 216 to which each respective lead 218 is connected. It is understood that the sensor leads 218 may include separate leads extending from each electrode 240, 242 to the port 14, and that the module 22 may provide electrical power to the electrodes 240, 242 through such separate leads, such as through a separate power lead 18A, 1318A as described elsewhere herein.

Force-sensitive resistors suitable for use in the sensor system 212 are commercially available from sources such as Sensitronics LLC. Examples of force-sensitive resistors which maybe suitable for use are shown and described in U.S. Pat. Nos. 4,314,227 and 6,531,951, which are incorporated herein by reference in their entireties and made parts hereof.

Figure 27:
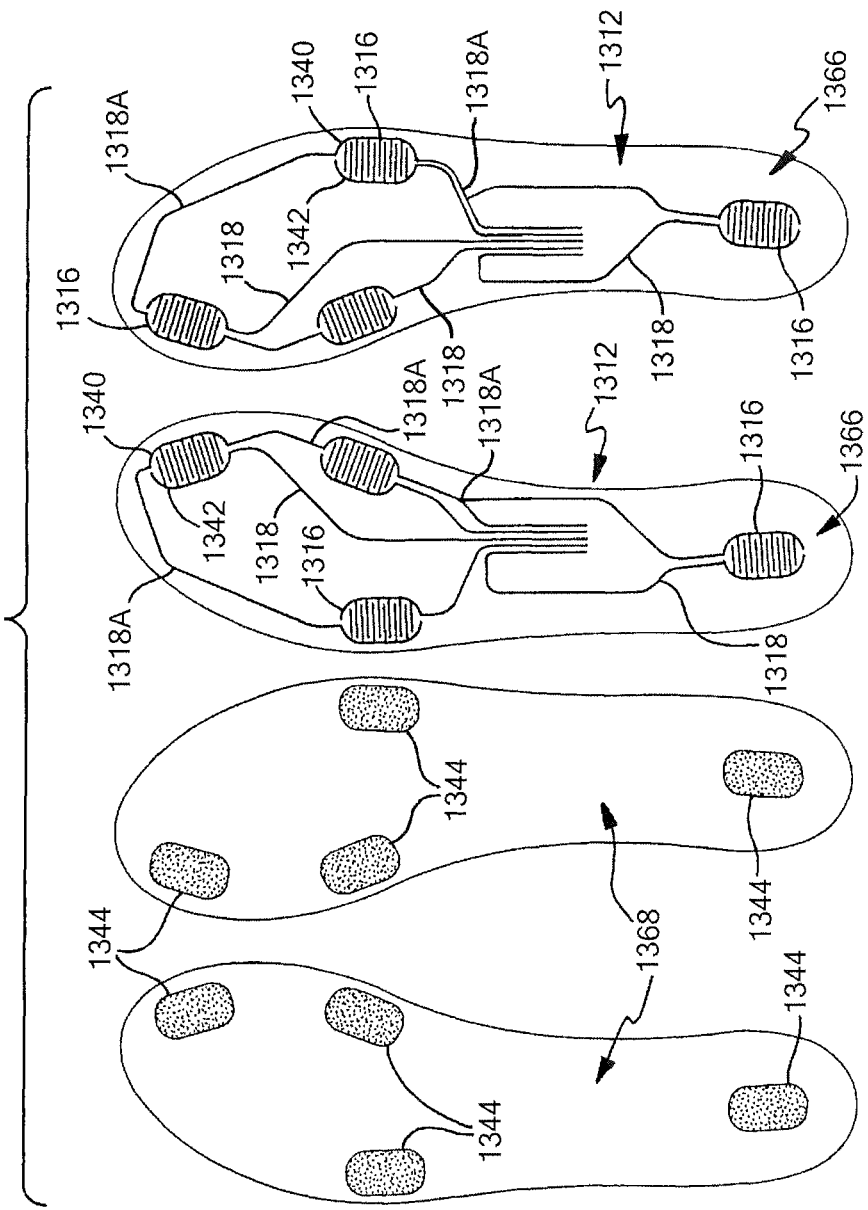
FIG. 27 is a top view of two sets of layers for use in constructing a sensor system.
Figure 28:
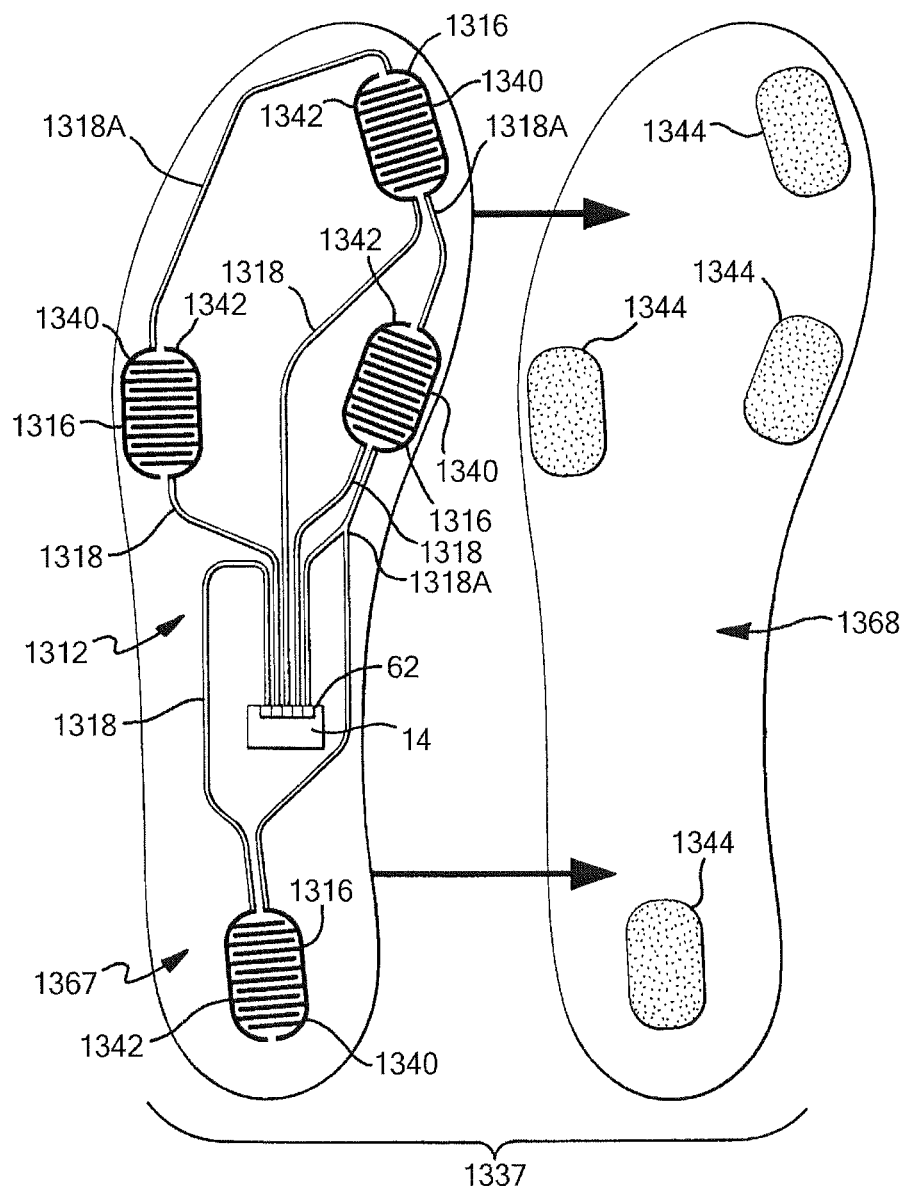
FIG. 28 is a top view of the assembly of an insert member containing a sensor system, using one set of layers as shown in FIG. 27.

FIGS. 27-28 illustrate another embodiment of an FSR sensor system 1312 for incorporation into an article of footwear 100. The sensor system 1312 includes four sensors 1316, with a first sensor 1316 positioned in the first phalange (big toe) area, a second sensor 1316 positioned in the first metatarsal head area, a third sensor 1316 positioned in the fifth metatarsal head area, and a fourth sensor 1316 positioned in the heel area, similarly to the configuration shown in FIG. 3. The sensors 1316 each have a sensor lead 1318 connecting the sensor 1316 to the port 14. Additionally, a power lead 1318A extends from the port 14 and is connected to all four sensors 1316. The power lead 1318A may be connected in a parallel, series, or other configuration in various embodiments, and each sensor 1316 may have an individual power lead in another embodiment. As shown in FIG. 28, each of the leads 1318, 1318A are connected to the port 14 for connection and transfer of data to a module (not shown) connected to the port 14. It is understood that the port 14 may have any configuration described herein. In this embodiment, the leads 1318, 1318A are positioned suitably for a 5-pin connection as shown in FIG. 5A, with a plurality of connection pins 62.

Similarly to the system 212 described above with respect to FIG. 8, each sensor 1316 of the sensor system 1312 contains first and second electrodes or electrical contacts 1340, 1342 and a force-sensitive resistive material 1344 disposed between the electrodes 1340, 1342 to electrically connect the electrodes 1340, 1342 together. When force/pressure is applied to the force-sensitive material 1344, the resistivity and/or conductivity of the force-sensitive material 1344 changes, which changes the electrical potential and/or the current between the electrodes 1340, 1342. The change in resistance can be detected by the sensor system 1312 to detect the force applied on the sensor 1316. Additionally, the FSR sensors 1316 each have a plurality of interlocking or intermeshing fingers 1346, with the force-sensitive resistive material 1344 positioned between the fingers 1346 to electrically connect the electrodes 1340, 1342 to each other.

In the embodiment of the sensor system 1312 shown in FIGS. 27-28, each sensor 1316 includes two contacts 1340, 1342 constructed of a conductive metallic layer and a carbon layer (such as carbon black) forming a contact surface on the metallic layer (not shown). The sensors 1316 also include a force-sensitive resistive material 1344 that also is constructed of a layer or puddle of carbon (such as carbon black), which is in contact with the carbon contact surface of the electrodes 1340, 1342. The carbon-on-carbon contact can produce greater conductivity changes under pressure, increasing the effectiveness of the sensors 1316. The leads 1318, 1318A in this embodiment are constructed of a conductive metallic material that may be the same as the material of the metallic layer of the contacts 1340, 1342. In one embodiment, the leads 1318, 1318A and the metallic layers of the contacts 1340, 1342 are constructed of silver.

As shown in FIGS. 27-28, in this example embodiment, the sensor system 1312 is constructed of two flexible layers 1366 and 1368 that combine to form an insert member 1337 for insertion into an article of footwear, such as between the foot contacting member 133 and the midsole member 131 as discussed below. The layers can be formed of any flexible material, such as a flexible polymer material. In one embodiment, the layers 1366, 1368 are formed of a 0.05-0.2 mm thick pliable thin Mylar material. The insert 1337 is constructed by first depositing the conductive metallic material on the first layer 1366, such as by printing, in the traced pattern of the leads 1318, 1318A and the electrodes 1340, 1342 of the sensors 1316, to form the configuration shown in FIG. 27. Then, the additional carbon contact layer is deposited on the first layer 1366, tracing over the electrodes 1340, 1342 of the sensors 1316, and the carbon force-sensitive resistive material 1344 is deposited as puddles on the second layer 1368, as also shown in FIG. 27. After all the materials have been deposited, the layers 1366, 1368 are positioned in a superimposed manner, as shown in FIG. 28, so that the electrodes 1340, 1342 are aligned with the puddles of force-sensitive resistive material 1344, to form the insert member 1337 for insertion into the article of footwear 100. It is understood that the conductive metallic material and the carbon material 1344 are deposited on the faces of the layers 1366, 1368 that face each other (e.g. the top surface of the bottom-most layer 1366, 1368 and the bottom surface of the top-most layer 1366, 1368). In one embodiment, the sensor system 1312 constructed in this manner can detect pressures in the range of 10-750 kPa. In addition, the sensor system 1312 may be capable of detecting pressures throughout at least a portion of this range with high sensitivity.

Figure 29:
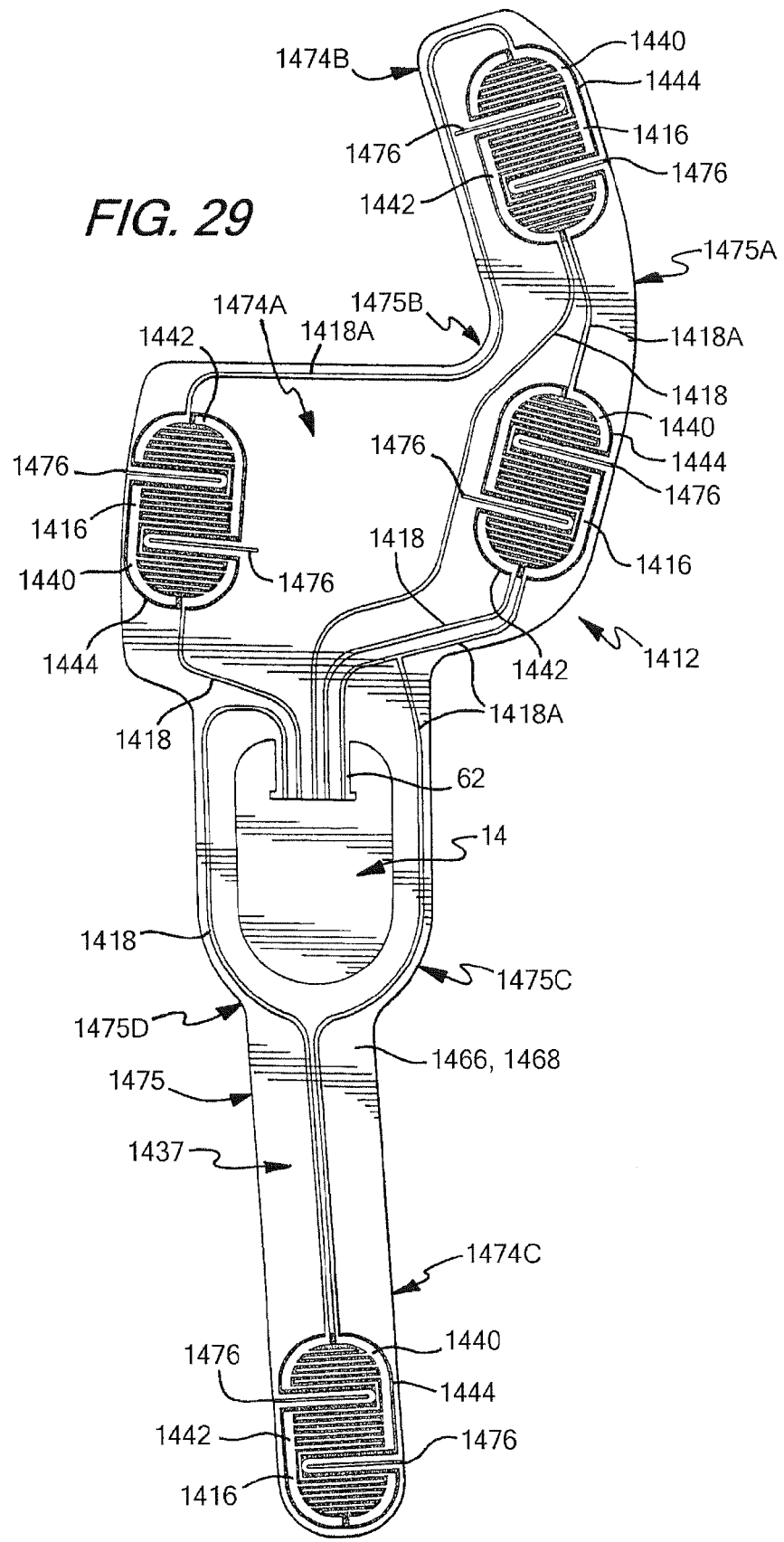
FIG. 29 is a top view of another embodiment of an insert member containing a sensor system according to aspects of the invention.
Figure 30:
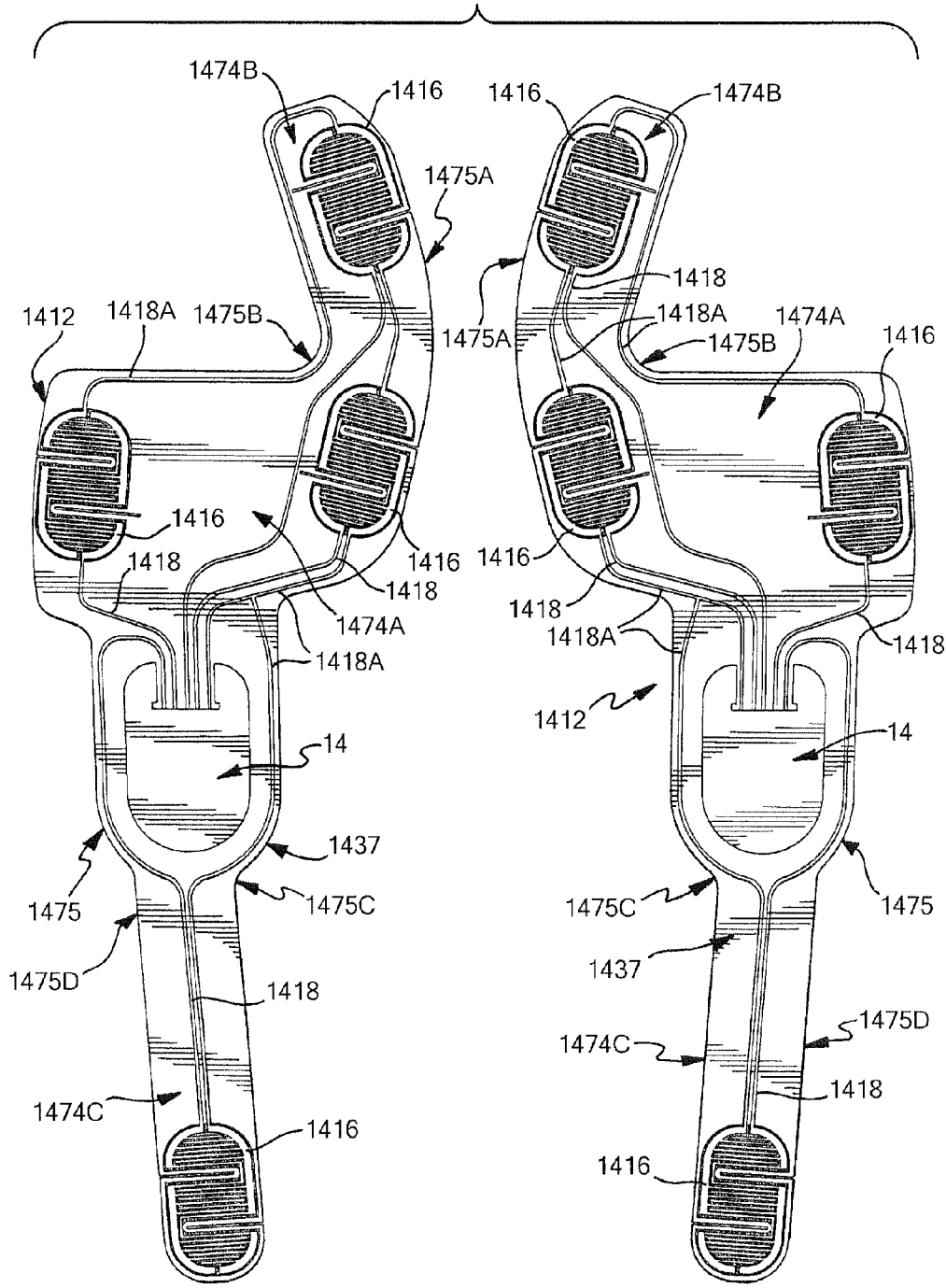
FIG. 30 is a top view of a left and right pair of insert members as shown in FIG. 29.

FIGS. 29-32 illustrate another embodiment of an FSR sensor system 1412 for incorporation into an article of footwear 100. The sensor system 1412 includes four sensors 1416, with a first sensor 1416 positioned in the first phalange (big toe) area, a second sensor 1416 positioned in the first metatarsal head area, a third sensor 1416 positioned in the fifth metatarsal head area, and a fourth sensor 1416 positioned in the heel area, similarly to the configuration shown in FIGS. 3 and 27-28. The sensors 1416 each have a sensor lead 1418 connecting the sensor 1416 to the port 14. Additionally, a power lead 1418A extends from the port 14 and is connected to all four sensors 1416. The power lead 1418A may be connected in a parallel, series, or other configuration in various embodiments, and each sensor 1416 may have an individual power lead in another embodiment. As shown in FIG. 29, each of the leads 1418, 1418A are connected to the port 14 for connection and transfer of data to a module (not shown) connected to the port 14. It is understood that the port 14 may have any configuration described herein. In this embodiment, the leads 1418, 1418A are positioned suitably for a 5-pin connection as shown in FIG. 5A, with a plurality of connection pins 62.

Similarly to the system 1312 described above with respect to FIGS. 26-28, each sensor 1416 of the sensor system 1412 shown in FIGS. 29-32 contains first and second electrodes or electrical contacts 1440, 1442 and a force-sensitive resistive material 1444 disposed between the electrodes 1440, 1442 to electrically connect the electrodes 1440, 1442 together. In this embodiment, similarly to the embodiment of FIGS. 26-28, the electrodes 1440, 1442 are positioned in contact with a surface of the force-sensitive material 1444, such that the electrodes 1440, 1442 and the force-sensitive material 1444 have confronting surfaces that can engage each other in surface-to-surface contact, as described in greater detail below. When pressure is applied to the force-sensitive material 1444, the resistivity and/or conductivity of the force-sensitive material 1444 changes, which changes the electrical potential and/or the current between the electrodes 1440, 1442. The change in resistance can be detected by the sensor system 1412 to detect the force applied on the sensor 1416. Additionally, the electrodes 1440, 1442 of the FSR sensors 1416 each have a plurality of interlocking or intermeshing fingers 1446, with the force-sensitive resistive material 1444 positioned between the fingers 1446 to electrically connect the electrodes 1440, 1442 to each other.

In the embodiment of the sensor system 1412 shown in FIGS. 29-32, each sensor 1416 includes two electrodes 1440, 1442 constructed of a conductive metallic layer and optionally a carbon layer (such as carbon black) forming a contact surface on the metallic layer, as described above with respect to the sensors 1316 of FIGS. 27-28. The sensors 1416 also include a force-sensitive resistive material 1444 that also is constructed of a layer, patch, or puddle 1444A of carbon (such as carbon black), which is in contact with the carbon contact surface of the electrodes 1440, 1442. The leads 1418, 1418A in this embodiment are constructed of a conductive metallic material that may be the same as the material of the metallic layer of the electrodes 1440, 1442. In one embodiment, the leads 1418, 1418A and the metallic layers of the electrodes 1440, 1442 are constructed of silver.

Figure 31:
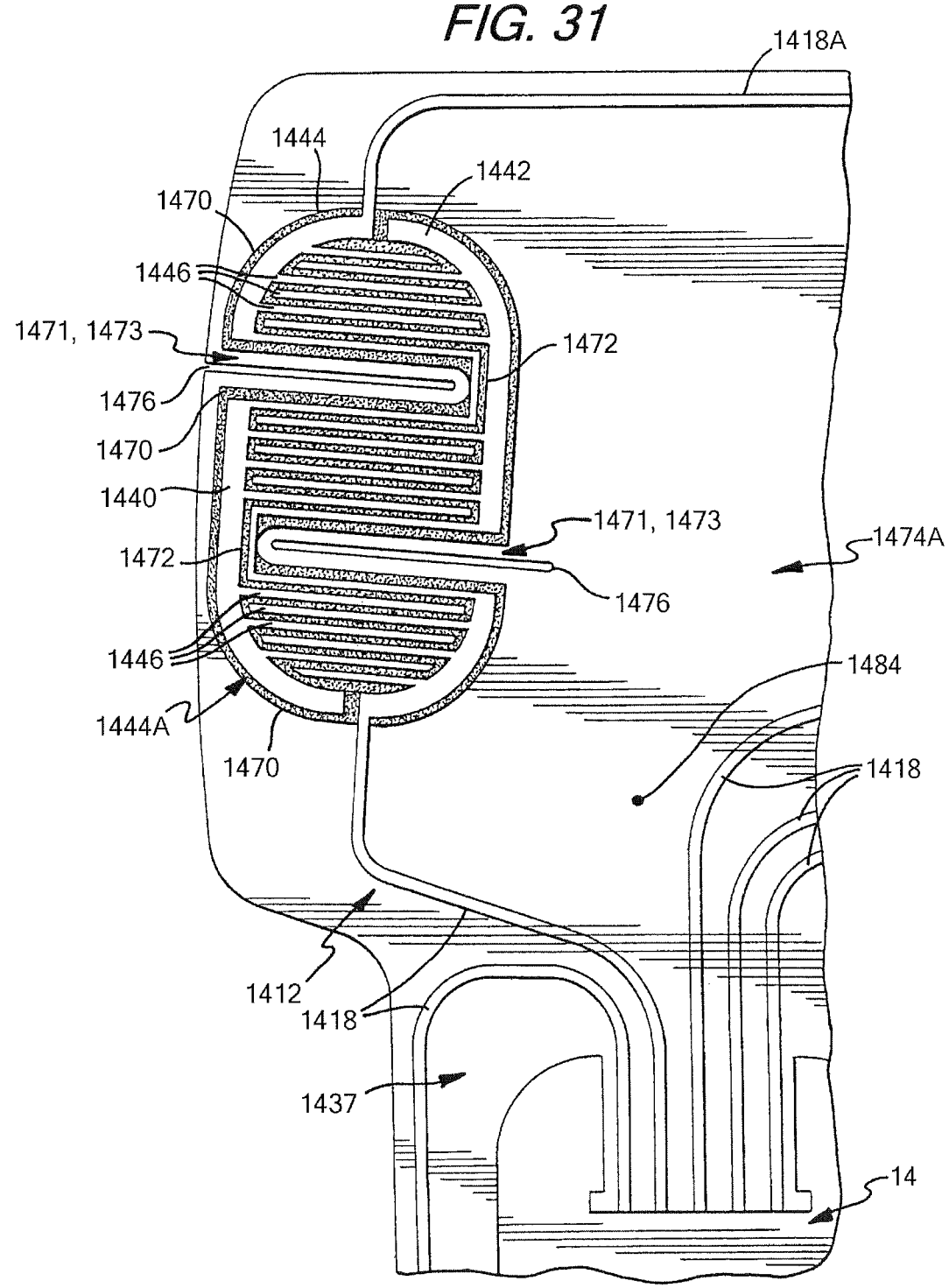
FIG. 31 is a magnified view of a portion of the insert member and sensor system of FIG. 29.
Figure 32:
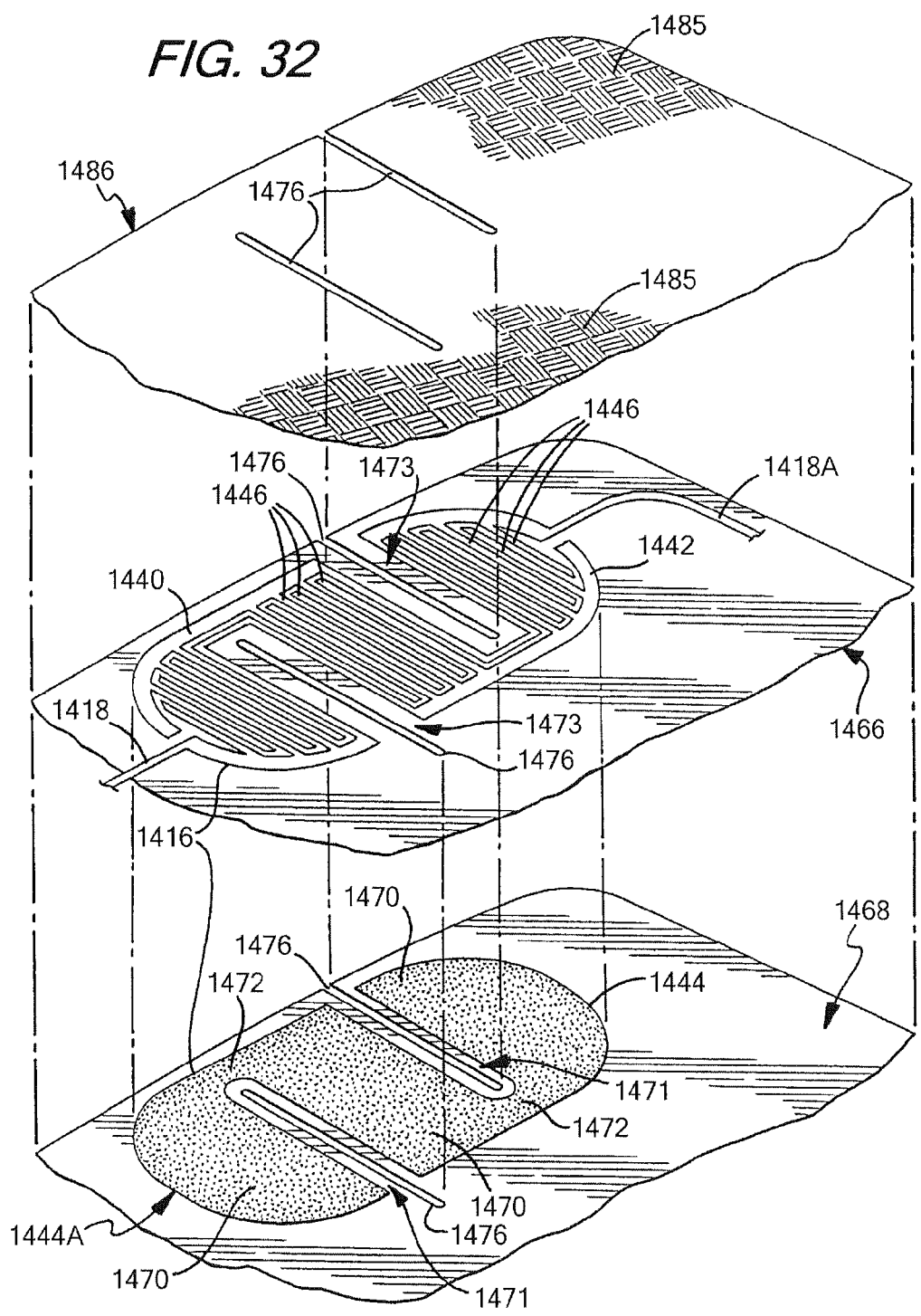
FIG. 32 is a magnified exploded view of a portion of the insert member and sensor system of FIG. 29, with a graphic layer.

As shown in FIG. 32, the patches 1444A of the force-sensitive material 1444 have a multi-lobed structure that is formed of a plurality of lobes 1470 that are separate or substantially separate from each other. In the embodiment shown in FIGS. 29-32, the patches 1444A of the force-sensitive material 1444 have three lobes 1470 that are separated by gaps 1471. The lobes 1470 are substantially separate from each other and are connected by bridges 1472 extending across the gaps 1471, such that the bridges 1472 form electrical connections between the lobes 1470. In the configuration in FIG. 32, the lobes 1470 are arranged in a row and have two gaps 1471 between the three lobes 1470, with each gap 1471 having a bridge 1472 spanning across. In other words, the center lobe 1470 in the row is separated by gaps 1471 from the other two lobes 1470, with bridges 1472 extending across the gaps 1471 to connect the center lobe 1470 to the other two lobes 1470. Additionally, in this configuration, one of the bridges 1472 is located on one lateral side of the patch 1444A, and the other bridge 1472 is located on the opposite lateral side of the patch 1444A, giving the patch 1444A a substantially S-shaped structure.

Further, the gaps 1471 in this embodiment have a straight and elongated configuration, and the material of the insert 1437 on which the sensors 1416 are mounted may have slits 1476 extending within the gaps 1471, as described below. In other embodiments, the patch 1444A may have a different structure, such as a non-lobed or a different multi-lobed structure that has differently-configured lobes 1470, gaps 1471, and/or bridges 1472. For example, the patch 1444A may have a two-lobed structure, or may have a three-lobed structure that has a different structure, such as a triangular shape having three bridges 1472, or may further have lobes 1470 that are not electrically connected to each other.

The electrodes 1440, 1442 in this embodiment have a plurality of spaced fingers 1446, as shown in FIGS. 31-32, similarly to the electrodes 1340, 1342 described above. Each electrode 1440, 1442 has at least one a plurality of the fingers 1446 in contact with each of the lobes 1470 of the patches 1444A of the force-sensitive material. Additionally, the electrodes 1440, 1442 each have two enlarged spaces 1473 that are larger than the other spaces between the fingers 1446, and the spaces 1473 are positioned to be superimposed over the gaps 1471 in the force-sensitive material. Due to the spaces 1473, the electrodes 1440, 1442 have no fingers 1446 that are located within the gaps 1471. In other words, the electrodes 1440, 1442 in this embodiment may also be considered to have a substantially S-shaped multi-lobed structure with lobes that are substantially separated by the spaces 1473, similar to the patches 1444A of the force-sensitive material 1444.

Certain factors, such as the surface area ratio or percentage of the electrodes 1440, 1442 and the force sensitive material 1444, and the spacing between the fingers 1446 of the electrodes 1440, 1442, may influence the resistance and output of the sensor 1416. In one embodiment, the fingers 1446 of the electrodes 1440, 1442 are configured so that the ratio of the surface area of the electrodes 1440, 1442 to the surface area of the force sensitive material 1444 is between about 3:1 and 1:3, or in other words, the electrodes 1440, 1442 cover about 25-75% of the total surface area of the patches 1444A of the force sensitive material. In another embodiment, the fingers 1446 of the electrodes 1440, 1442 are configured so that the ratio of the surface area of the electrodes 1440, 1442 to the surface area of the force sensitive material 1444 is about 1:1, or in other words, the electrodes 1440, 1442 cover about 50% of the total surface area of the patches 1444A of the force sensitive material. It is understood that these values may be measured as a ratio or a percentage of the force sensitive material 1444 that is within or substantially within the peripheral boundaries of the electrodes 1440, 1442, and that additional force sensitive material 1444 outside the boundaries of the electrodes 1440, 1442 may not have significant effect. Additionally, the average spacing between the fingers 1446 may be between 0.25 mm and 1.5 mm in one embodiment, and about 0.50 mm in another embodiment. Further, the fingers 1446 may have widths of about 0.50 mm in one embodiment. These configurations can assist in achieving a desired relationship or proportionality between the force (e.g., weight) load applied to the sensor 1416 and the resistance of the sensor 1416 and/or between the force load applied and the output of the sensor 1416. In one embodiment, the sensor 1416 produces a gradual change in signal strength with gradually increased force, and such relationships may be linear or curvilinear in nature. For example, in one embodiment, these relationships are linear, with a slope that approaches 1, or in other words, the resistance of the sensor 1416 and/or the resultant output signal increase and decrease in approximately a 1:1 proportion to the force that is applied. This relationship between the applied force and the resistance/output enables accurate determination of force applied to each sensor 1416, since the signal changes in a manner that is directly proportional to the force applied. Accordingly, in this embodiment, the sensor system 1412 can produce signals and data that are accurately reflective of forces applied to the sensors 1416, which can be used, for example, to accurately measure forces applied to the sensors 1416 or to accurately determine relative differences in forces applied to the sensors 1416, among other purposes. In other embodiments, the force applied to the sensor 1416 may have a different relationship or proportionality to the resistance and/or the resultant signal, and may be a simple binary (on-off) switching relationship in one embodiment.

As shown in FIG. 32, in this example embodiment, the sensor system 1412 is constructed of two flexible layers 1466 and 1468 that combine to form an insert member 1437 for insertion into an article of footwear, such as between the foot contacting member 133 and the midsole member 131 as discussed below. The layers can be formed of any flexible material, such as a flexible polymer material. In one embodiment, the layers 1466, 1468 are formed of a thin PET (e.g. Teslin) or Mylar material, or any other suitable material, including those materials described herein. One or more additional protective layers (not shown) may also be used in the insert 1437, which may be made of the same material or a different material from the first and second layers 1466, 1468. The insert 1437 is constructed by first depositing the conductive metallic material on the first layer 1466, such as by printing, in the traced pattern of the leads 1418, 1418A and the electrodes 1440, 1442 of the sensors 1416, to form the configuration shown in FIGS. 29-32. Then, the additional carbon contact layer, if present, is deposited on the first layer 1466, tracing over the electrodes 1440, 1442 of the sensors 1416, and the carbon force-sensitive resistive material 1444 is deposited as puddles or patches 1444A on the second layer 1468, as also shown in FIG. 32. After all the materials have been deposited, the layers 1466, 1468 are positioned in a superimposed manner, as shown in FIG. 32, so that the electrodes 1440, 1442 are aligned with the puddles of force-sensitive resistive material 1444, to form the insert member 1437 for insertion into the article of footwear 100. The layers 1466, 1468 can be connected together by an adhesive or other bonding material in one embodiment, and a variety of other techniques can be used for connecting the layers 1466, 1468 in other embodiments, such as heat sealing, spot welding, or other known techniques. In one embodiment, the sensor system 1412 constructed in this manner can detect pressures in the range of 10-750 kPa. In addition, the sensor system 1312 may be capable of detecting pressures throughout at least a portion of this range with high sensitivity. Additionally, in one embodiment, one or both of the layers 1466, 1468 may have one or more vent holes 1484 therein to allow air to escape from between the layers 1466, 1468 during use and/or manufacture. A single vent hole 1484 is illustrated in FIG. 31. In one embodiment, the second layer 1468 may have a vent hole 1484 near each sensor 1416, to allow air to vent out of the area around the sensor 1416.

The insert 1437 illustrated in FIGS. 29-32 has a configuration that may utilize less material than other insert configurations, such as the configuration of the insert 1337 in FIGS. 27-28. The configuration of the insert 1437 may provide additional advantages, such as in resisting tearing and propagation of tears/cracks, ease of insertion into a shoe during or after manufacturing, etc. In this embodiment, the insert 1437 has several portions of material cut out of areas of the insert 1437 that may be superfluous, such as in the lateral forefoot area or the lateral and medial heel areas. The insert 1437 in this configuration has a central portion 1474A configured to be engaged by the midfoot and/or forefoot (i.e. metatarsal) region of the user's foot, with a first phalange portion 1474B and a heel portion 1474C extending from opposite ends of the midfoot portion 1474A, configured to be engaged by the first phalange region and the heel region of the user's foot, respectively. It is understood that, depending on the shape of the user's foot, the first phalange portion 1474B may engage only the first phalange region of the user's foot. In this embodiment, the width of the central portion 1474A is greater than the width of the first phalange portion 1474B and the heel portion 1474C, such that the first phalange portion 1474B and the heel portion 1474C are configured as strips or tongues of the insert material that extend from the wider central portion 1474A in elongated manners. As referred to herein, the width of a portion of the insert 1437 is measured in the medial-to-lateral direction, and the length is measured in the front-to-rear direction. In the embodiment of FIGS. 29-32, the sensors 1416 are arranged similarly to the sensors 16A-D in FIG. 3, described above. The first phalange portion 1474B has one of the sensors 1416 located thereon, to be engaged by the first phalange of the user, and the heel portion 1474C has another one of the sensors 1416 thereon, to be engaged by the heel of the user. The remaining two sensors 1416 are located on the central portion 1474A at the forefoot area of the insert 1437, specifically at the first metatarsal head region and at the fifth metatarsal head region, to be engaged by the first and fifth metatarsal head regions of the user's foot, respectively.

In the embodiment shown in FIGS. 29-32, the insert 1437 has a peripheral edge 1475 defining a periphery of the insert 1437, and having several cut-out portions, as described above. For example, the insert 1437 has a cut-out portion at or around the second through fifth phalange region, and two cut-out portions at the medial and lateral edges of the heel portion 1474C. Described another way, the peripheral edge 1475 has a front medial edge 1475A extending from a medial side of the central portion 1474A to a medial side of the first phalange portion 1474B, a front lateral edge 1475B extending from a lateral side of the central portion 1474A to a lateral side of the first phalange portion 1474B, a rear medial edge 1475C extending from a medial side of the central portion 1474A to a medial side of the heel portion 1474C and a rear lateral edge 1475D extending from a lateral side of the central portion 1474A to a lateral side of the heel portion 1474C. The front lateral edge 1475B has an inwardly-curved or otherwise indented shape, creating one cut-out portion, while the front medial edge 1475A has an outwardly-curved shape. Additionally, the rear medial edge 1475C and the rear lateral edge 1475D each have at least one inwardly-curved or otherwise indented edge, creating the other cut-out portions. The cut-out portions give the first phalange portion 1474B and the heel portion 1474C their elongated strip or tongue configuration. It is understood that insert 1437 may have any number of different configurations, shapes, and structures, and including a different number and/or configuration of sensors 1416, and a different insert structure or peripheral shape.

The insert 1437 of FIGS. 29-32 additionally has a plurality of slits 1476 in the material of the insert 1437, which may influence the bending and flexing properties of the insert 1437. For example, the slits 1476 may allow for more even flexing of the surrounding areas of the insert 1437, such as during compression of the sensors 1416, creating a more normal (i.e. perpendicular) force on the sensors 1416. The sensors 1416 typically operate more effectively with a normal force than with a bending, twisting, or shearing force, and accordingly, this may result in a cleaner signal with less noise and/or distortion. At least some of the slits 1476 may be positioned proximate the sensors 1416, and may extend inwardly from the peripheral edge 1475 of the insert 1437. Additionally, one or more of the slits 1476 may be positioned in an internal gap, notch, indent, etc. of one or more of the sensors 1416 (such as the gaps 1471 described above). In the embodiment shown in FIGS. 29-33, two slits 1476 are positioned proximate each sensor 1416, with each slit 1476 extending into one of the gaps 1471 between the lobes 1470 in the force-sensitive material 1444. The slits 1476 in this embodiment are elongated and extend completely through the material of the insert 1437. Additionally, some of the slits 1476 extend inwardly from the peripheral edge 1475 of the insert 1437, and others are positioned completely within the insert 1437 and do not contact the peripheral edge. It is understood that the insert 1437 may include additional slits 1476 that do not extend into the boundaries of the sensors 1416 and/or differently configured slits 1476, in various embodiments.

Figure 33:
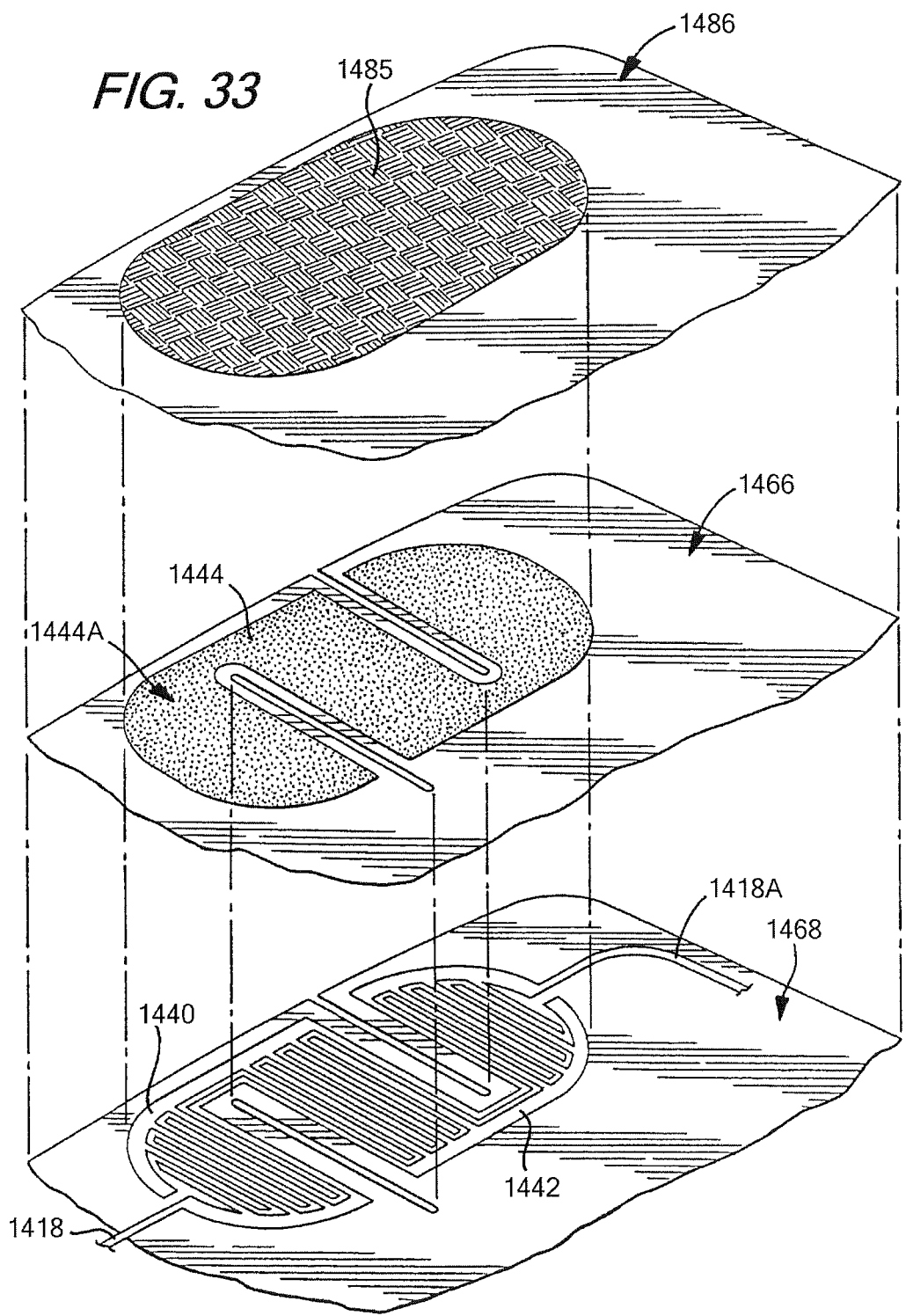
FIG. 33 is a magnified exploded view of a portion of another embodiment of an insert member for use with a sensor system such as shown in FIG. 29.

The insert 1437 may also include a graphic design 1485 or other indicia thereon. The graphic design 1485 may be provided on one or more graphic layers 1486 positioned on one or both of the layers 1466, 1468 of the insert 1437. In the embodiment illustrated in FIG. 32, the insert 1437 includes an additional graphic layer 1486 that includes a graphic design or indicia 1485 thereon. In this embodiment, the graphic layer 1486 is positioned on top of the first layer 1466 and is sealed to the first layer 1466. The graphic layer 1486 has the same peripheral shape and profile as the first and second layers 1466, 1468, although in another embodiment, the graphic layer 1486 may have a different shape, including a smaller peripheral size than the first and second layers 1466, 1468. Additionally, the graphic layer 1486 may be made of the same material as the other layers 1466, 1468, or a different material. The graphic design 1485 may have any suitable configuration. In one embodiment, as shown in FIG. 33, the graphic design 1485 may contain a stylized or non-stylized depiction of the sensors 1416 and/or other components of the sensor system 1412. The graphic design in FIG. 33 includes graphic depictions of the approximate size, profile shape, and locations of the sensors 1416.

FIG. 33 illustrates an alternate embodiment of the sensor system 1412 of FIGS. 29-32, where the orientations of the layers 1466, 1468 and the orientations of the electrodes 1440, 1442 with respect to the force sensitive material 1444 are reversed. In other words, the first layer 1466 having the conductive material thereon forming the electrodes 1440, 1442 is positioned as the bottom layer in the construction and the second layer 1468 having the force sensitive material 1444 thereon is positioned above the first layer 1466. The layers 1466, 1468, the electrodes 1440, 1442, and the force sensitive material 1444 can otherwise be provided in the same form(s) or configuration(s) described above. Additionally, the embodiment of the sensor system 1412 shown in FIG. 33 contains a graphic layer 1486 that has a graphic design 1485 in the form of a stylized or non-stylized version of the sensors 1416, as mentioned above, which can be used to indicate to a user where the sensors 1416 are located.

Figure 34:
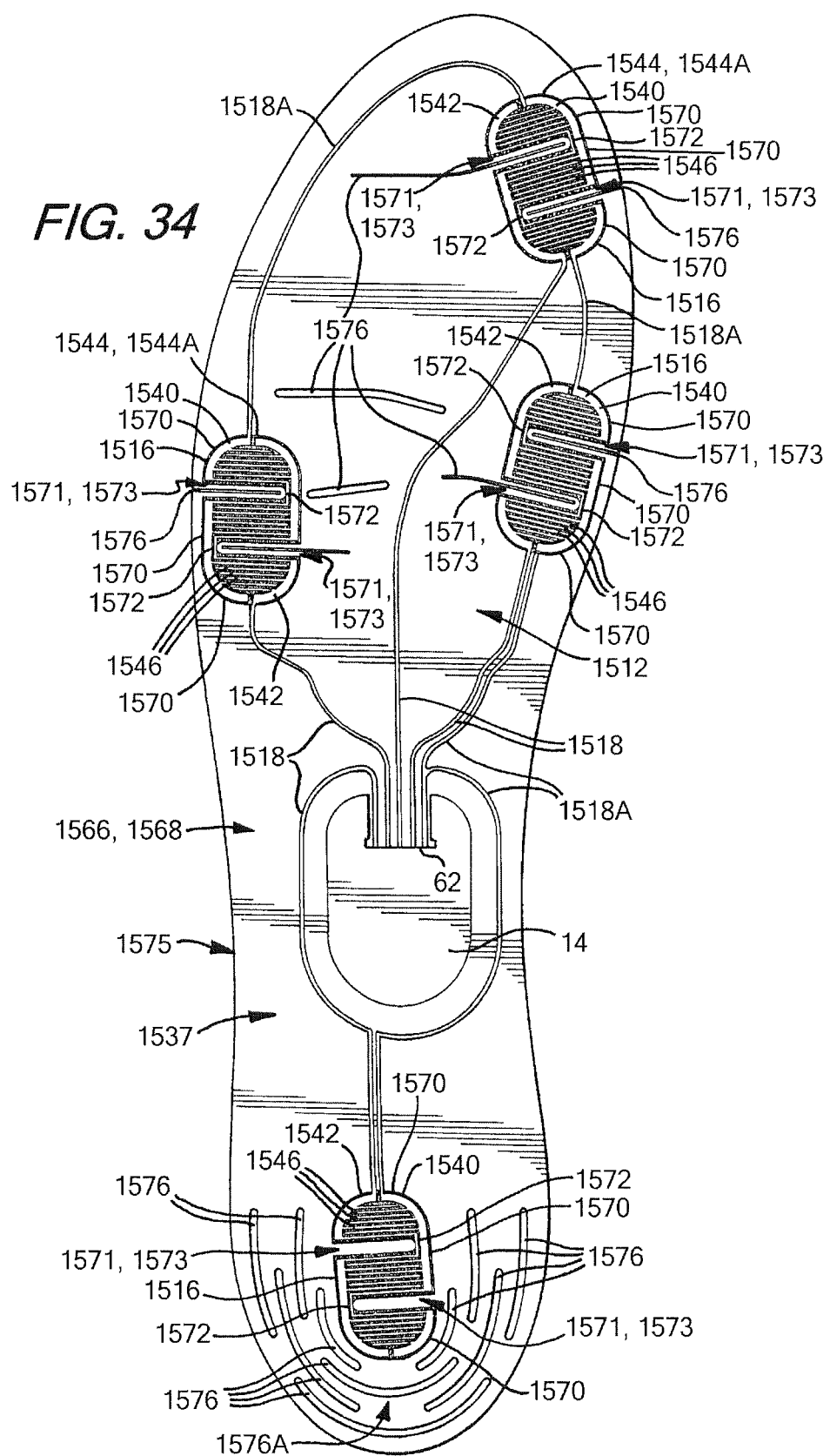
FIG. 34 is a top view of another embodiment of an insert member containing a sensor system according to aspects of the invention.
Figure 35:
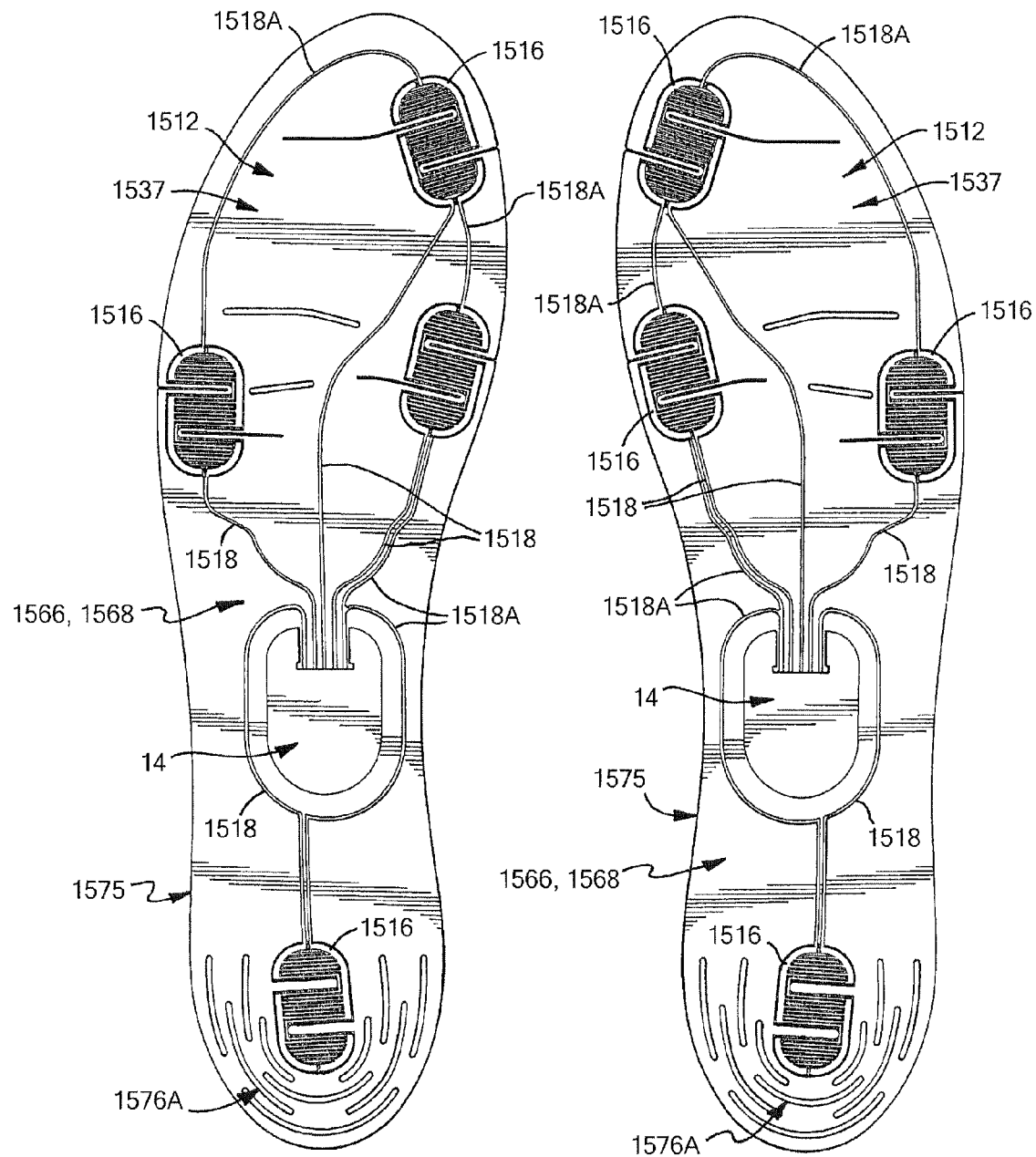
FIG. 35 is a top view of a left and right pair of insert members as shown in FIG. 34.

FIGS. 34-35 illustrate another embodiment of an FSR sensor system 1512 for incorporation into an article of footwear 100. The sensor system 1512 includes four sensors 1516, with a first sensor 1516 positioned in the first phalange (big toe) area, a second sensor 1516 positioned in the first metatarsal head area, a third sensor 1516 positioned in the fifth metatarsal head area, and a fourth sensor 1516 positioned in the heel area, similarly to the configuration shown in FIGS. 29-32. The sensor system 1512 of the embodiment shown in FIGS. 34-35 is configured, in many respects, the same or substantially similar to the sensor system 1412 of the embodiment shown in FIGS. 29-32. Accordingly, at least some features of the sensor system 1512 may be described in lesser detail for the sake of brevity, and it is understood that the description of the sensor system 1416 of FIGS. 29-32 is incorporated into the description of the sensor system 1512, except where differences are noted. It is also understood that the sensor system 1512 may have any characteristics of the embodiment of the sensor system 1412 described above and shown in FIG. 33.

The sensors 1516 illustrated in FIGS. 34-35 are configured substantially the same as the sensors 1416 of FIGS. 29-32. The sensors 1516 of this embodiment each have a sensor lead 1518 connecting the sensor 1516 to the port 14. Additionally, a power lead 1518A extends from the port 14 and is connected to all four sensors 1516 in series configuration to supply power to all four sensors 1516. Similarly to the sensors 1416 in FIGS. 29-32, each sensor 1516 of the sensor system 1512 contains first and second electrodes or electrical contacts 1540, 1542 and a force-sensitive resistive material 1544 disposed between the electrodes 1540, 1542 to electrically connect the electrodes 1540, 1542 together. In this embodiment, similarly to the embodiment of FIGS. 29-32, the electrodes 1540, 1542 are positioned in contact with a surface of the force-sensitive material 1544. Also similarly to the embodiment of FIGS. 29-32, the electrodes 1540, 1542 have a plurality of interlocking or intermeshing fingers 1546. It is understood that the sensors 1516 are structured in the same manner described above with respect to FIGS. 29-32, and likewise function in the same manner.

As shown in FIG. 34, the patches 1544A of the force-sensitive material 1544 in this embodiment have a multi-lobed structure that is formed of a plurality of lobes 1470 that are separate or substantially separate from each other. The patches 1544A of the force-sensitive material 1544 are configured substantially the same as the force-sensitive material 1444 of FIGS. 29-32, having lobes 1570 separated by elongated gaps 1571 with bridges 1572 extending across the gaps 1571 to form electrical connections between the lobes 1570. As similarly described above, the patches 1544A may have a substantially S-shaped structure. As also described above, each electrode 1540, 1542 has at least one a plurality of the fingers 1546 in contact with each of the lobes 1570 of the patches 1544A of the force-sensitive material 1544. As further described above, the electrodes 1540, 1542 in this embodiment have a multi-lobed structure with two enlarged spaces 1573 positioned over the gaps 1571 in the force-sensitive material 1544.

In the embodiment of FIGS. 34-35, the sensor system 1512 is constructed of two flexible layers 1566 and 1568 that combine to form an insert member 1537 for insertion into an article of footwear, as described above with respect to FIGS. 29-32. The first layer 1566 may have the electrodes 1540, 1542 and the leads 1518, 1518A located thereon, and the second layer 1568 may have the force-sensitive material 1544 thereon, as described above. It can be seen from FIGS. 34-35 that the peripheral shape and the contours of the peripheral edge 1575 of the insert 1537 of this embodiment are different from those of the insert 1437 of FIGS. 29-32, and that the shape of the insert 1537 is more similar to the shape of the insert 1337 of FIGS. 27-28. It is understood that the insert 1537 of this embodiment may also include a graphic design or indicia (not shown), which may be provided on a graphic layer (not shown) similar to the graphic design 1485 and the graphic layer 1486 described above and shown in FIGS. 32-33.

The insert 1537 of FIGS. 34-35 has a plurality of slits 1576 in the material of the insert 1537, which may extend completely through the insert 1576. The slits 1576 may be positioned proximate the sensors 1516, including extending within the gaps 1571 or otherwise internally within the sensors 1516, and may extend inwardly from the peripheral edge 1575 of the insert 1537, as similarly to the insert 1437 described above. The slits 1576 of the insert 1537 shown in FIGS. 34-35 are configured differently from the slits 1476 of FIGS. 29-32. Some of the slits 1576 have different lengths and shapes, and the heel sensor 1516 has no slits 1576 within the gaps 1571 of the force-sensitive material 1544. Additionally, the insert 1537 has a number of slits 1576 that do not extend within the sensors 1516, including a plurality of peripheral slits (collectively, 1576A) located around the sensor 1516 in heel region of the insert 1537. The peripheral slits 1576A are curved slits 1576 that follow the contour of the peripheral edge 1575 at the heel region of the insert 1537 and curve around the periphery of the heel sensor 1516. Like the slits 1476 described above and shown in FIGS. 29-32, the slits 1576 may allow for more even flexing of the surrounding areas of the insert 1537, such as during compression of the sensors 1516, which can create a more normal compression of the sensors 1516. For example, the peripheral slits 1576A in the heel region of the insert 1537 allow for the insert 1537 to flex in a "cupping" shape around the sensor 1516 during heel compression, which creates a more normal force on the sensor 1516.

The sensor systems 212, 1312, 1412, 1512 shown in FIGS. 8 and 27-35, as well as the inserts 1337, 1437, 1537 shown in FIGS. 27-35 can be implemented within a shoe 100 between a foot-contacting member 133 and a midsole member 131 as shown in FIGS. 4 and 5. In one embodiment, the FSR sensor system 212, 1312, 1412, 1512 is inserted above the midsole member 131 (and above the strobel, if present) during manufacturing of the shoe 100 after connection of the upper 120 to the midsole 131 and outsole 132, and then the foot-contacting member 133 can be inserted over the sensor system 212, 1312, 1412, 1512. Additionally, in one embodiment, the sensor system 212, 1312, 1412, 1512 can be inserted as part of an insert member, such as the insert members 437, 1337, 1437, 1537 shown in FIGS. 12 and 27-35. FIGS. 11-14 illustrate additional examples of implementing FSR sensors into an article of footwear, such as a shoe 100. The embodiments shown in FIGS. 11-14 illustrate the midsole member 131 having a well 135 therein for receiving an electronic module 22, and a port 14 for connection to the module 22, as described above and shown in FIG. 4. However, it is understood that the well 135 and/or the port 14 may be positioned elsewhere, such as wholly or partially within the foot contacting member 133, as shown in FIG. 5, or elsewhere in the shoe 100.

As one example, FIG. 11 illustrates a portion of a sole structure 130 for an article of footwear containing an FSR sensor system 312, with a midsole member 131 having an FSR sensor assembly 313 connected thereto. In this embodiment, the FSR sensors 316 are partially imbedded within the midsole member 131 and the sensor leads 318 are connected to the top surface of the midsole member 131. It is understood that the midsole member 131 may have a layer covering the sensors 316 to hold them within the midsole member 131, and that the sensors 318 may be wholly or partially imbedded within the midsole member 131, or the midsole member 131 may have "pockets" for insertion of the sensors 316. The midsole member 131 also has the port 14 connected thereto. The port 14 is connected to the sensor leads 318 and is positioned within the well 135 for connection with an electronic module 22 received within the well 135. The sensor leads 318 form an interface 319 proximate the port 14 for connection to the port 14.

As another example, FIG. 12 illustrates a portion of a sole structure 130 for an article of footwear containing an FSR sensor system 412, with an additional sole member 437 containing an FSR sensor assembly 413. In this embodiment, the additional sole member 437 is an insert or liner configured to be inserted between the foot contacting member 133 and the midsole member 131. The insert 437 has FSR sensors 416 and sensor leads 418 connected thereto. The insert 437 may have a configuration similar to the configuration of the insert 1337 described above and shown in FIGS. 27-28, or may have another configuration. Additionally, in this embodiment, the insert 437 is a thin layer of a flexible polymer webbing material having the FSR sensors 416 and the sensor leads 418 mounted thereon to hold the sensors in position. It is understood that the sensors 416 and/or the leads 418 may be wholly or partially embedded within the polymer material of the insert 437. In another embodiment, the insert 437 may consist entirely of the sensor assembly 413, without any binding or webbing material. The insert 437 is also configured for connection of the sensor leads 418 to the port 14 and is positioned such that when the insert 437 is positioned between the foot contacting 133 and the midsole 131, the interface(s) 419 of the sensor leads 418 will be within or adjacent to the well 135 for connection through the port 14 with an electronic module 22 received within the well 135. Additionally, the sole structure 130 can be provided with one or more other inserts 437 having sensors 416 in different configurations. These other inserts 437 can be removed and interchanged by lifting the foot contacting member 133 and replacing one insert with another, differently-configured insert 437. This allows a single article of footwear to be used with different sensor 416 configurations as desired, for different applications. For example, as described below, the sensor system 412 may be configured for communication with an external device 110, and different configurations of sensors 416 can be used for different games or other programs running on the external device 110. Further, the insert 437 may be sized so that it can be used in many different articles of footwear of different sizes, providing versatility.

In an alternate embodiment, shown in FIG. 13, an insert, liner, or other additional sole member 437A can be configured with a sensor assembly 412A for placement on top of an foot contacting member 133. This insert 437A can be configured similarly to the insert 437 described above, such as having a flexible polymer webbing material that has sensors 416A and sensor leads 418A connected thereto. The sensor assembly 412A may contain extended and/or consolidated wire leads 418A that extend around or through the foot contacting member 133, terminating in an interface 419A configured to be connected to the port 14 positioned in the well 135 for connection to an electronic module 22. It is understood that this insert 437A may in some circumstances be considered a "foot contacting member," as the insert 437A forms a top part of the sole structure 130. Similarly to the insert 437 described above, the insert 437A can be removed and interchanged with other inserts 437A having different sensor 416A configurations, and may be sized for placement in footwear having various different sizes.

In another alternate embodiment, an insert member can be produced for connection to another sole member, such as a foot contacting member 133 or a midsole member 131. This insert member may be similar to the inserts 437 and 437A described above and shown in FIGS. 12-13, such as having a flexible webbing material (such as a polymer) that has sensors 416, 416A and sensor leads 418, 418A connected thereto. This configuration enables the sensor assembly 413, 413A to be mounted upon any member of the sole structure 130 as desired, to create a complete sensor system. The insert member may be connectable to a sole member in many different ways, such as by adhesives, fasteners, welding, heat-sealing, or any other suitable technique. It is understood that the insert member 437, 437A, in one embodiment, may have no webbing material and may include only the electronic components of the sensor assembly 413, 413A.

Figure 14:
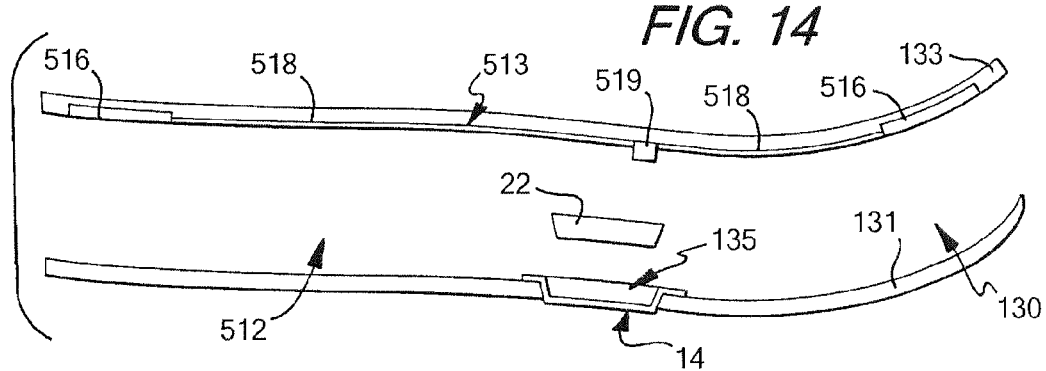

As a further example, FIG. 14 illustrates a portion of a sole structure 130 for an article of footwear containing an FSR sensor system 512, with a foot contacting member 133 having an FSR sensor assembly 513 connected thereto. The foot contacting member 133 illustrated in FIG. 14 is an insole member, however as described above, the foot contacting member 133 may alternately be a bootie element, a strobel, a sockliner, a sock, or other type of foot contacting member for use in an article of footwear. In this embodiment, the FSR sensors 516 are partially imbedded within the foot contacting member 133 and the sensor leads 518 are connected to the bottom surface of the foot contacting member 133. It is understood that the foot contacting member 133 may have a layer covering the sensors 516 to hold them within the foot contacting member 133, and that the sensors 518 may be wholly or partially imbedded within the foot contacting member 133, or that the foot contacting member 133 may have pockets for receiving the sensors 516. The terminal ends of the sensor leads 518 are configured for connection to the port 14 and are positioned such that when the foot contacting member 133 is positioned on top of the midsole member 131, the interface 519 of the leads 518 will be within or adjacent to the well 135 for connection through the port 14 with an electronic module 22 received within the well 135. Additionally, the sole structure 130 can be provided with multiple foot contacting members 133 having sensor assemblies 513 in different configurations. These other foot contacting members 133 can be removed and interchanged by removing the foot contacting member 133 and replacing it with another foot contacting member 133 having sensors 516 in a different configuration. This allows a single article of footwear to be used with different sensor 516 configurations as desired, for different applications, including programs running on the external device 110, as described above.

Figure 15:
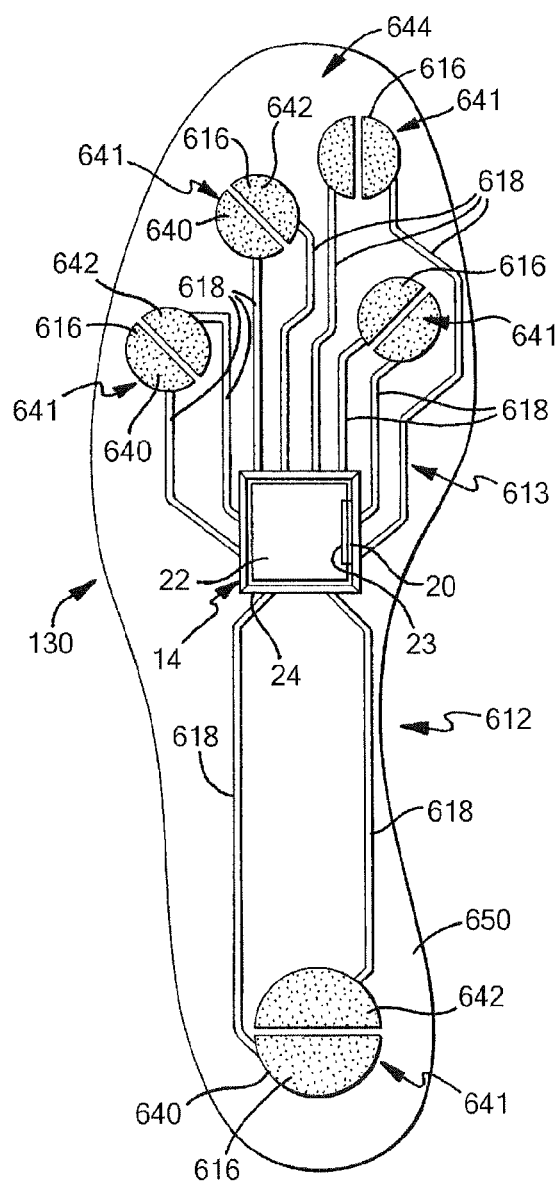
FIG. 15 is a top view of a sole of a shoe incorporating another embodiment of a sensor system utilizing separate electrodes and a force-sensitive resistive element.

FIG. 15 illustrates another exemplary embodiment of a shoe 100 that contains a sensor system 612 that includes a sensor assembly 613 incorporating a plurality of sensors 616. The sensors 616 utilize pairs 641 of electrodes 640, 642 and a separate force-sensitive resistive element 650, containing a force-sensitive resistive material 644 in contact with the electrodes 640, 642. In this embodiment, each electrode pair 641 and the force-sensitive material 644 combine to form a sensor 616 and operate similarly to the electrodes (+) and (−) and the material M described above and shown in FIGS. 9-10. The sensor system 612 can be arranged similarly to the sensor systems 12, 212 described above, and also includes a port 14 in communication with an electronic module 22 and a plurality of leads 618 connecting the electrodes 640, 642 to the port 14. The module 22 is contained within a well or cavity 135 in the sole structure 130 of the shoe 100, and the port 14 is connected within the well 135 to enable connection to the module 22 within the well 135.

The force-sensitive resistive element 650 in FIG. 15 can be any element that is positioned in contact with the electrodes 640, 642. The force-sensitive element 650 may be entirely composed of a force-sensitive resistive material 644, or may be only partially composed of the force-sensitive material 644, such as by including a layer of force-sensitive material 644 or strategically-placed areas containing the force-sensitive material 644. Additionally, the force-sensitive element 650 may be one continuous piece or may include several separate pieces. In one embodiment, such as the embodiments described below and shown in FIGS. 16-20, the force-sensitive element 650 may be contained in a member of the sole structure 130, or may entirely form a member of the sole structure 130.

One material that is suitable for use as the force-sensitive resistive material 244 is a quantum tunneling composite ("QTC"), which provides volume-based resistance behavior. A quantum tunneling composite generally includes a polymer matrix material that contains metallic particles or other conductive particles. Upon compression, the conductive particles move closer together, allowing electrons to tunnel quantum mechanically through the insulative polymer matrix. As the compression increases, the conductive particles move still closer together, allowing more electrical flow and decreasing the measured resistance. The particles in a quantum tunneling composite may have irregular surfaces, which can enable a greater relative range of movement of the particles without the particles contacting each other. This behavior allows for quantitative or binary (on/off) detection of force on the force-sensitive material. Suitable quantum tunneling composite materials can be obtained from Peratech Limited, among other sources.

Another material that is suitable for use as the force-sensitive resistive material 244 is a custom conductive foam, which also provides force-sensitive resistive behavior. A custom conductive foam generally includes a foam made from a conductive material or containing a conductive material additive, such as carbon black or other forms of carbon, or a conductive polymer. The custom conductive foam allows greater conduction of electrons as the foam is compressed, thus decreasing measured resistance. A further material that is suitable for use as the force-sensitive resistive material 244 is a force-transducing rubber. The force-sensitive material 644 may be any other material exhibiting force-sensitive resistive behavior, including any materials described above having volume-based or contact-based resistance.

The electrodes 640, 642 can be made from any of the materials described above with respect to electrodes 240, 242. In one embodiment, the electrodes 640, 642 and/or the leads 618 can be printed onto a surface, such as a foot contacting member 133, a midsole member 131, or another sole member, using a conductive ink. In another embodiment, conductive tape can be used for this purpose, as well as other structures and techniques described above.

The sensor system 612 shown in FIG. 15 can be implemented within a shoe 100 between a foot-contacting member 133 and a midsole member 131 as shown in FIGS. 4 and 5, such as by connecting the force-sensitive resistive element 650 to either the foot-contacting member 133 or the midsole member 131. FIGS. 11-20 illustrate additional examples of implementing sensors using a separate force-sensitive resistive element into an article of footwear, such as a shoe 100. The embodiments shown in FIGS. 11-20 illustrate the midsole member 131 having a well 135 therein for receiving an electronic module 22 and a port 14 for connection to the module 22, as described above and shown in FIG. 4. However, it is understood that the well 135 and/or the port 14 may be positioned elsewhere, such as wholly or partially within the foot contacting member 133, as shown in FIG. 5, or elsewhere in the shoe 100.

As one example, FIG. 16 illustrates a portion of a sole structure 130 for an article of footwear containing a sensor system 712, with a foot contacting member 133 having an electrode assembly 713 connected thereto. In this embodiment, the electrode assembly 713 includes electrode pairs 741 and sensor leads 718 that are connected to the bottom surface of the foot contacting member 133. In one embodiment, the electrode pairs 741 and the sensor leads 718 can be printed on the bottom of the foot contacting member 133, and in another embodiment, the electrode pairs 741 and leads 718 can be contained within a layer on the bottom of the foot contacting member 133. It is understood that the electrode pairs 741 and/or the leads 718 may be wholly or partially imbedded within the foot contacting member 133. The midsole member 131 contains a force-sensitive resistive element 750 in the form of a layer 751 of a force-sensitive resistive material 744 on the top surface thereof. It is understood that this layer 751 may not be continuous in some embodiments. The sensor leads 718 have an interface 719 positioned within or adjacent to the well 135 for connection through the port 14 with an electronic module 22 received within the well 135. Additionally, the sole structure 130 can be provided with multiple foot contacting members 133 having electrode assemblies 713 in different configurations. These other foot contacting members 133 can be removed and interchanged by removing the foot contacting member 133 and replacing it with another foot contacting member 133 having electrode pairs 741 in a different configuration. This allows a single article of footwear to be used with different sensor configurations as desired, for different applications, including programs running on the external device 110, as described above. It is also understood that this configuration can be reversed, with the foot contacting member 133 having the force-sensitive resistive element 750 connected thereto, and the electrode pairs 741 may be connected to the midsole member 131.

In another embodiment, shown in FIG. 17, the sole structure 130 contains a sensor system 812, with a foot contacting member 133 having an electrode assembly 813 connected thereto in the same configuration as the electrode assembly 713 described above and shown in FIG. 16. As similarly described above, the electrode assembly 813 includes electrode pairs 841 and sensor leads 818 that are connected to the bottom surface of the foot contacting member 133, with the leads 818 terminating in an interface 819 for connection to the port 14. However, in the embodiment of FIG. 17, the midsole member 131 itself functions as the force-sensitive resistive element 850, and is composed entirely of the force-sensitive resistive material 844. This embodiment otherwise functions in the same manner as the embodiment shown in FIG. 16, and provides the same interchangeability. It is also understood that this configuration can be reversed, with the foot contacting member 133 functioning as the force-sensitive resistive element 850, composed of the force-sensitive resistive material 844, and the electrode pairs 841 may be connected to the midsole member 131.

As another example, FIG. 18 illustrates a portion of a sole structure 130 for an article of footwear containing a sensor system 912, with a foot contacting member 133, a midsole member 131, and an additional sole member 937 having an electrode assembly 713 connected thereto, positioned between the midsole member 131 and the foot contacting member 133. The electrode assembly 913 includes electrode pairs 941 and sensor leads 918 that are connected to the additional sole member 937. In this embodiment, the additional sole member 133 is an insert 937 made from a thin layer of a flexible polymer webbing material having the electrode pairs 941 and the sensor leads 918 mounted thereon to hold the electrode pairs 941 in position. It is understood that the electrode pairs 941 and/or the leads 918 may be wholly or partially embedded within the polymer material of the insert 937. In another embodiment, the insert 937 may consist entirely of the electrode assembly 913, without any binding or webbing material. The midsole member 131 contains a force-sensitive resistive element 950 in the form of a layer 951 of a force-sensitive resistive material 944 on the top surface thereof, similarly to the force-sensitive element 750 of FIG. 16. It is understood that this layer 951 may not be continuous in some embodiments. The insert 937 also is also configured for connection of the sensor leads 918 to the port 14 and is positioned such that when the insert 937 is positioned between the foot contacting 133 and the midsole 131, the interface 919 of the sensor leads 918 will be within or adjacent to the well 135 for connection through the port 14 with an electronic module 22 received within the well 135. Additionally, the sole structure 130 can be provided with multiple inserts 937 having electrode assemblies 913 in different configurations. These other inserts 937 can be removed and interchanged by lifting the foot contacting member 133 and replacing the insert 937 with another insert 937 having electrode pairs 941 in a different configuration. This allows a single article of footwear to be used with different sensor configurations as desired, for different applications, including programs running on the external device 110, as described above.

In another embodiment, shown in FIG. 19, the sole structure 130 contains a sensor system 1012, with an insert 1037 having an electrode assembly 1013 connected thereto in the same configuration as the electrode assembly 913 described above and shown in FIG. 18. As similarly described above, the electrode assembly 1013 includes electrode pairs 1041 and sensor leads 1018 that are connected to the insert 1037 positioned between the midsole member 131 and the foot contacting member 133, with the leads 1018 terminating in an interface 1019 for connection to the port 14. However, in the embodiment of FIG. 19, the midsole member 131 itself functions as the force-sensitive resistive element 1050, and is composed entirely of the force-sensitive resistive material 1044. This embodiment otherwise functions in the same manner as the embodiment shown in FIG. 18, and provides the same interchangeability. It is understood that, in an alternate embodiment, the foot contacting member 133 may be constructed of the force-sensitive resistive material 1044, functioning as the force-sensitive resistive element 1050. In this configuration, the insert 1037 and/or the electrode assembly 1013 may need to be reconfigured or repositioned to contact the force-sensitive material 1044 on the top side, rather than the bottom side of the insert 1037.

It is understood that, in an alternate embodiment, the inserts 937, 1037 shown in FIGS. 18-19 can be used with the foot contacting member 133 containing or comprising the force-sensitive resistive element 950, 1050. Where the foot contacting member 133 has the layer 951 of the force-sensitive resistive material 944 located on the bottom surface thereof, rather than on the top surface of the midsole member 131, the insert 937 and/or the electrode assembly 913 may need to be reconfigured or re-oriented to contact the force-sensitive material 944 on the top side, rather than the bottom side of the insert 937. The foot contacting member 133 may also have the layer 951 of the force-sensitive material 944 on the top side thereof, in which case, the insert 937, 1037 can be inserted on the top side as well. It is understood that if the entire foot contacting member 133 comprises the force-sensitive resistive element 1050, the insert 937, 1037 can be used on either the top or bottom side of the foot contacting member 133.

In another embodiment, shown in FIG. 20, the sole structure 130 contains a sensor system 1112, with an insert 1137 having an electrode assembly 1113 connected thereto in the same configuration as the electrode assembly 913 described above and shown in FIG. 18. As similarly described above, the electrode assembly 1113 includes electrode pairs 1141 and sensor leads 1118 that are connected to the insert 1137 positioned between the midsole member 131 and the foot contacting member 133, with the leads 1118 terminating in an interface 1119 for connection to the port 14. However, in the embodiment of FIG. 20, the force-sensitive resistive element 1150 is contained in a separate liner 1151 of the force-sensitive resistive material 1144 that is not attached to the midsole member 131 or the foot contacting member 133. The liner 1151 may be entirely composed of the force-sensitive resistive material 1144, or may contain portions or areas composed of the force-sensitive material 1144. Additionally, in this embodiment, the liner 1151 is positioned between the midsole member 131 and the insert 1137, however in another embodiment, the liner 1151 may be positioned between the foot contacting member 133 and the insert 1137. It is understood that, if the position of the liner 1151 is changed, the insert 1137 and/or the electrode assembly 1113 may need to be reconfigured or repositioned to contact the force-sensitive material 1144 on the top side, rather than the bottom side of the insert 1137. Further, in other embodiments, the liner 1151 and insert 1137 can be positioned anywhere in the sole structure 130, as long as the electrode pairs 1141 are in contact with the force-sensitive material 1144. This embodiment otherwise functions in the same manner as the embodiment shown in FIG. 18, and provides the same interchangeability of different electrode assemblies. This embodiment also provides interchangeability of the force-sensitive element 1150, such as if a different material 1144 is desired or if the force-sensitive element becomes damaged or worn out.

In another alternate embodiment, an insert member can be produced for connection to another sole member, such as a foot contacting member 133 or a midsole member 131. This insert member may be similar to the inserts 937, 1037, 1137 described above and shown in FIGS. 18-20, such as having a flexible webbing material (such as a polymer) that has electrode pairs 941, 1041, 1141 and sensor leads 918, 1018, 1118 having ends configured for connection to the port 14, as described above. This configuration enables the electrode assembly 913, 1013, 1113 to be mounted upon any member of the sole structure 130 as desired, to create a complete sensor system. The insert member may be connectable to a sole member in many different ways, such as by adhesives, fasteners, welding, heat-sealing, or any other suitable technique. It is understood that the insert member 937, 1037, 1137, in one embodiment, may have no webbing material and may include only the electronic components of the sensor assembly 913, 1013, 1113.

It is understood that the quantum tunneling composites, custom conductive foams, force transducing rubbers, and other force-sensitive resistive materials discussed herein can be utilized to create individual, self-contained sensors, similar to the FSR sensors 216 described above and shown in FIG. 8, and are not limited to use in sensor assemblies having separate electrodes and force-sensitive elements. Such individual sensors may contain two electrodes and a force-sensitive resistive material, such as illustrated in FIGS. 9-10.

Figure 21:
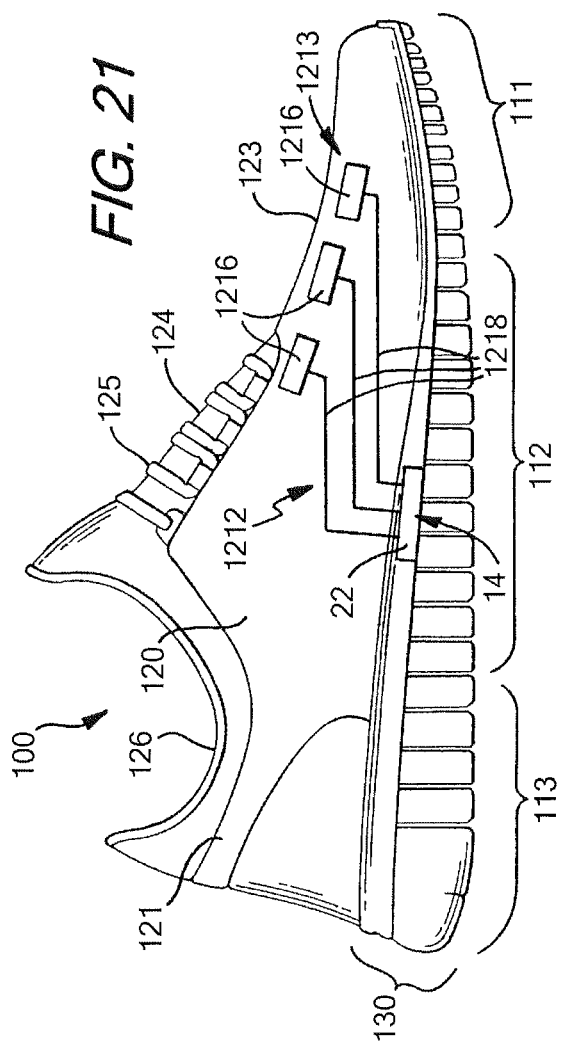
FIG. 21 is a side view of a shoe incorporating another embodiment of a sensor system in an upper of the shoe.

In an alternate embodiment, shown in FIG. 21, the sensor system 1212 may include a sensor assembly 1213 that is connected to the upper 120 of an article of footwear 100, rather than the sole structure 130. Any of the different types of sensors described above can be used in this embodiment, and the sensors can be connected to the upper 120 in any suitable manner. For example, in one embodiment, the sensors 1216 may be FSR sensors that are woven into the material of the upper, with conductive fabrics also woven into the upper to form the leads 1218. In this embodiment, the module 22 is shown contained in the sole 130 of the shoe 100, with the leads 1218 extending from the upper 120 underneath the foot-contacting member 133 to a port 14 in communication with the module 22. However, it is understood that the module 22 may be located elsewhere, including attached to the upper 120, in other embodiments.

The various interchangeable sole inserts described above herein can allow for custom development of sensor systems at a reasonable budget, including interchangeable inserts 437, 437A, 937, 1037, and 1137 having sensor/electrode assemblies 413, 413A, 913, 1013, and 1113, as well as interchangeable foot contacting members 133 having sensor/electrode assemblies 513, 713, and 813. For example, FSR sensor inserts 437 and 437A and the foot contacting member 133 having FSR sensor assembly 513 can be custom-manufactured for various purposes by various different sources, and can be inserted in a wide variety of footwear 100. As another example, inserts 937, 1037, and 1137 and foot contacting members 133 having electrode assemblies 713, 813, 913, 1013, and 1113 can similarly be custom-manufactured and inserted in a wide variety of footwear 100. In one embodiment, footwear 100 can be manufactured containing a force-sensitive resistive material, and any of the sensor assembly configurations 713, 813, 913, 1013, and 1113 can be inserted into the footwear 100 to function with the force-sensitive material. As described above, separate liners 1151 of the force-sensitive resistive material 1144 can also be manufactured for insertion into a wide variety of footwear, further increasing the versatility of the system. As described below, such sensor assemblies can be customized for use with specific software for the electronic module 22 and/or the external device 110. A third party may provide such software along with a sole insert having a customized sensor assembly, as a package.

The operation and use of the sensor systems 12, 212, 312, 412, 412A, 512, 612, 712, 812, 912, 1012, 1112, 1212, 1312, 1412, 1512 are described below with respect to the sensor system 12 shown in FIGS. 3-5, and it is understood that the principles of operation of the sensor system 12, including all embodiments and variations thereof, are applicable to the other embodiments of the sensor systems 212, 312, 412, 412A, 512, 612, 712, 812, 912, 1012, 1112, 1212, 1312, 1412, 1512 described above. In operation, the sensors 16 gather data according to their function and design, and transmit the data to the port 14. The port 14 then allows the electronic module 22 to interface with the sensors 16 and collect the data for later use and/or processing. In one embodiment, the data is collected, stored, and transmitted in a universally readable format, so the data is able to be accessed and/or downloaded by a plurality of users, with a variety of different applications, for use in a variety of different purposes. In one example, the data is collected, stored, and transmitted in XML format. Additionally, in one embodiment, data may be collected from the sensors 16 in a sequential manner, and in another embodiment, data may be collected from two or more sensors 16 simultaneously.

In different embodiments, the sensor system 12 may be configured to collect different types of data. In one embodiment (described above), the sensor(s) 16 can collect data regarding the number, sequence, and/or frequency of compressions. For example, the system 12 can record the number or frequency of steps, jumps, cuts, kicks, or other compressive forces incurred while wearing the footwear 100, as well as other parameters, such as contact time and flight time. Both quantitative sensors and binary on/off type sensors can gather this data. In another example, the system can record the sequence of compressive forces incurred by the footwear, which can be used for purposes such as determining foot pronation or supination, weight transfer, foot strike patterns, or other such applications. In another embodiment (also described above), the sensor(s) 16 are able to quantitatively measure the compressive forces on the adjacent portions of the shoe 100, and the data consequently can include quantitative compressive force and/or impact measurement. Relative differences in the forces on different portions of the shoe 100 can be utilized in determining weight distribution and "center of pressure" of the shoe 100.

The weight distribution and/or center of pressure can be calculated independently for one or both shoes 100, or can be calculated over both shoes together, such as to find a center of pressure or center of weight distribution for a person's entire body. As described above, a relatively densely packed array of on/off binary sensors can be used to measure quantitative forces by changes detected in "puddling" activation of the sensors during moments of greater compression. In further embodiments, the sensor(s) 16 may be able to measure rates of changes in compressive force, contact time, flight time or time between impacts (such as for jumping or running), and/or other temporally-dependent parameters. It is understood that, in any embodiment, the sensors 16 may require a certain threshold force or impact before registering the force/impact.

As described above, the data is provided through the universal port 14 to the module 22 in a universally readable format, so that the number of applications, users, and programs that can use the data is nearly unlimited. Thus, the port 14 and module 22 are configured and/or programmed as desired by a user, and the port 14 and module 22 receive input data from the sensor system 12, which data can be used in any manner desired for different applications. In many applications, the data is further processed by the module 22 and/or the external device 110 prior to use. It is understood that one or more of the sensors 16, the port 14, the module 22, the external device 110 (including the device 110A), and/or any combination of such components may process at least a portion of the data in some embodiments, provided that such components include hardware and/or other structure with processing capability. In configurations where the external device 110 further processes the data, the module 22 may transmit the data to the external device 110. This transmitted data may be transmitted in the same universally-readable format, or may be transmitted in another format, and the module 22 may be configured to change the format of the data. Additionally, the module 22 can be configured and/or programmed to gather, utilize, and/or process data from the sensors 16 for one or more specific applications. In one embodiment, the module 22 is configured for gathering, utilizing, and/or processing data for use in a plurality of applications. Examples of such uses and applications are given below. As used herein, the term "application" refers generally to a particular use, and does not necessarily refer to use in a computer program application, as that term is used in the computer arts. Nevertheless, a particular application may be embodied wholly or partially in a computer program application.

Figure 22:
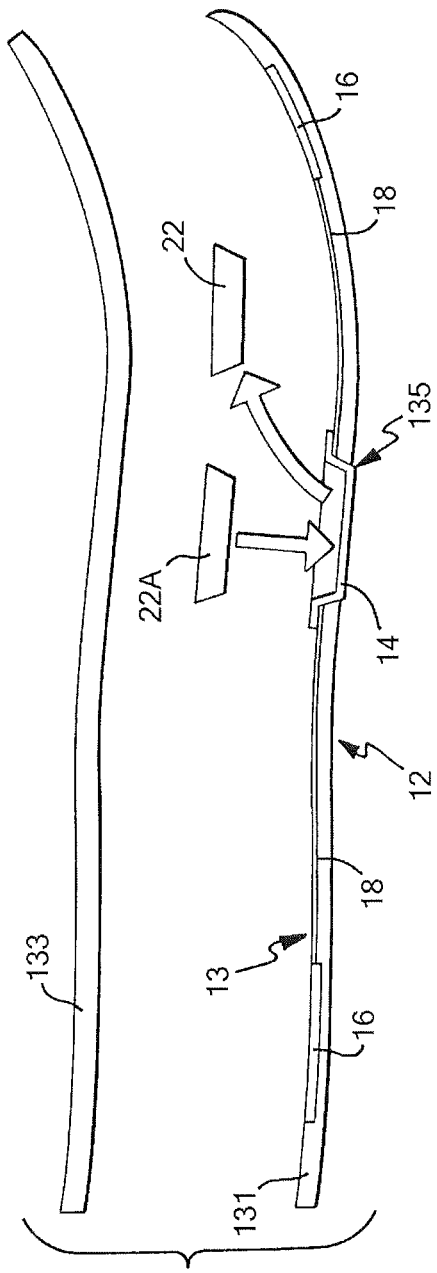
FIG. 22 is a side cross-sectional exploded view of a sole of a shoe showing interchanging of two electronic modules.

Further, as illustrated in the embodiment of FIG. 22, the module 22 can be removed from the footwear 100 and replaced with a second module 22A configured for operating differently than the first module 22. It is understood that the module 22 can be removed and replaced by another module 22A configured in a similar or identical manner, such as replacement due to battery drain, malfunction, etc. In the embodiment of FIG. 22, the replacement is accomplished by lifting the foot contacting member 133, disconnecting the first module 22 from the port 14 and removing the first module 22 from the well 135, then inserting the second module 22A into the well 135 and connecting the second module 22A to the port 14, and finally placing the foot contacting member 133 back into position. The second module 22A may be programmed and/or configured differently than the first module 22. In one embodiment, the first module 22 may be configured for use in one or more specific applications, and the second module 22A may be configured for use in one or more different applications. For example, the first module 22 may be configured for use in one or more gaming applications and the second module 22A may be configured for use in one or more athletic performance monitoring applications. Additionally, the modules 22, 22A may be configured for use in different applications of the same type. For example, the first module 22 may be configured for use in one game or athletic performance monitoring application, and the second module 22A may be configured for use in a different game or athletic performance monitoring application. As another example, the modules 22, 22A may be configured for different uses within the same game or performance monitoring application. In another embodiment, the first module 22 may be configured to gather one type of data, and the second module 22A may be configured to gather a different type of data. Examples of such types of data are described herein, including quantitative force measurement, relative force measurement (i.e. sensors 16 relative to each other), weight shifting/transfer, impact sequences (such as for foot strike patterns) rate of force change, etc. In a further embodiment, the first module 22 may be configured to utilize or process data from the sensors 16 in a different manner than the second module 22A. For example, the modules 22, 22A may be configured to only gather, store, and/or communicate data, or the modules 22, 22A may be configured to further process the data in some manner, such as organizing the data, changing the form of the data, performing calculations using the data, etc. In yet another embodiment, the modules 22, 22A may be configured to communicate differently, such as having different communication interfaces or being configured to communicate with different external devices 110. The modules 22, 22A may function differently in other aspects as well, including both structural and functional aspects, such as using different power sources or including additional or different hardware components, such as additional sensors as described above (e.g. GPS, accelerometer, etc.).

One use contemplated for the data collected by the system 12 is in measuring weight transfer, which is important for many athletic activities, such as a golf swing, a baseball/softball swing, a hockey swing (ice hockey or field hockey), a tennis swing, throwing/pitching a ball, etc. The pressure data collected by the system 12 can give valuable feedback regarding balance and stability for use in improving technique in any applicable athletic field. It is understood that more or less expensive and complex sensor systems 12 may be designed, based on the intended use of the data collected thereby.

The data collected by the system 12 can be used in measurement of a variety of other athletic performance characteristics. The data can be used to measure the degree and/or speed of foot pronation/supination, foot strike patterns, balance, and other such parameters, which can be used to improve technique in running/jogging or other athletic activities. With regard to pronation/supination, analysis of the data can also be used as a predictor of pronation/supination. Speed and distance monitoring can be performed, which may include pedometer-based measurements, such as contact measurement or loft time measurement. Jump height can also be measured, such as by using contact or loft time measurement. Lateral cutting force can be measured, including differential forces applied to different parts of the shoe 100 during cutting. The sensors 16 can also be positioned to measure shearing forces, such as a foot slipping laterally within the shoe 100. As one example, additional sensors may be incorporated into the sides of the upper 120 of the shoe 100 to sense forces against the sides. As another example, a high-density array of binary sensors could detect shearing action through lateral changes in "puddling" of the activated sensors.

In another embodiment, described above, one or more sensors 1216 can additionally or alternately be incorporated into the upper 120 of the shoe 100. The sensors 1216 can be incorporated into the upper 120 in any manner described above. For example, the sensors 1216 may be woven into the material of the upper, with conductive fabrics also woven into the upper to form leads. In this configuration, additional parameters can be measured, such as kick force, such as for soccer or football, as well as number and/or frequency of "touches" in soccer.

The data, or the measurements derived therefrom, may be useful for athletic training purposes, including improving speed, power, quickness, consistency, technique, etc. The port 14, module 22, and/or external device 110 can be configured to give the user active, real-time feedback. In one example, the port 14 and/or module 22 can be placed in communication with a computer, mobile device, etc., in order to convey results in real time. In another example, one or more vibration elements may be included in the shoe 100, which can give a user feedback by vibrating a portion of the shoe to help control motion, such as the features disclosed in U.S. Pat. No. 6,978,684, which is incorporated herein by reference and made part hereof. Additionally, the data can be used to compare athletic movements, such as comparing a movement with a user's past movements to show consistency, improvement, or the lack thereof, or comparing a user's movement with the same movement of another, such as a professional golfer's swing. Further, the system 12 may be used to record biomechanical data for a "signature" athletic movement of an athlete. This data could be provided to others for use in duplicating or simulating the movement, such as for use in gaming applications or in a shadow application that overlays a movement over a user's similar movement.

The system 12 can also be configured for "all day activity" tracking, to record the various activities a user engages in over the course of a day. The system 12 may include a special algorithm for this purpose, such as in the module 22, the external device 110, and/or the sensors 16.

The system 12 may also be used for control applications, rather than data collection and processing applications. In other words, the system 12 could be incorporated into footwear, or another article that encounters bodily contact, for use in controlling an external device 110, such as a computer, television, video game, etc., based on movements by the user detected by the sensors 16. In effect, the footwear with the incorporated sensors 16 and leads 18 extending to a universal port 14 allows the footwear to act as an input system, and the electronic module 22 can be configured, programmed, and adapted to accept the input from the sensors 16 and use this input data in any desired manner, e.g., as a control input for a remote system. For example, a shoe with sensor controls could be used as a control or input device for a computer, or for a program being executed by the computer, similarly to a mouse, where certain foot movements, gestures, etc. (e.g., a foot tap, double foot tap, heel tap, double heel tap, side-to-side foot movement, footpoint, foot-flex, etc.) can control a pre-designated operation on a computer (e.g., page down, page up, undo, copy, cut, paste, save, close, etc.). Software can be provided to assign foot gestures to different computer function controls for this purpose. It is contemplated that an operating system could be configured to receive and recognize control input from the sensor system 12. Televisions or other external electronic devices can be controlled in this manner. Footwear 100 incorporating the system 12 can also be used in gaming applications and game programs, similarly to the Nintendo Wii controller, where specific movements can be assigned certain functions and/or can be used to produce a virtual representation of the user's motion on a display screen. As one example, center of pressure data and other weight distribution data can be used in gaming applications, which may involve virtual representations of balancing, weight shifting, and other performance activities. The system 12 can be used as an exclusive controller for a game or other computer system, or as a complementary controller. Examples of configurations and methods of using sensor systems for articles of footwear as controls for external devices and foot gestures for such controls are shown and described in U.S. Provisional Application No. 61/138,048, which is incorporated by reference herein in its entirety.

Figure 23:
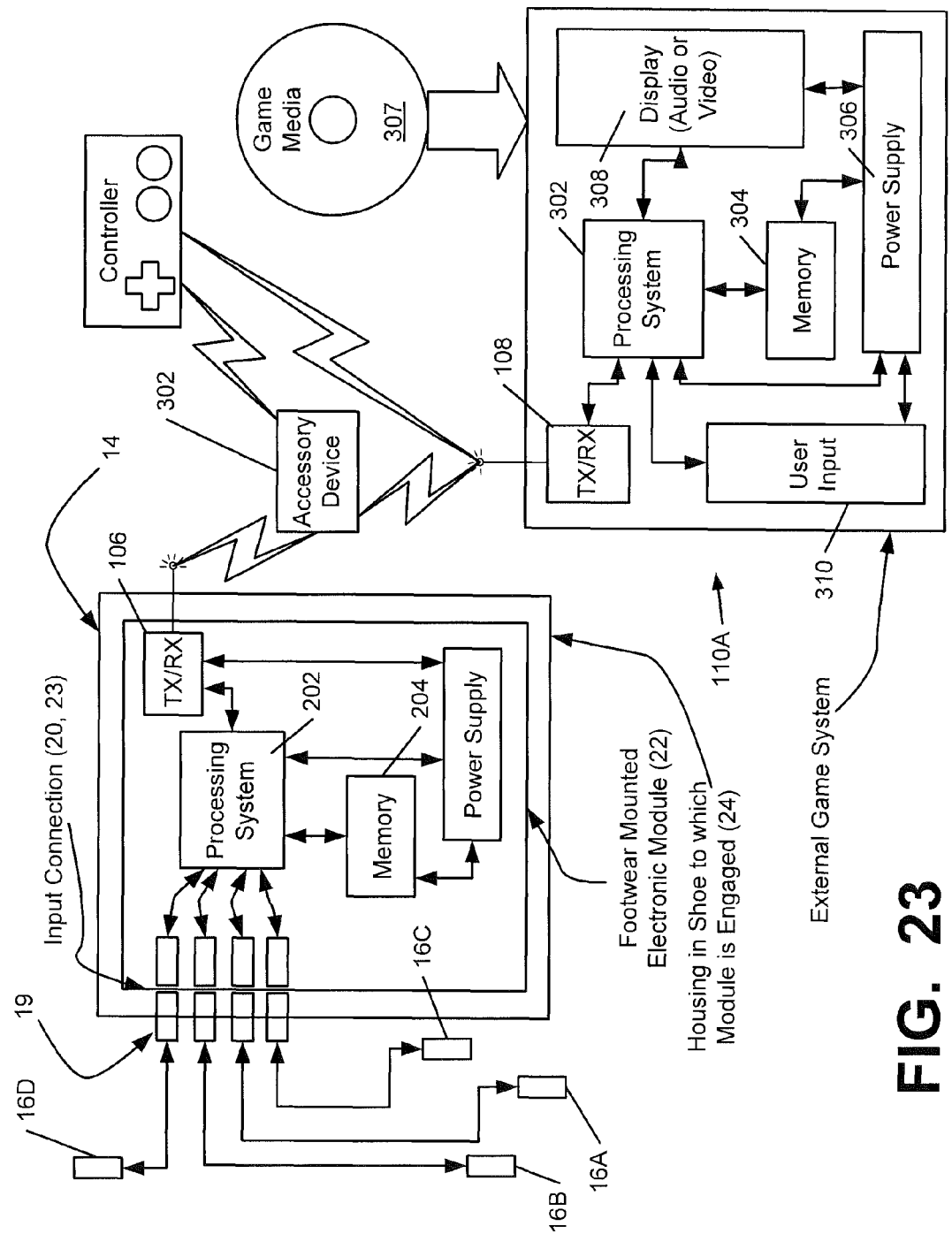
FIG. 23 is a schematic diagram of the electronic module of FIG. 6, in communication with an external gaming device.

Additionally, the system 12 may be configured to communicate directly with the external device 110 and/or with a controller for the external device. As described above, FIG. 6 illustrates one embodiment for communication between the electronic module 22 and the external device. In another embodiment, shown in FIG. 23, the system 12 can be configured for communication with an external gaming device 110A. The external gaming device 110A contains similar components to the exemplary external device 110 shown in FIG. 6. The external gaming device 110A also includes at least one game media 307 containing a game program (e.g. a cartridge, CD, DVD, Blu-Ray, or other storage device), and at least one remote controller 305 configured to communicate by wired and/or wireless connection through the transmitting/receiving element 108. In the embodiment shown, the controller 305 complements the user input 310, however in one embodiment, the controller 305 may function as the sole user input. In this embodiment, the system 12 is provided with an accessory device 303, such as a wireless transmitter/receiver with a USB plug-in, that is configured to be connected to the external device 110 and/or the controller 305 to enable communication with the module 22. In one embodiment, the accessory device 303 may be configured to be connected to one or more additional controllers and/or external devices, of the same and/or different type than the controller 305 and the external device 110. It is understood that if the system 12 includes other types of sensors described above (e.g., an accelerometer), such additional sensors can also be incorporated into controlling a game or other program on an external device 110.

An external device 110, such as a computer/gaming system, can be provided with other types of software to interact with the system 12. For example, a gaming program may be configured to alter the attributes of an in-game character based on a user's real-life activities, which can encourage exercise or greater activity by the user. In another example, a program may be configured to display an avatar of the user that acts in relation or proportion to the user activity collected by the sensing system of the shoe. In such a configuration, the avatar may appear excited, energetic, etc., if the user has been active, and the avatar may appear sleepy, lazy, etc., if the user has been inactive. The sensor system 12 could also be configured for more elaborate sensing to record data describing a "signature move" of an athlete, which could then be utilized for various purposes, such as in a gaming system or modeling system.

Figure 24:
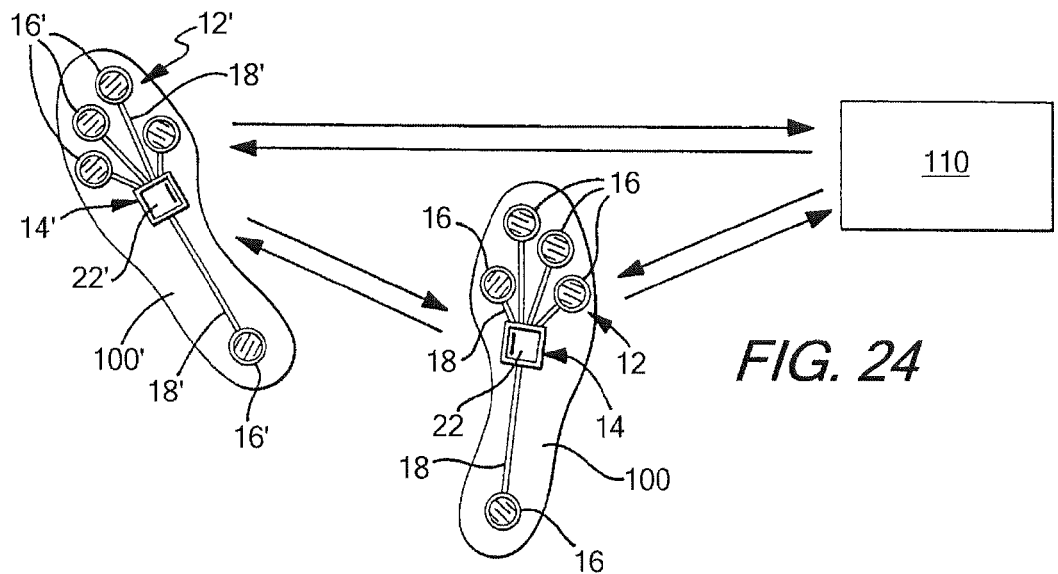
FIG. 24 is a schematic diagram of a pair of shoes, each containing a sensor system, in a mesh communication mode with an external device.
Figure 25:
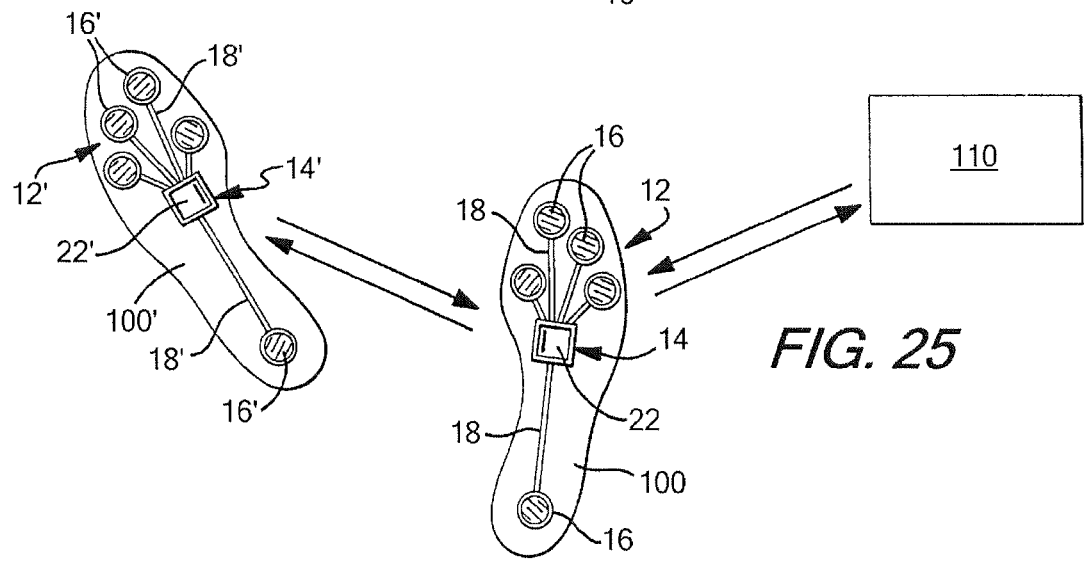
FIG. 25 is a schematic diagram of a pair of shoes, each containing a sensor system, in a "daisy chain" communication mode with an external device.
Figure 26:
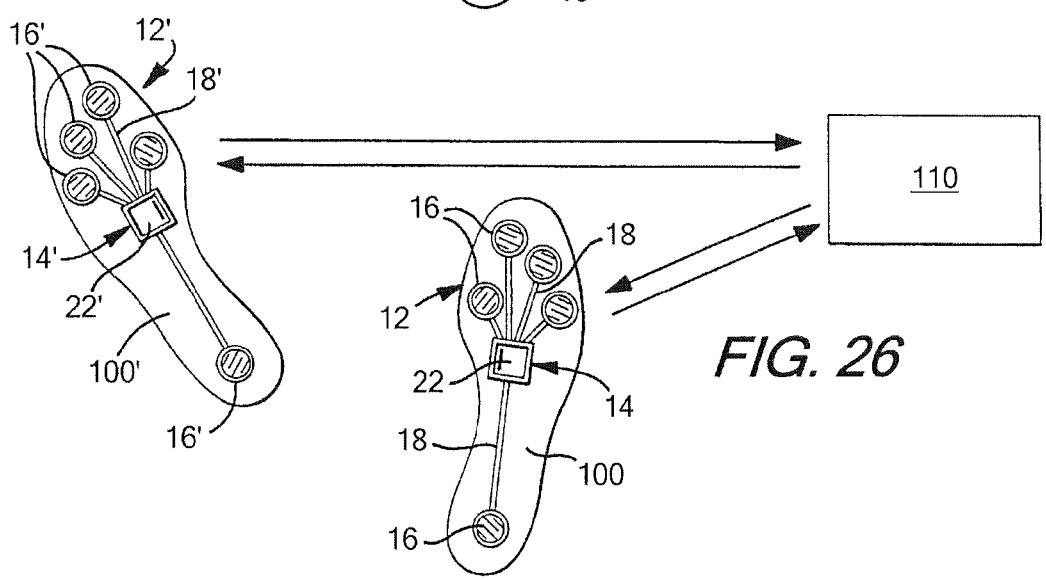
FIG. 26 is a schematic diagram of a pair of shoes, each containing a sensor system, in an independent communication mode with an external device.

A single article of footwear 100 containing the sensor system 12 as described herein can be used alone or in combination with a second article of footwear 100' having its own sensor system 12', such as a pair of shoes 100, 100' as illustrated in FIGS. 24-26. The sensor system 12' of the second shoe 100' generally contains one or more sensors 16' connected by sensor leads 18' to a port 14' in communication with an electronic module 22'. The second sensor system 12' of the second shoe 100' shown in FIGS. 24-26 has the same configuration as the sensor system 12 of the first shoe 100. However, in another embodiment, the shoes 100, 100' may have sensor systems 12, 12' having different configurations. The two shoes 100, 100' are both configured for communication with the external device 110, and in the embodiment illustrated, each of the shoes 100, 100' has an electronic module 22, 22' configured for communication with the external device 110. In another embodiment, both shoes 100, 100' may have ports 14, 14' configured for communication with the same electronic module 22. In this embodiment, at least one shoe 100, 100' may be configured for wireless communication with the module 22. FIGS. 24-26 illustrate various modes for communication between the modules 22, 22'

FIG. 24 illustrates a "mesh" communication mode, where the modules 22, 22' are configured for communicating with each other, and are also configured for independent communication with the external device 110. FIG. 25 illustrates a "daisy chain" communication mode, where one module 22' communicates with the external device 110 through the other module 22. In other words, the second module 22' is configured to communicate signals (which may include data) to the first module 22, and the first module 22 is configured to communicate signals from both modules 22, 22' to the external device 110. Likewise, the external device communicates with the second module 22' through the first module 22, by sending signals to the first module 22, which communicates the signals to the second module 22'. In one embodiment, the modules 22, 22' can also communicate with each other for purposes other than transmitting signals to and from the external device 110. FIG. 26 illustrates an "independent" communication mode, where each module 22, 22' is configured for independent communication with the external device 110, and the modules 22, 22' are not configured for communication with each other. In other embodiments, the sensor systems 12, 12' may be configured for communication with each other and/or with the external device 110 in another manner.

Still other uses and applications of the data collected by the system 12 are contemplated within the scope of the invention and are recognizable to those skilled in the art.

As will be appreciated by one of skill in the art upon reading the present disclosure, various aspects described herein may be embodied as a method, a data processing system, or a computer program product. Accordingly, those aspects may take the form of an entirely hardware embodiment, an entirely software embodiment or an embodiment combining software and hardware aspects. Furthermore, such aspects may take the form of a computer program product stored by one or more tangible computer-readable storage media or storage devices having computer-readable program code, or instructions, embodied in or on the storage media. Any suitable tangible computer readable storage media may be utilized, including hard disks, CD-ROMs, optical storage devices, magnetic storage devices, and/or any combination thereof. In addition, various intangible signals representing data or events as described herein may be transferred between a source and a destination in the form of electromagnetic waves traveling through signal-conducting media such as metal wires, optical fibers, and/or wireless transmission media (e.g., air and/or space).

As described above, aspects of the present invention may be described in the general context of computer-executable instructions, such as program modules, being executed by a computer and/or a processor thereof. Generally, program modules include routines, programs, objects, components, data structures, etc. that perform particular tasks or implement particular abstract data types. Such a program module may be contained in a tangible computer-readable medium, as described above. Aspects of the present invention may also be practiced in distributed computing environments where tasks are performed by remote processing devices that are linked through a communications network. Program modules may be located in a memory, such as the memory 204 of the module 22 or memory 304 of the external device 110, or an external medium, such as game media 307, which may include both local and remote computer storage media including memory storage devices. It is understood that the module 22, the external device 110, and/or external media may include complementary program modules for use together, such as in a particular application. It is also understood that a single processor 202, 302 and single memory 204, 304 are shown and described in the module 22 and the external device 110 for sake of simplicity, and that the processor 202, 302 and memory 204, 304 may include a plurality of processors and/or memories respectively, and may comprise a system of processors and/or memories.

The various embodiments of the sensor system described herein, as well as the articles of footwear, foot contacting members, inserts, and other structures incorporating the sensor system, provide benefits and advantages over existing technology. For example, many of the sensor embodiments described herein provide relatively low cost and durable options for sensor systems, so that a sensor system can be incorporated into articles of footwear with little added cost and good reliability. As a result, footwear can be manufactured with integral sensor systems regardless of whether the sensor systems are ultimately desired to be used by the consumer, without appreciably affecting price. Additionally, sole inserts with customized sensor systems can be inexpensively manufactured and distributed along with software designed to utilize the sensor systems, without appreciably affecting the cost of the software. As another example, the sensor system provides a wide range of functionality for a wide variety of applications, including gaming, fitness, athletic training and improvement, practical controls for computers and other devices, and many others described herein and recognizable to those skilled in the art. In one embodiment, third-party software developers can develop software configured to run using input from the sensor systems, including games and other programs. The ability of the sensor system to provide data in a universally readable format greatly expands the range of third party software and other applications for which the sensor system can be used. Additionally, in one embodiment, the sensor system can produce signals and data that permit accurate detection of applied forces, which provides greater utility and versatility. As a further example, the various sole inserts containing sensor systems, including liners, insoles, and other elements, permit interchangeability and customization of the sensor system for different applications. Still further, the configurations of inserts having cut-out portions and/or slits allow for more even flexing of the insert, and assist in maintaining a more normal (i.e. perpendicular) force on the sensors during compression. This allows the sensors to function more effectively and give a cleaner signal with less noise and/or distortion. Other advantages are recognizable to those skilled in the art.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "Providing" an article or apparatus, as used herein, refers broadly to making the article available or accessible for future actions to be performed on the article, and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention and the scope of protection is only limited by the scope of the accompanying Claims.

What is claimed is:

1. An insert for use with an article of footwear adapted to engage a foot, the article of footwear having a sole structure and an upper portion connected to the sole structure, the insert comprising:
    an insert member adapted to be placed in contact with the sole structure of the article of footwear, the insert member comprising an arch portion adapted to engage an arch region of the foot and a forefoot portion connected to a front of the arch portion and adapted to engage a forefoot area of the foot, the insert member having a peripheral edge defining a periphery of the insert member, and wherein the peripheral edge comprises a medial edge adapted to be located on a medial side of the foot and a lateral edge opposite the medial edge and adapted to be located on a lateral side of the foot,
    wherein the arch portion has a first width measured between the medial and lateral edges and the forefoot portion has a second width measured between the medial and lateral edges, wherein the second width is greater than the first width,
    wherein the medial edge includes a medial concave edge segment located between the arch portion and the forefoot portion, and the lateral edge includes a lateral concave edge segment located between the arch portion and the forefoot portion, wherein the medial and lateral concave edge segments extend outwardly from the arch portion to the forefoot portion to create the second width of the forefoot portion that is greater than the first width of the arch portion; and
    a sensor system comprising a plurality of force sensors connected to the insert member and a port adapted for communication with an electronic device, wherein the port is positioned on the arch portion of the insert member, and wherein at least one of the force sensors is positioned on the forefoot portion,
    wherein the forefoot portion and the arch portion form a central portion of the insert member, and wherein the insert member further comprises a first phalange portion extending from a front of the forefoot portion and adapted to be engaged by a first phalange of the foot, and a heel portion extending from a rear of the arch portion and adapted to be engaged by a heel of the foot.

2. The insert of claim 1, wherein the plurality of force sensors further includes a first phalange sensor located on the first phalange portion and a heel sensor located on the heel portion.

3. The insert of claim 2, wherein the sensor system comprises at least four force sensors, including the first phalange sensor, the heel sensor, and a first metatarsal sensor and a fifth metatarsal sensor positioned on the forefoot portion of the insert member.

4. The insert of claim 1, wherein the medial edge comprises a front medial edge extending from the forefoot portion to the first phalange portion, and the lateral edge comprises a front lateral edge extending from the forefoot portion to the first phalange portion, and wherein the front medial edge has an outwardly-curved shape and the front lateral edge has an inwardly-curved shape.

5. The insert of claim 1, wherein the medial edge comprises a rear medial edge extending from the arch portion to the heel portion, and the lateral edge comprises a rear lateral edge extending from the arch portion to the heel portion, and wherein the rear medial edge and the rear lateral edge each have at least one inwardly-curved edge.

6. The insert of claim 1, wherein the sensor system further comprises a plurality of leads extending from the port to each of the plurality of force sensors.

7. The insert of claim 1, wherein the plurality of force sensors are force sensitive resistor sensors comprising two electrodes and a force sensitive resistive material positioned between the electrodes.

8. The insert of claim 1, wherein the insert member comprises a first layer and a second layer of flexible polymer webbing, wherein the first and second layers are superimposed, and the force sensors are located between the first and second layers.

9. The insert of claim 1, wherein the port further comprises a housing connected to the arch portion of the insert member and configured to receive the electronic device therein.

10. An insert for use with an article of footwear adapted to engage a foot, the article of footwear having a sole structure and an upper portion connected to the sole structure, the insert comprising:
    an insert member formed of first and second layers of flexible polymer material positioned in a superimposed manner, the insert member adapted to be placed in contact with the sole structure of the article of footwear, the insert member comprising:
    a central portion comprising an arch portion adapted to engage an arch region of the foot and a forefoot portion connected to a front of the arch portion and adapted to engage a forefoot area of the foot;
    a first phalange portion extending from a front of the forefoot portion and adapted to be engaged by a first phalange of the foot; and
    a heel portion extending from a rear of the arch portion and adapted to be engaged by a heel of the foot,
    wherein the insert member has a peripheral edge defining a periphery of the insert member, and wherein the peripheral edge comprises a medial edge adapted to be located on a medial side of the foot and a lateral edge opposite the medial edge and adapted to be located on a lateral side of the foot, wherein the arch portion has a first width measured between the medial and lateral edges and the forefoot portion has a second width measured between the medial and lateral edges, wherein the second width is greater than the first width, wherein the medial edge includes a medial edge segment located between the arch portion and the forefoot portion, and the lateral edge includes a lateral edge segment located between the arch portion and the forefoot portion, wherein the medial and lateral edge segments are inwardly curved and extend outwardly from the arch portion to the forefoot portion to create the second width of the forefoot portion that is greater than the first width of the arch portion; and a sensor system comprising a plurality of force sensors connected to the insert member, a port adapted for communication with an electronic device, and a plurality of leads extending from the force sensors to the port, wherein the port is positioned on the arch portion of the insert member, wherein the force sensors and leads are located between the first and second layers of the insert member, and wherein the plurality of force sensors includes at least a first phalange sensor located on the first phalange portion, a heel sensor located on the heel portion, and a first metatarsal sensor and a fifth metatarsal sensor located on the forefoot portion of the insert member.

11. The insert of claim 10, wherein the medial edge comprises a front medial edge extending from the forefoot portion to the first phalange portion, and the lateral edge comprises a front lateral edge extending from the forefoot portion to the first phalange portion, and wherein the front medial edge has an outwardly-curved shape and the front lateral edge has an inwardly-curved shape.

12. The insert of claim 10, wherein the medial edge comprises a rear medial edge extending from the arch portion to the heel portion, and the lateral edge comprises a rear lateral edge extending from the arch portion to the heel portion, and wherein the rear medial edge and the rear lateral edge each have at least one inwardly-curved edge.

13. An article of footwear adapted to engage a foot, comprising:
  a sole structure;
  an upper portion connected to the sole structure;
  an insert member in contact with the sole structure, the insert member comprising:
    an arch portion adapted to engage an arch region of the foot;
    a forefoot portion connected to a front of the arch portion and adapted to engage a forefoot area of the foot;
    a peripheral edge defining a periphery of the insert member, wherein the peripheral edge comprises a medial edge adapted to be located on a medial side of the foot and a lateral edge opposite the medial edge and adapted to be located on a lateral side of the foot,
    wherein the arch portion has a first width measured between the medial and lateral edges and the forefoot portion has a second width measured between the medial and lateral edges, wherein the second width is greater than the first width,
    wherein the medial edge includes a medial concave edge segment located between the arch portion and the forefoot portion, and the lateral edge includes a lateral concave edge segment located between the arch portion and the forefoot portion, wherein the medial and lateral concave edge segments extend outwardly from the arch portion to the forefoot portion to create the second width of the forefoot portion that is greater than the first width of the arch portion, and
    wherein the forefoot portion and the arch portion form a central portion of the insert member, and wherein the insert member further comprises a first phalange portion extending from a front of the forefoot portion and adapted to be engaged by a first phalange of the foot, and a heel portion extending from a rear of the arch portion and adapted to be engaged by a heel of the foot; and
  a sensor system comprising a plurality of force sensors connected to the insert member and a port adapted for communication with an electronic device, wherein the port is positioned on the arch portion of the insert member, and wherein at least one of the force sensors is positioned on the forefoot portion.

14. The article of footwear of claim 13, wherein the plurality of force sensors further includes a first phalange sensor located on each of the first phalange portion and a heel sensor located on the heel portion.

15. The article of footwear of claim 14, wherein the sensor system comprises at least four force sensors, including the first phalange sensor, the heel sensor, and a first metatarsal sensor and a fifth metatarsal sensor positioned on the forefoot portion of the insert member.

16. The article of footwear of claim 13, wherein the medial edge comprises a front medial edge extending from the forefoot portion to the first phalange portion, and the lateral edge comprises a front lateral edge extending from the forefoot portion to the first phalange portion, and wherein the front medial edge has an outwardly-curved shape and the front lateral edge has an inwardly-curved shape.

17. The article of footwear of claim 13, wherein the medial edge comprises a rear medial edge extending from the arch portion to the heel portion, and the lateral edge comprises a rear lateral edge extending from the arch portion to the heel portion, and wherein the rear medial edge and the rear lateral edge each have at least one inwardly-curved edge.

18. The article of footwear of claim 13, wherein the sensor system further comprises a plurality of leads extending from the port to each of the plurality of force sensors.

19. The article of footwear of claim 13, wherein the plurality of force sensors are force sensitive resistor sensors comprising two electrodes and a force sensitive resistive material positioned between the electrodes.

20. The article of footwear of claim 13, wherein the insert member comprises a first layer and a second layer of flexible polymer webbing, wherein the first and second layers are superimposed, and the force sensors are located between the first and second layers.

21. The article of footwear of claim 13, wherein the port further comprises a housing connected to the arch portion of the insert member and configured to receive the electronic device therein.

22. The article of footwear of claim 21, wherein sole structure further includes a well located below the arch portion of the insert member, and wherein the housing is at least partially received within the well.

23. The article of footwear of claim 13, wherein sole structure further comprises a foot contacting member configured to directly engage the foot when the foot is engaged by the article of footwear, and wherein the insert member is positioned beneath the foot contacting member.

24. An insert for use with an article of footwear adapted to engage a foot, the article of footwear having a sole structure and an upper portion connected to the sole structure, the insert comprising:
  an insert member adapted to be placed in contact with the sole structure of the article of footwear, the insert member comprising an arch portion adapted to engage an arch region of the foot and a forefoot portion connected to a front of the arch portion and adapted to engage a forefoot area of the foot, the insert member having a peripheral edge defining a periphery of the insert member, and wherein the peripheral edge comprises a medial edge adapted to be located on a medial side of the foot and a lateral edge opposite the medial edge and adapted to be located on a lateral side of the foot,
  wherein the arch portion has a first width measured between the medial and lateral edges and the forefoot portion has a second width measured between the medial and lateral edges, wherein the second width is greater than the first width,
  wherein the medial edge includes a medial concave edge segment located between the arch portion and the forefoot portion, and the lateral edge includes a lateral concave edge segment located between the arch portion and the forefoot portion, wherein the medial and lateral concave edge segments extend outwardly from the arch portion to the forefoot portion to create the second width of the forefoot portion that is greater than the first width of the arch portion; and
  a sensor system comprising a plurality of force sensors connected to the insert member and a port adapted for communication with an electronic device, wherein the port is positioned on the arch portion of the insert member, and wherein at least one of the force sensors is positioned on the forefoot portion,
  wherein the plurality of force sensors are force sensitive resistor sensors comprising two electrodes and a force sensitive resistive material positioned between the electrodes.

25. An article of footwear adapted to engage a foot, comprising:
  a sole structure;
  an upper portion connected to the sole structure;
  an insert member in contact with the sole structure, the insert member comprising:
    an arch portion adapted to engage an arch region of the foot;
    a forefoot portion connected to a front of the arch portion and adapted to engage a forefoot area of the foot;
    a peripheral edge defining a periphery of the insert member, wherein the peripheral edge comprises a medial edge adapted to be located on a medial side of the foot and a lateral edge opposite the medial edge and adapted to be located on a lateral side of the foot,
  wherein the arch portion has a first width measured between the medial and lateral edges and the forefoot portion has a second width measured between the medial and lateral edges, wherein the second width is greater than the first width,
  wherein the medial edge includes a medial concave edge segment located between the arch portion and the forefoot portion, and the lateral edge includes a lateral concave edge segment located between the arch portion and the forefoot portion, wherein the medial and lateral concave edge segments extend outwardly from the arch portion to the forefoot portion to create the second width of the forefoot portion that is greater than the first width of the arch portion; and
  a sensor system comprising a plurality of force sensors connected to the insert member and a port adapted for communication with an electronic device, wherein the port is positioned on the arch portion of the insert member, and wherein at least one of the force sensors is positioned on the forefoot portion,
  wherein the plurality of force sensors are force sensitive resistor sensors comprising two electrodes and a force sensitive resistive material positioned between the electrodes.

* * * * *